(12) United States Patent
Watkins et al.

(10) Patent No.: US 11,987,830 B2
(45) Date of Patent: May 21, 2024

(54) CELL-FREE PROTEIN SYNTHESIS SYSTEMS

(71) Applicant: LAWRENCE LIVERMORE NATIONAL SECURITY, LLC, Livermore, CA (US)

(72) Inventors: Nicholas N. Watkins, Livermore, CA (US); Neil Reginald Beer, Livermore, CA (US); Kenneth W. Turteltaub, Livermore, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 672 days.

(21) Appl. No.: 16/752,222

(22) Filed: Jan. 24, 2020

(65) Prior Publication Data
US 2020/0255881 A1  Aug. 13, 2020

Related U.S. Application Data

(60) Provisional application No. 62/796,427, filed on Jan. 24, 2019.

(51) Int. Cl.
| | |
|---|---|
| *C12P 21/02* | (2006.01) |
| *A61K 38/00* | (2006.01) |
| *B01D 15/38* | (2006.01) |
| *C12N 11/14* | (2006.01) |
| *C12N 11/18* | (2006.01) |
| *C12P 21/00* | (2006.01) |

(52) U.S. Cl.
CPC .......... *C12P 21/02* (2013.01); *B01D 15/3809* (2013.01); *C12N 11/18* (2013.01); *C12P 21/00* (2013.01); *A61K 38/00* (2013.01)

(58) Field of Classification Search
None
See application file for complete search history.

(56) References Cited

U.S. PATENT DOCUMENTS

| 7,297,532 | B2 | 11/2007 | Puglisi et al. | |
|---|---|---|---|---|
| 2012/0178640 | A1 | 7/2012 | Strano et al. | |
| 2014/0099724 | A1* | 4/2014 | Skach ................ | G01N 33/6803 436/86 |

OTHER PUBLICATIONS

Calmer, M., et al. 2017 Active ribosome profiling with RiboLace (preprint copy). bioRxiv doi:10.1101/179671, 21 pages. (Year: 2017).*
Lee, K-H., et al. 2012 Lab Chip 12: 1605-1610. (Year: 2012).*
Novex Life Technologies Ni-NTA purification system product sheets 2015: 32 pages. (Year: 2015).*
Banerjee et al., Location-specific biological functionalization on nanotubes: Attachment of proteins at the ends of nanotubes using Au nanocrystal masks, Nano Lett., 3(3):283-287 (2003).
Baumann et al., High surface area carbon aerogel monoliths with hierarchical porosity, Journal of Non-Crystalline Solids, 354:3513-3515 (2008).
Becker et al., Hot embossing as a method for the fabrication of polymer high aspect ratio structures, Sensors Actuators, A. Phys., 83(1):130-135 (2000).
Beckett et al., A minimal peptide substrate in biotin holoenzyme synthetase-catalyzed biotinylation, Protein Sci., 8:921-929 (1999).
Beebe et al., Functional hydrogel structures for autonomous flow control inside microfluidic channels : Abstract: Nature, Nature, 404(6778):588-590 (2000).
Biener et al., Macroscopic 3D nanographene with dynamically tunable bulk properties, Adv. Mater., 24:5083-5087 (2012).
Blanchette et al., Printable enzyme-embedded materials for methane to methanol conversion, Nat. Commun., 7:1-9 (2016).
Boer et al., Efficient biotinylation and single-step purification of tagged transcription factors in mammalian cells and transgenic mice, Proc. Natl. Acad. Sci. U.S.A., 100(13):7480-5 (2003).
Brody et al., Diffusion-based extraction in a microfabricated device, Sensors Actuators A Phys., 58(1):13-18 (1997).
Chen et al., Durable superhydrophobic/superoleophilic graphene-based foam for high-efficiency oil spill cleanups and recovery, Environ. Sci. Technol., 53(3):1509-1517 (2019).
Chou, Nanoimprint lithography, J. Vac. Sci. Technol. B, 14(6):4129-4133 (1996).
Copic et al., Monodisperse CNT microspheres for high permeability and efficiency flow-through filtration applications, Adv. Mater., 30:1706503 (2018).
Dhopeshwarkar et al., Electrokinetic concentration enrichment within a microfluidic device using a hydrogel microplug, Lab Chip, 5(10):1148-54 (2005).
Dubois et al., Synthesis, structure, and properties of model organic surfaces, Annu. Rev. Phys. Chem., 43:437-463 (1992).
Duffy et al., Rapid prototyping of microfluidic systems in poly (dimethylsiloxane), Anal. Chem., 70(23):4974-4984 (1998).
Hensleigh et al., Additive manufacturing of complex micro-architected graphene aerogels, Mater. Horiz., 5:1035-1041 (2018).
Hoffman, Hydrogels for biomedical applications, Adv. Drug Deliv. Rev., 64(Suppl):18-23 (2012).
Hofmann et al., Adaptation of capillary isoelectric focusing to microchannels on a glass chip, Anal. Chem., 71(3):678-686 (1999).
Ingolia et al., Ribosome profiling reveals pervasive translation outside of annotated protein-coding genes, Cell Rep., 8(5):1365-1379 (2014).
Jung et al., Electrical and field-emission properties of chemically anchored single-walled carbon nanotube patterns, Appl. Phys. Lett., 87(1):1-4 (2005).
Katranidis et al., Fast biosynthesis of GFP molecules: A single-molecule fluorescence study, Angew. Chemie—Int. Ed., 48(10):1758-1761 (2009).

(Continued)

*Primary Examiner* — Marsha Tsay
(74) *Attorney, Agent, or Firm* — MARSHALL, GERSTEIN & BORUN LLP

(57) ABSTRACT

Provided herein are cell free protein synthesis (CFPS) systems comprising a plurality of ribosomes attached to or encapsulated within a structure, or a plurality of structures, and, optionally, a solid support. Also provided are related kits and uses of the CFPS systems. Methods of producing a protein and methods of treating a disease are provided herein.

21 Claims, 29 Drawing Sheets
Specification includes a Sequence Listing.

(56) References Cited

OTHER PUBLICATIONS

Katranidis et al., Force measurements of the disruption of the nascent polypeptide chain from the ribosome by optical tweezers, FEBS Lett., 585(12):1859-1863 (2011).
Kempf et al., A Novel method to evaluate ribosomal performance in cell-free protein synthesis systems, Scientific Reports, 7:46753 (2017).
Khandurina et al., Microfabricated porous membrane structure for sample concentration and electrophoretic analysis, Anal. Chem., 71(9):1815-1819 (1999).
Kim et al., Electrokinetic protein preconcentration using a simple glass/poly(dimethylsiloxane) microfluidic chip, Anal. Chem., 78(14):4779-4785 (2006).
Kim et al., Structural basis for elastic mechanical properties of the DNA double helix., PLoS One, 11(4):e0153228 (2016).
Kohlheyer et al., Microfluidic high-resolution free-flow isoelectric focusing, Anal. Chem., 79(21):8190-8198 (2007).
Kovalenko et al., Macroporous carbon aerogel as a novel adsorbent for immobilized enzymes and a support for the lipase-active heterogeneous biocatalysts for conversion of triglycerides and fatty acids, J. Porous Mater, 25:1017-1026 (2018).
Kwok et al., Nanopore fabrication by controlled dielectric breakdown, PLoS One, 9(3):e92880 (2014).
Lapizco-Encinas et al., Protein manipulation with insulator-based dielectrophoresis and direct current electric fields, J. Chromatogr. A, 1206(1)45-51 (2008).
Liu et al., Organizing single-walled carbon nanotubes on gold using a wet chemical self-assembling technique, Langmuir, 16(8):3569-3573 (2000).
Liu et al., Stable singlewalled carbon nanotube-streptavidin complex for biorecognition, J. Phys. Chem. C, 114(10):4345-4352 (2010).
Lo et al., Fabrication of symmetric sub-5 nm nanopores using focused ion and electron beams, Nanotechnology, 17(13):3264 (2006).
Lteif et al., Insulin resistance, metabolic syndrome and vascular diseases: update on mechanistic linkages, Can. J. Cardiol. 20(suppl. B):66B-76B (2004).
Madani et al., Functionalization of single-walled carbon nanotubes and their binding to cancer cells, Int. J. Nanomedicine, 7:905-14 (2012).
Marbach et al., Iac operon induction in *Escherichia coli*: Systematic comparison of IPTG and TMG induction and influence of the transacetylase LacA, J. Biotechnol. 157(1):82-88 (2012).
Marques et al., Amine-modified Carbon Aerogels for CO2 Capture, Adsorption Science & Technology, 31:223-232 (2013).
McCormick et al., Microchannel electrophoretic separations of DNA in injection-molded plastic substrates, Anal. Chem., 69(14):2626-30 (1997).
Miller et al., The effects of DRIE operational parameters on vertically aligned micropillar arrays, Journal of Micromechanics and Microengineering, 23(3):035039 (2013).
Moller et al., Ratio of left ventricular peak E-wave velocity to flow propagation velocity assessed by color M-mode Doppler echocardiography in first myocardial infarction: prognostic and clinical implications, J. Am. Coll. Cardiol., 35:363-370 (2000).
Nierhaus et al., Mg2+, K+, and the ribosome, J. Bacteriol., 192(22):3817-3819 (2014).
Orelle et al., Protein synthesis by ribosomes with tethered subunits, Nature, 524:119-138 (2015).
Ozmen et al., Superfast responsive ionic hydrogels with controllable pore size, Polymer(Guildf)., 46(19):8119-8127 (2005).
Ren et al., Synthesis of large arrays of well-aligned carbon nanotubes on glass, Science, 282(5391):1105-7 (1998).
Roberts et al., UV laser machined polymer substrates for the development of microdiagnostic systems, Anal. Chem., 69(11):2035-2042 (1997).
Rosenblum et al., Engine out of the chassis: cell-free protein synthesis and its uses, FEBS Lett., 588(2):261-268 (2014).
Rothemund et al., Design and characterization of programmable DNA nanotubes, J. Am. Chem. Soc., 126(50):16344-16352 (2004).
Sawhney et al., Bioerodible hydrogels based on photopolymerized poly(ethylene glycol)-co-poly(.alpha.-hydroxy acid) diacrylate macromers, Macromolecules, 26:581-587 (1993).
Shankles et al., Fabrication of nanoporous membranes for tuning microbial interactions and biochemical reactions, J. Vac. Sci. Technol. B, 33(2015):6-3 (2015).
Shim et al., Functionalization of carbon nanotubes for biocompatibility and biomolecular recognition, Nano Lett., 2(4):285-288 (2002).
Shimizu et al., Cell-free translation reconstituted with purified components., Nat. Biotechnol., 19(8):751-5 (2001).
Siuti et al., Continuous protein production in nanoporous, picolitre vol. containers, Lab Chip, 11(20):3523-3529 (2011).
Siuti et al., Enzyme reactions in nanoporous, picoliter volume containers, Anal. Chem., 84(2):1092-1097 (2012).
Song et al., Microchip dialysis of proteins using in situ photopatterned nanoporous polymer membranes, Anal. Chem., 76(8):2367-2373 (2004).
Spirin et al., A Continuous cell-free translation system capable of producing polypeptides in high yield, Synthesis (Stuttg)., 242(4882):1162-1164 (1988).
Stadermann et al., Ultrafast gas chromatography on single-wall carbon nanotube stationary phases in microfabricated channels ultrafast gas chromatography on single-wall carbon nanotube stationary phases in microfabricated channels, Mech. Eng., 78(16):5639-5644 (2006).
Stapulionis et al., Fast in vitro translation system immobilized on a surface via specific biotinylation of the ribosome, Biol. Chem., 389(9):1239-1249 (2008).
Star et al., Noncovalent side-wall functionalization of single-walled carbon nanotubes, Macromolecules, 36(3):553-560 (2003).
Szymczak-Workman et al., Design and construction of 2A peptide-linked multicistronic vectors, Cold Spring Harb. Protoc., 2012(2):p. pdb.ip067876-pdb.ip067876 (2012).
Tamayol et al., Transverse permeability of fibrous porous media, Physical Review, E, 83:046314 (2011).
The Criteria Committee of the New York Heart Association, Nomenclature and Criteria for Diagnosis of Diseases of the Heart and Great Vessels, 9th ed. Boston, Mass: Little, Brown & Co; 253-256 (1994).
Timm et al., Toward microfluidic reactors for cell-free protein synthesis at the point-of-care, Small, 12(6):810:817 (2016).
Uemura et al., Single-molecule imaging of full protein synthesis by immobilized ribosomes, Nucleic Acids Research, 36(12):e70 (2008).
Vanzi et al., Protein synthesis by single ribosomes, RNA, 9(10):1174-1179 (2003).
Vasan et al., Prevalence, clinical features and prognosis of diastolic heart failure: an epidemiologic perspective, J. Am. Coll. Cardiol., 26:1565-1574 (1995).
Venkatesan et al., Highly sensitive, mechanically stable nanopore sensors for DNA analysis, Adv. Mater., 21(27):2771-2776 (2009).
Vieu et al., Electron beam lithography: resolution limits and applications, Appl. Surf. Sci., 164(1):111-117 (2000).
Wang et al., Fabrication of ultralong and electrically uniform single-walled carbon nanotubes on clean substrates, Nano Lett., 9(9):3137-3141 (2009).
Wang et al., Integration of immobilized trypsin bead beds for protein digestion within a microfluidic chip incorporating capillary electrophoresis separations and an electrospray mass spectrometry interface, Rapid Commun. Mass Spectrom., 14(15):1377-1383 (2000).
Washizu et al., Molecular dielectrophoresis of biopolymers, IEEE Trans. Ind. Appl., 30(4):835-843 (1994).
Watkins et al., Microfluidic CD4 + and CD8 + T lymphocyte counters for point-of-care HIV diagnostics using whole blood, Sci. Transl. Med., 5(214):214ra170 (2013).
Wayment et al., Controlling binding site densities on glass surfaces, Anal. Chem., 78(22):7841-7849 (2006).
Wruck et al., Translation and folding of single proteins in real time, PNAS, 114(22):E4399-E4407 (2017).
Xiao et al., PDMS micropillar-based microchip for efficient cancer cell capture, RSC Advances, 5:52161-52166 (2015).

(56) References Cited

OTHER PUBLICATIONS

Xie et al., Prognostic value of Doppler transmitral flow patterns in patients with congestive heart failure, J. Am. Coll. Cardiol., 24:132-139 (1994).

Yost et al., Layer-by-layer functionalized nanotube arrays: A versatile microfluidic platform for biodetection, Microsystems Nanoeng., 1:15037 (2015).

Yu et al., Direct attachment ofwellaligned single-walled carbon nanotube architectures to silicon (100) surfaces: a simple approach for device assembly, Phys. Chem. Chem. Phys., 9(4):510-520 (2007).

Yu, Strength and breaking mechanism of multiwalled carbon nanotubes under tensile load, Science, 287(5453):637-640 (2000).

Zhou et al., Simultaneous determination of nickel, cobalt and mercury ions in water samples by solid phase extraction using multiwalled carbon nanotubes as adsorbent after chelating with sodium diethyldithiocarbamate prior to high performance liquid chromatography, J. Chromatogr. A, 1360:76-81 (2014).

Zhu et al., Supercapacitors based on three-dimensional hierarchical graphene aerogels with periodic macropores, Nano. Lett., 16:3448-3456 (2016).

Zile et al., Heart failure with preserved ejection fraction: is this diastolic heart failure?, J. Am. Coll. Cardiol., 41:1519-1522 (2003).

\* cited by examiner

FIGURE 3A
FIGURE 3B
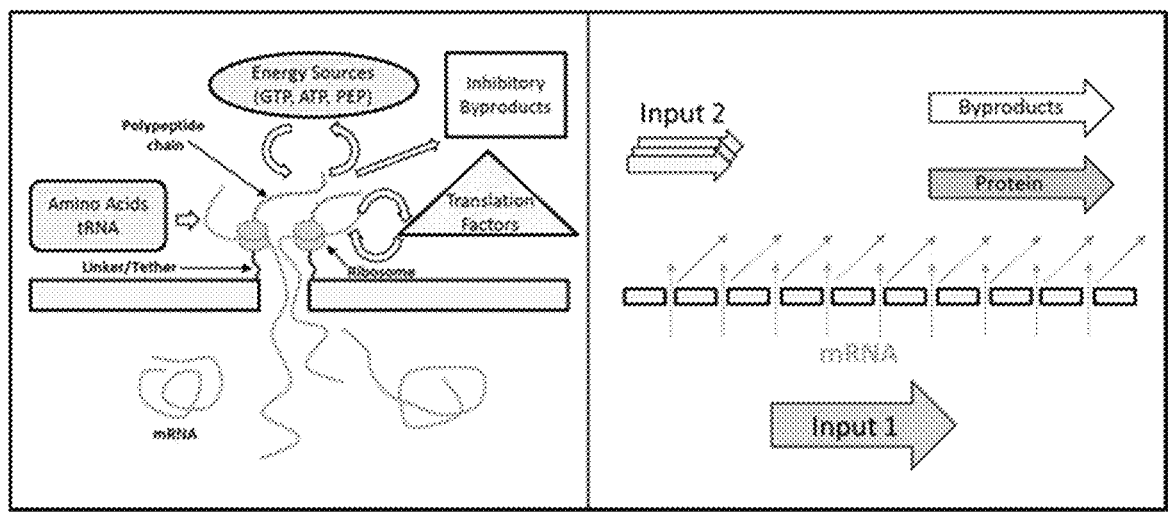
FIGURE 4
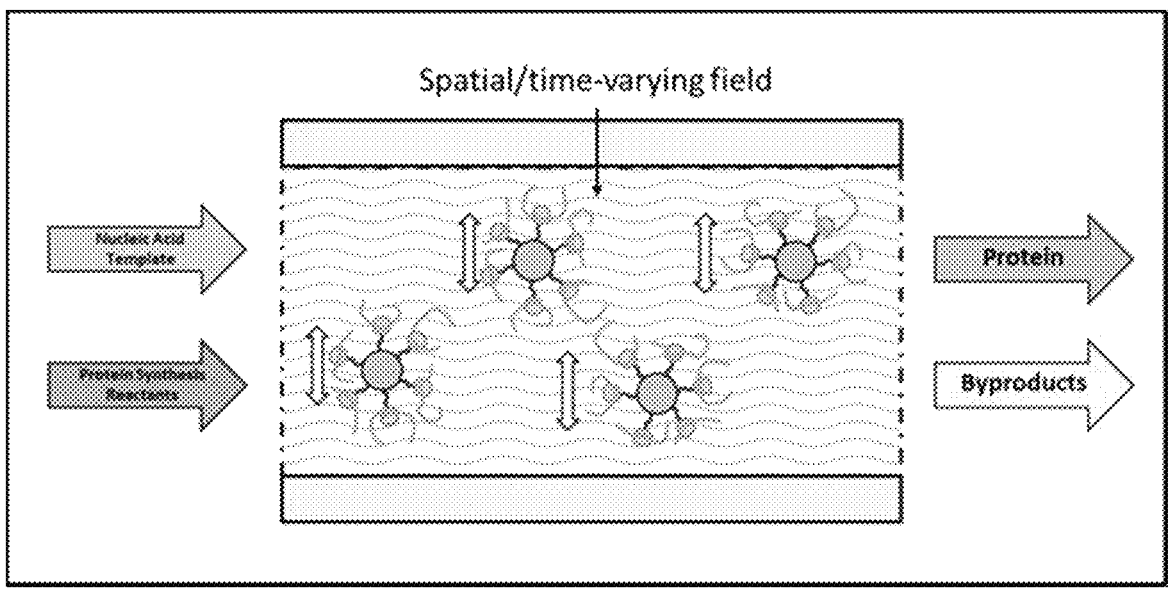

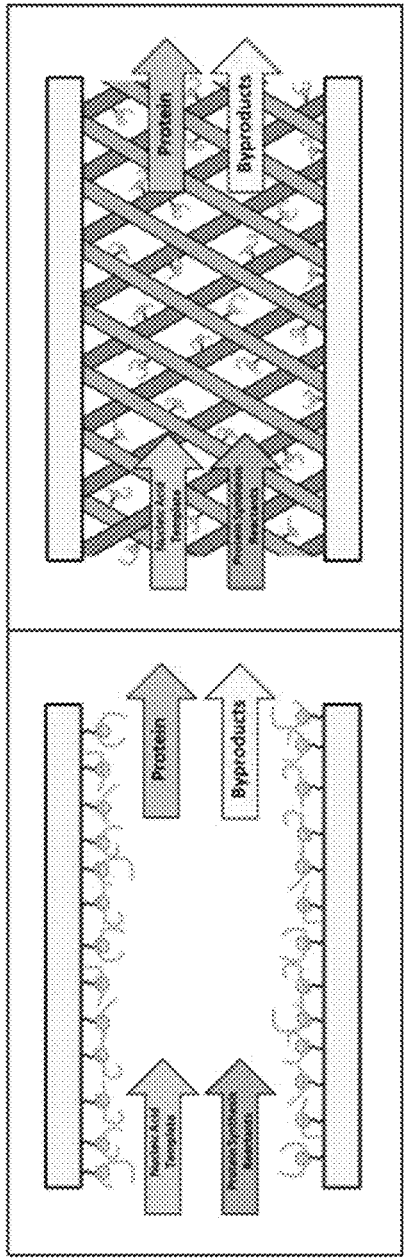
FIGURE 5A
FIGURE 5B
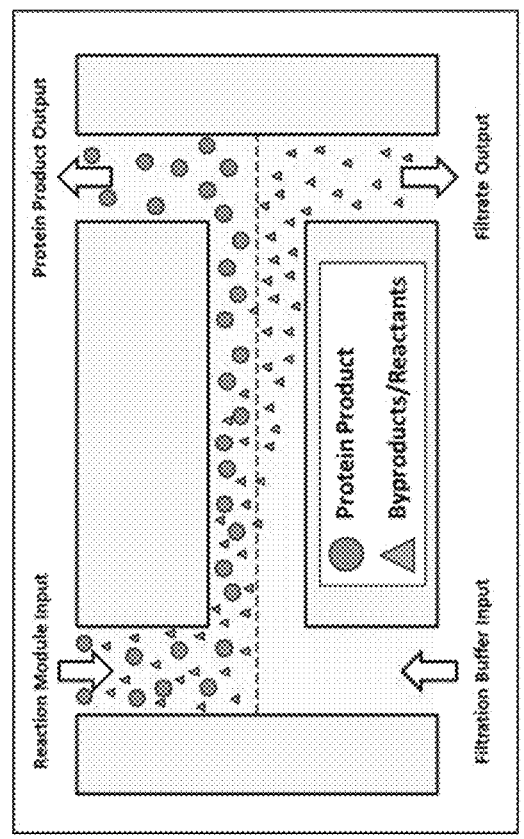
FIGURE 6

FIGURE 7a
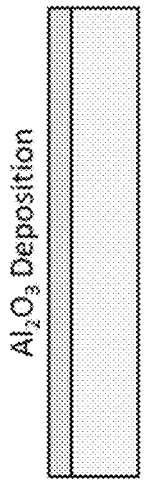
FIGURE 7b
FIGURE 7c
FIGURE 7d
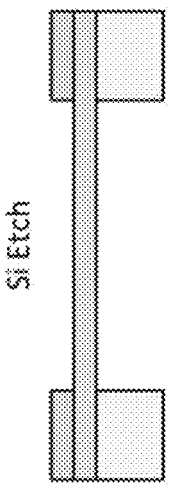
FIGURE 7e
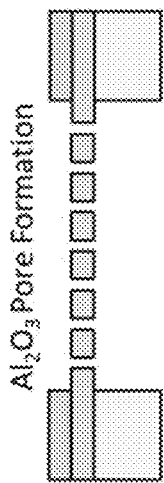
FIGURE 7f
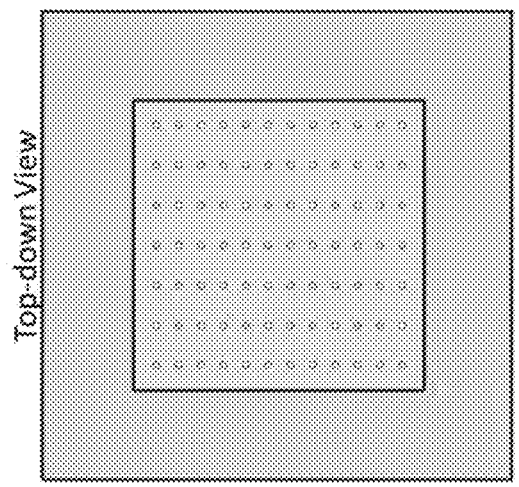
FIGURE 7g

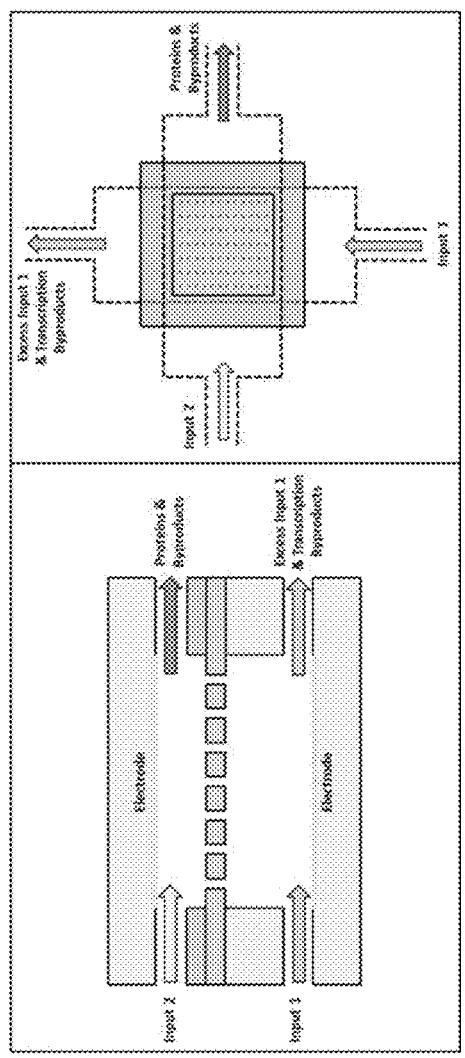
FIGURE 8b
FIGURE 8a
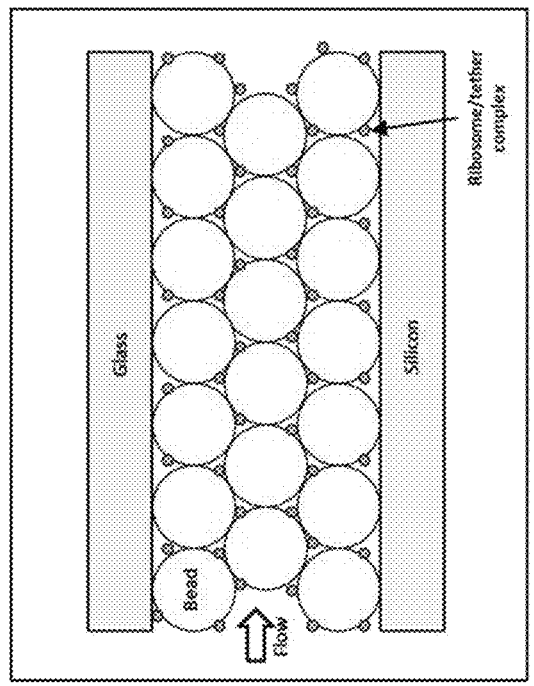
FIGURE 10
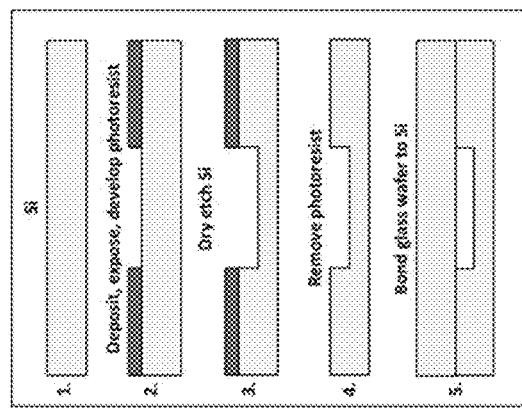
FIGURE 9

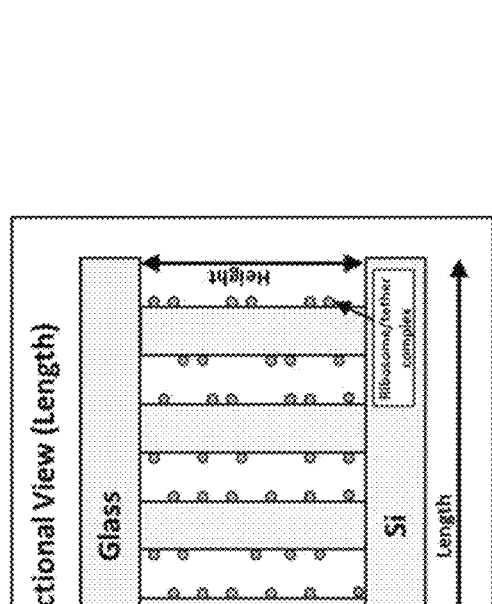
FIGURE 11a
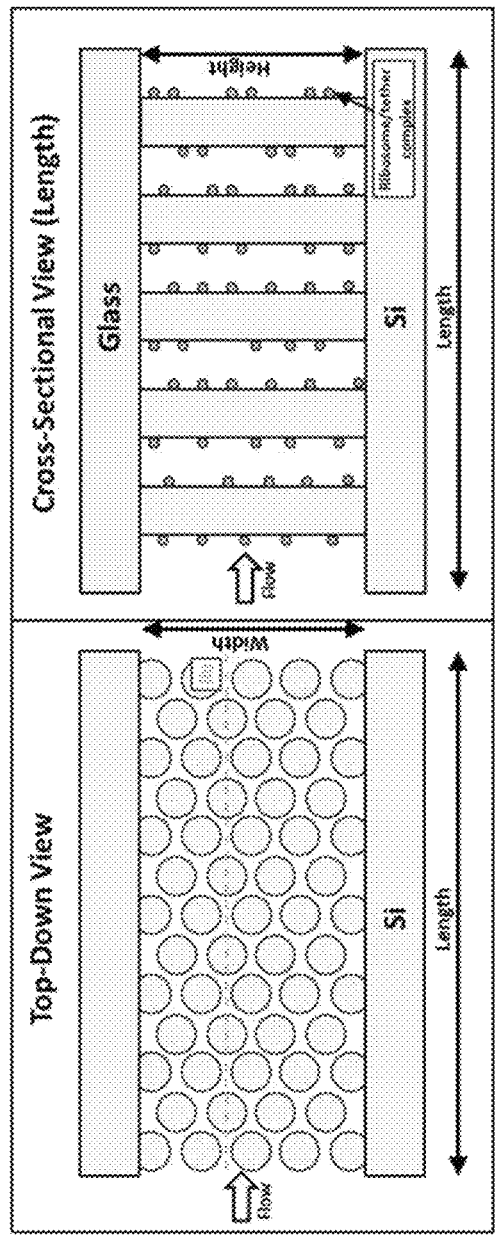
FIGURE 11b
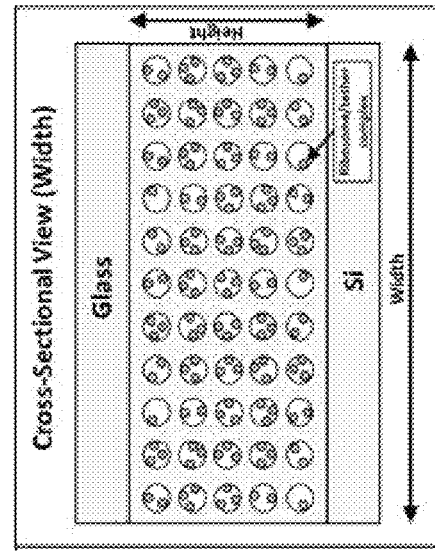
FIGURE 12A
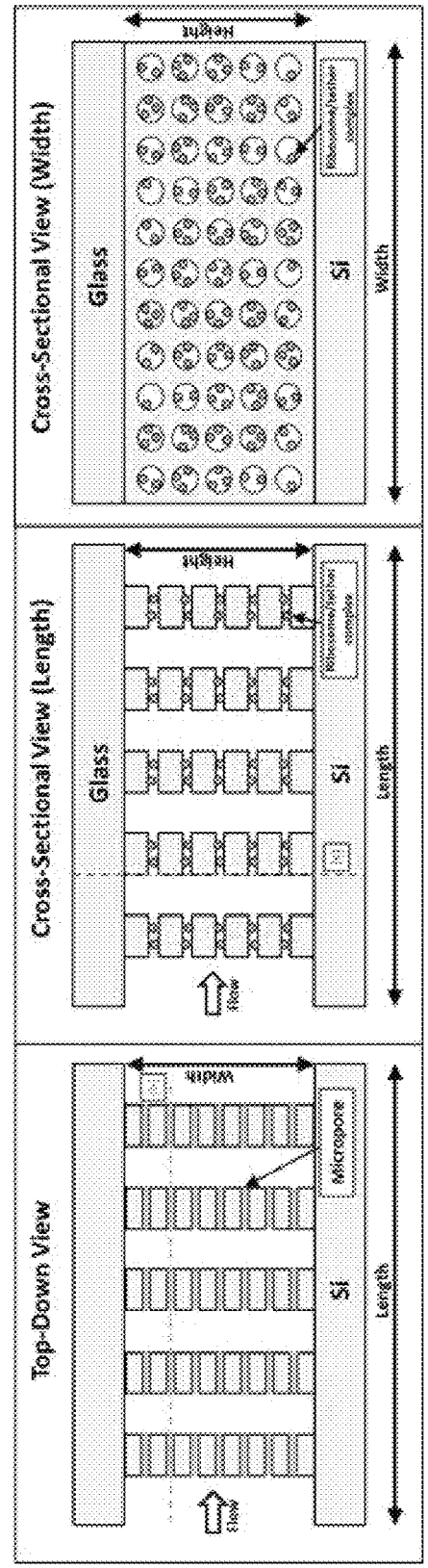
FIGURE 12B
FIGURE 12C Western blot signal: mCherry Ab + fluorescent secondary Ab
3 Day Bead-Ribo Incubation Figure 19
First Series
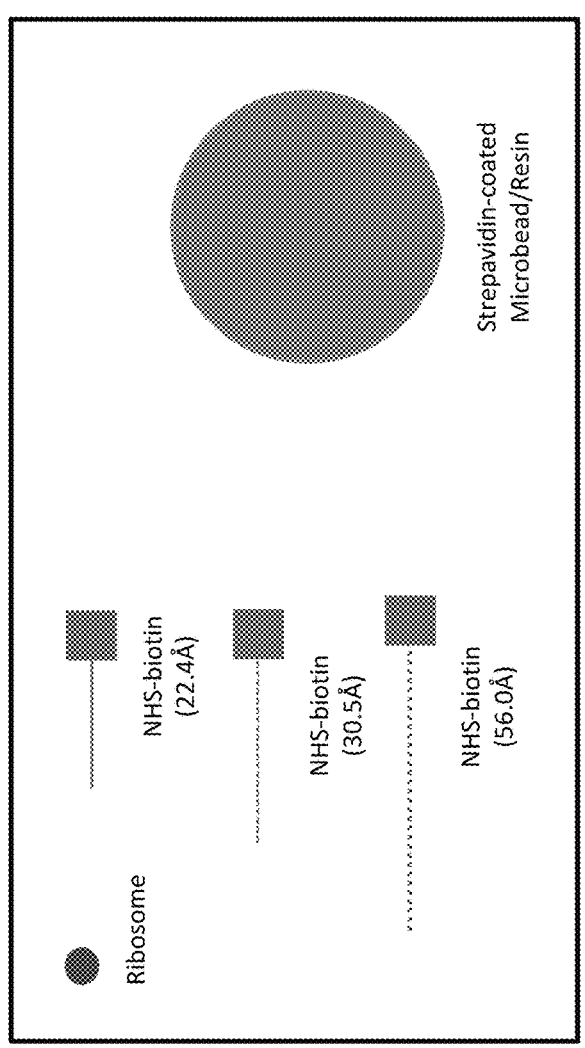
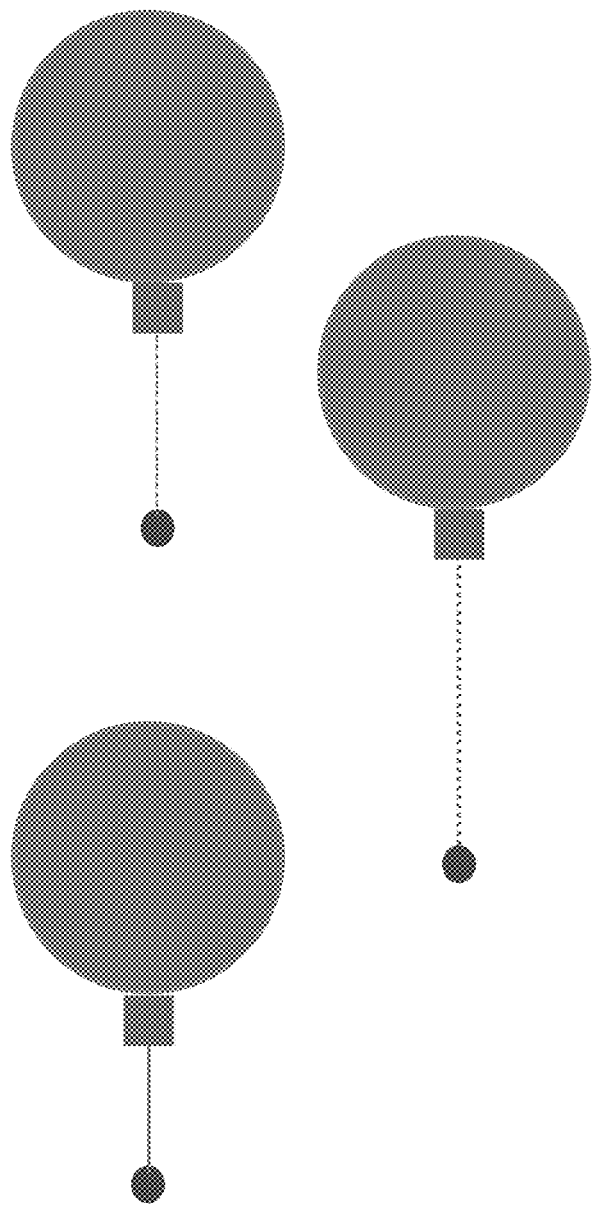

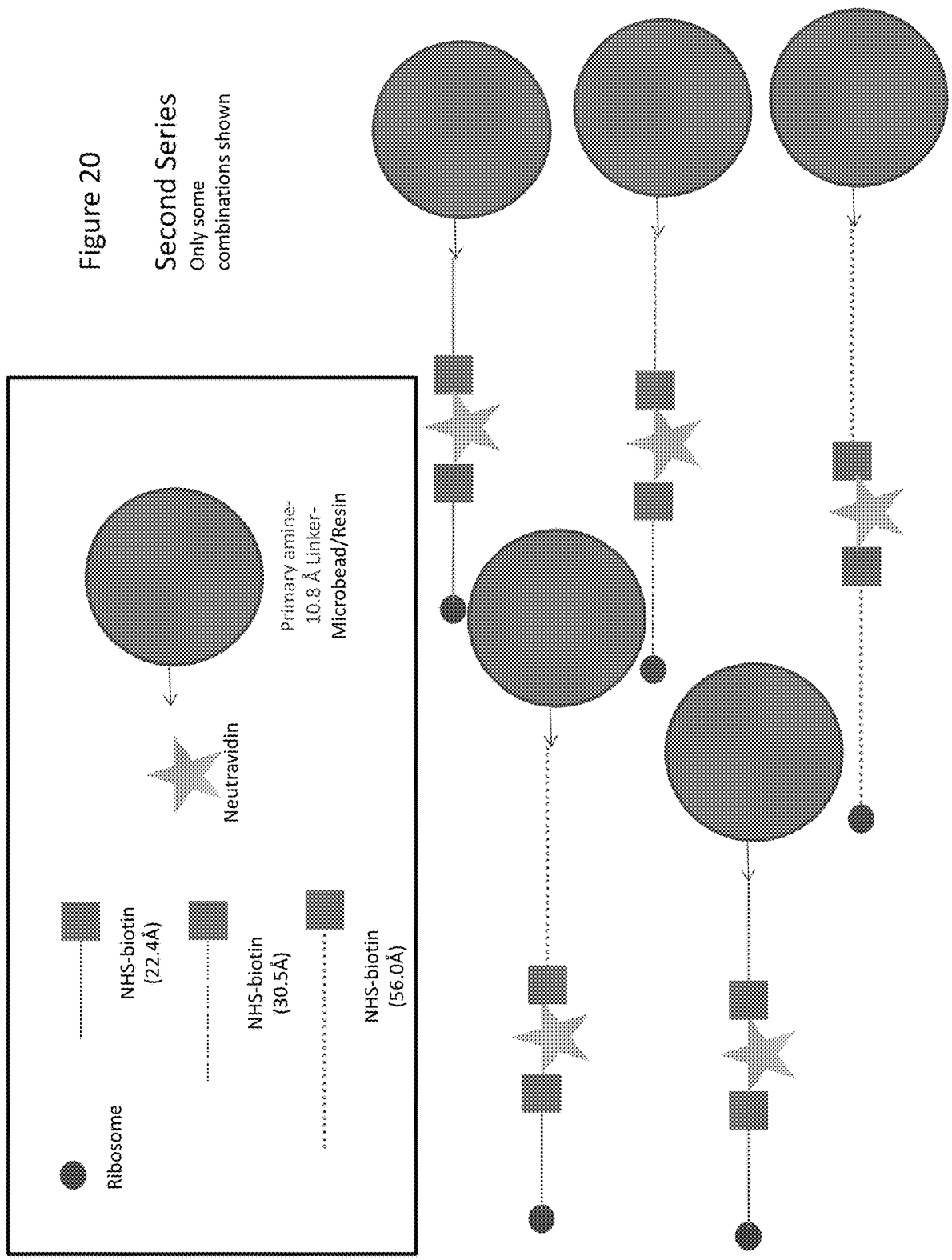

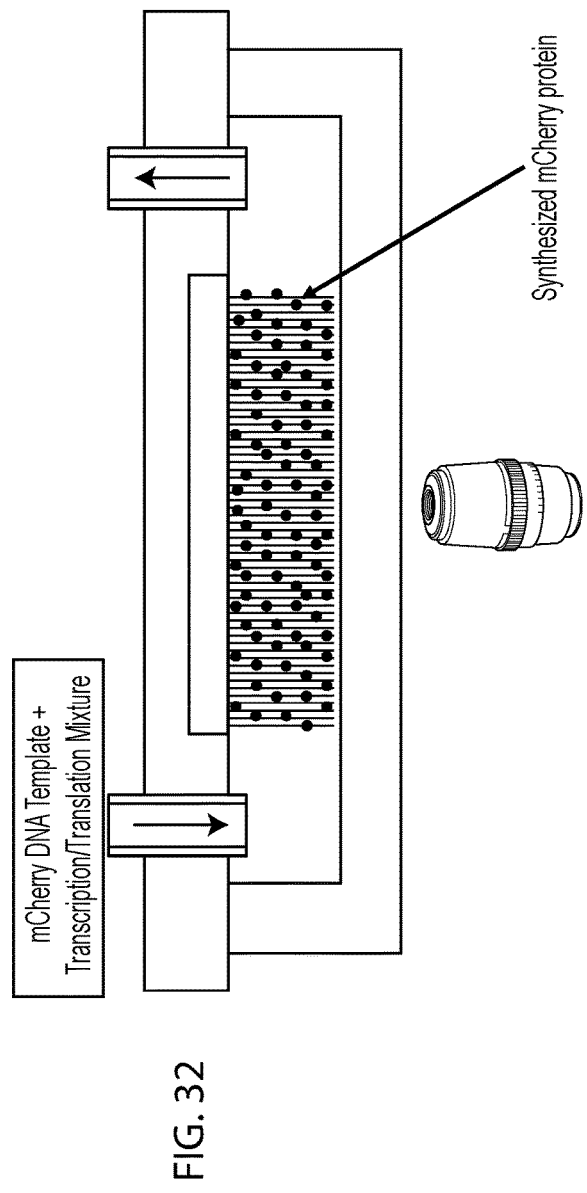

FIG. 32

| Technology | Product/hr (mg) | Reaction Chamber Volume (μL) | Product/ hr per μL Chamber Volume (mg) | Aerogel rate per uL / other technology rate per uL | Reaction Chamber Footprint (cm²) |
|---|---|---|---|---|---|
| Aerogel lattice | 49.9 | 20 | $2.5 \times 10^{0}$ | 1 | 0.5 |
| CNT lattice | 2.25 | 5 | $4.5 \times 10^{-1}$ | 6 | 1 |
| Micropillar lattice | 0.07 | 5 | $1.4 \times 10^{-2}$ | 183 | 1 |
| Latest research [9] | 0.25 | 50 | $5.0 \times 10^{-3}$ | 499 | ~20 |
| Industry standard | $1.25 \times 10^{4}$ | $1.2 \times 10^{10}$ | $1.0 \times 10^{-6}$ | $2.5 \times 10^{6}$ | $3.1 \times 10^{4}$ |

Table: Estimated protein production rates and sizes of proposed technology vs latest research in miniaturized CFPS. Alternative methods using CNTs and micropillars instead as ribosome scaffolds is shown as a reference. The ratio of rates is calculated from dividing aerogel rate per μL by the rate per μL for the other technologies. For aerogel, CNT, and micropillar lattices, assuming ribosome translation rate of 21 amino acids per second.

FIG. 33

CELL-FREE PROTEIN SYNTHESIS SYSTEMS

CROSS REFERENCE TO RELATED APPLICATIONS

This application claims priority to U.S. Provisional Application No. 62/796,427, filed Jan. 24, 2019, the entire contents of which is incorporated herein by reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 801 byte ASCII (Text) file named "53495A_Seqlisting.txt"; created on Jan. 22, 2020.

BACKGROUND

In the healthcare sector, there is a crucial need for the rapid and portable manufacture of proteins, e.g., therapeutic proteins. The ability to quickly produce targeted proteins for therapeutics and vaccines to stop or slow infection before it propagates would greatly reduce the susceptibility to future pandemics. The rapid production of a personalized medicine would improve a patient's prognosis by reducing the time between the onset of symptoms and therapy. A point-of-care system would reduce new infections by minimizing the relocation of infected patients, and also would transfer the capability of custom therapeutics from centralized factories to flexible and nimble platforms in hospitals, clinics, and even the bedside. Pharmaceutical companies desire a small-quantity, quick turnaround protein manufacturing capability during their precision medicine patient trials, which currently suffer delays of 4 to 6 months in the creation of the personalized drugs (personal communication).

The current industry standard for mass protein synthesis consists of large, labor-intensive facilities where genetically-modified cells are cultured to create desired proteins. This in vivo protein production model—which takes on the order of months to produce a new drug lot—cannot be scaled down into reactors that would generate practical amounts of protein for point-of-care therapeutics or low-latency patient trials. Other drawbacks include decreased production and yield from unwanted genetic mutations during culturing and a limited product scope since some proteins may be unstable and/or toxic to the cells that are creating them [Spirin et al., Synthesis (Stuttg) 242(4882): 1162-1164 (1988)].

Cell-free protein synthesis (CFPS) methods have streamlined and simplified the process by replacing cells with only the necessary components to translate proteins from messenger RNA (mRNA), creating a larger variety of purified protein products that could not otherwise be made in a cellular system [Shimizu et al., *Nat. Biotechnol*, 19(8): 751-755 (2001); Rosenblum and Cooperman, FEBS Letters 588(2): 261-268 (2014)]. CFPS systems can be scaled down to more portable formats, as some have shown [Siuti et al., Anal. Chem. 84(2): 1092-1097 (2012); Timm et al., *Small* 6: 810-817 (2015)]. However, even the most advanced miniaturized technology to date produces only single doses of up to 2 mg in 8 hours [Timm et al., 2015, supra]. This is still impractical for point-of-care therapeutic systems and biopharmaceutical applications that may need to produce on the order of grams of various proteins per day.

SUMMARY

Provided herein for the first time are data which demonstrate the design and manufacture of a variety cell free protein synthesis (CFPS) systems comprising localized ribosomes on structures, wherein the ribosomes may be repeatedly used in in vitro translation (IVT) reactions to produce proteins. Without being bound to any particular theory, the CFPS systems described herein are capable of synthesizing proteins at rates per reaction chamber volume of several orders of magnitude higher than those described in the art, including cell-based methods and cell-free methods. Advantageously, the CFPS systems provided herein are characterized by a large surface-to-volume ratio which maximizes the surface area available for biomolecular interactions between the components of the IVT reactions, e.g., ribosomes, translation mixture, and mRNA. Also, the CFPS systems provided herein may be run in a continual fashion, such that the IVT reaction products (e.g., synthesized proteins) and inhibitory reaction byproducts are continuously collected or washed away, optionally, for downstream processing, and replaced by fresh consumables so that the IVT reactions may be repeated with the same high density array of ribosomes at high reaction rates.

Accordingly, the present disclosure provides a CFPS system comprising a plurality of ribosomes attached to or encapsulated within a structure, or a plurality of structures.

In exemplary embodiments, the CFPS system comprises a solid support, a plurality of structures, and a plurality of ribosomes, wherein each structure is attached to a plurality of ribosomes, optionally, wherein each ribosome is attached to the structure through a linker. In exemplary aspects, the CFPS system comprises at least one fluidic inlet and at least one fluidic outlet and the plurality of structures is positioned between the at least one fluidic inlet and at least one fluidic outlet. In various aspects, each structure is spherical in shape. For example, each structure is a bead, and, in various aspects, the beads are not attached to the solid support. Optionally, the solid support comprises a tube, a column, or a chip comprising a chamber, which contains or holds the beads.

In exemplary instances, each structure is cylindrical in shape. For example, each structure is a micropillar or a nanotube, and in various instances, the micropillars or nanotubes are attached to the solid support. Optionally, the solid support comprises a chip or a bead to which the micropillars or nanotubes are attached.

In exemplary aspects—the structure is a lattice and a plurality of ribosomes are attached to the lattice. In exemplary aspects, the lattice comprises a weave of nanostrips, nanostrings, nanothreads and/or nanowires. Optionally, each ribosome is attached to the lattice through a linker.

In exemplary instances, the structure is an aerogel, foam, or sponge. Optionally, the aerogel is a graphene aerogel.

In exemplary instances, the ribosomes are encapsulated within a structure, e.g., a structure comprising a polymer, hydrogel or gelatin. The ribosomes in some aspects are suspended throughout the structure.

A kit comprising a presently disclosed CFPS system is also provided herein. In exemplary embodiments, the kit comprises a CFPS system of the present disclosure and one or more of: a transfer RNA (tRNA), an amino acid, an enzymatic cofactor, and an energy source.

Further provided herein are uses of the presently disclosed CFPS system. The present disclosure provides in exemplary embodiments the use of the presently disclosed CFPS system in a method for in vitro protein synthesis.

The present disclosure additionally provides a method of producing a protein. In exemplary embodiments, the method comprises contacting one or more solutions comprising one or more in vitro translation reagents with the plurality of ribosomes of the presently disclosed CFPS system.

A method of treating a disease in a patient is provided by the present disclosure. In exemplary embodiments, the method comprises administering a therapeutic protein to the patient in an amount effective to treat the disease, wherein the therapeutic protein was produced according to a presently disclosed method of producing a protein.

BRIEF DESCRIPTION OF THE DRAWINGS

FIG. 3A is an illustration depicting protein synthesis at a pore.

FIG. 3B is an illustration depicting porous membrane flow. It is envisioned that multiple ribosomes or ribosomal subunits may be attached to each tether.

FIG. 4 is an illustration depicting particle-ribosome complexes which may be manipulated by various fields to optimize reaction kinetics while localizing ribosomal machinery.

FIG. 5A is an illustration depicting ribosome subunits or particle-ribosome complexes attached to walls of a reaction module.

FIG. 5B is an illustration depicting ribosome subunits or particle-ribosome complexes attached to a matrix inside the module.

FIG. 6 is an illustration depicting an H-filter design to filter out the smaller reactants and byproducts from the larger target protein product. Multiple stages can be used to improve efficiency.

FIG. 7 is an illustration depicting a fabrication process to create porous membrane in reaction module. A silicon (Si) wafer (FIG. 7A) is coated with aluminum oxide ($Al_2O_3$) (FIG. 7B) followed by silicon nitride (SiN)(FIG. 7C). The nitride (FIG. 7D) and silicon (FIG. 7E) are etched to create the membrane, which then is modified to create an array of micro/nanopores (FIG. 7F). Inset (FIG. 7G) shows a top-down view of the array of pores.

FIG. 8 is an illustration depicting a cross-sectional view (FIG. 8a) and top-down view (FIG. 8b) of completed reaction module using one of many possible microfabrication techniques.

FIG. 9 is an illustration depicting exemplary microfabrication steps to create simpler reaction chamber design using standard photolithography processes.

FIG. 10 is an illustration depicting a cross-sectional view of lattice created by bead packing.

FIG. 11 is an illustration depicting top-down (FIG. 11a) and cross-sectional (FIG. 11b) views of an array of pillars that simulates a lattice. In this example, the pillars are etched out of the silicon (Si) substrate before sealing the chamber with a glass lid.

FIG. 12 is an illustration depicting top-down (FIG. 12a) and cross-sectional (FIG. 12b and FIG. 12c) views of a series of membrane walls. In FIG. 12a, the shaded regions represent micropore locations that would be hidden from view by the top of the wall.

FIG. 19 is an illustration of different biotin molecules having varying length spacer arms and their use in attaching ribosomes to microbeads/resin.

FIG. 20 an illustration of different biotin molecules having varying length spacer arms and their use in attaching ribosomes to microbeads/resin having a 10.8 angstrom spacer arm terminating with a primary amine via neutravidin molecules.

FIG. 32 is an illustration of how mCherry DNA template and transcription and translation reagents are introduced into a CFPS system comprising either nanotubes or micropillars (as shown in FIGS. 28-31) to produce mCherry fluorescent protein, which may be detected via microscopy.

FIG. 33 is a table of estimated protein production rates and sizes.

DETAILED DESCRIPTION

CFPS System

Figure 1:
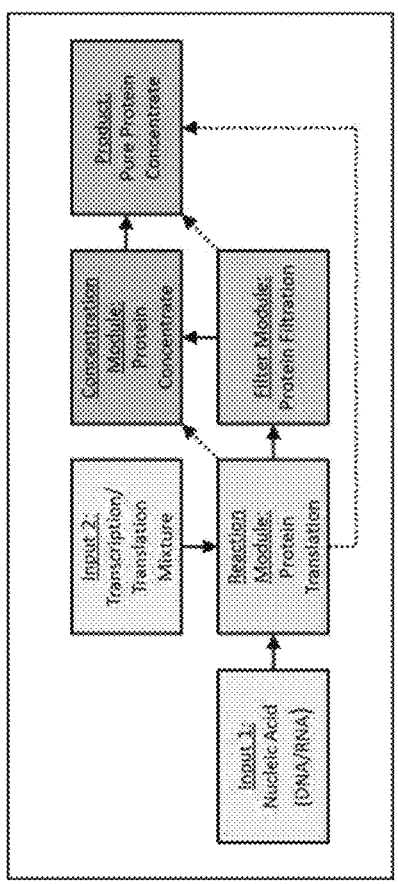
FIG. 1 is a schematic of the process flow.

The present disclosure provides a cell free protein synthesis (CFPS) system comprising a plurality of ribosomes attached to or encapsulated within a structure, or a plurality thereof. In exemplary embodiments, the CFPS system comprises a solid support, a plurality of structures, and a plurality of ribosomes, wherein each structure is attached to a plurality of ribosomes. In various aspects, the structures are not attached to the solid support. For instance, in some aspects, the solid support holds, houses, or contains the structures. In exemplary aspects, each structure is spherical in shape. For example, each structure is a bead, and, in various aspects, the beads are not attached to the solid support. In various instances, the structure is a granule, e.g., an aerogel granule, such as those described in Kovalenko et al., J. Porous Mater., 25:1017-1026 (2018). Optionally, the solid support comprises a vessel, a tank, a tube, a column, or a chip comprising a chamber, which holds, houses, or contains the beads. In various aspects, the structures are attached to the solid support. For instance, in some aspects, the structures are covalently bonded to the solid support. In other aspects, the structures are bonded to the solid support through non-covalent interactions, e.g., van der Waals bonds, hydrogen bonds, hydrophobic, ionic, magnetic, electrostatic, and like interactions. In exemplary instances, each structure is cylindrical in shape. For example, each structure is a micropillar or a nanotube, and in various instances, the micropillars or nanotubes are attached to the solid support. Optionally, the solid support comprises a chip or a bead to which the micropillars or nanotubes are attached. In various aspects, the structures are attached to the solid support only under certain conditions. For instance, in some aspects, the structures are magnetic beads and, when a magnetic field is applied, the structures (e.g., magnetic beads) are attached to the solid support.

In exemplary embodiments, the CFPS system comprises a single structure, e.g., lattice, aerogel, foam, sponge, and a plurality of ribosomes is attached to the structure. In some aspects, the single structure is a lattice (e.g., mesh, weave). In some aspects, the lattice comprises multiple nanothreads, nanostrings, nanowires, or a combination thereof. In some aspects, the ribosomes are attached to the multiple nanothreads, nanostrings, nanowires, or a combination thereof, optionally through a linker. In some instances, the structure is an aerogel, foam or sponge. For instance, the aerogel may be a graphene aerogel, optionally a 3-dimensional (3-D) printed graphene aerogel.

In exemplary aspects, the CFPS system is designed for fluid to move through the structure, or plurality of structures, and, in exemplary instances, the movement of fluids through the CFPS system is cyclic. In exemplary aspects, the CFPS system comprises at least one inlet and at least one outlet through which fluids move, e.g., a fluidic inlet, a fluidic outlet. In some aspects, the inlet and outlet permit the movement of fluids but do not permit the movement of structures due to e.g., size restriction. In various aspects, the plurality of structures is positioned between the at least one fluidic inlet and at least one fluidic outlet. In some aspects, the CFPS system is designed for microfluidics and the CFPS system comprises at least one microfluidic inlet and at least one microfluidic outlet. In exemplary aspects, the CFPS system comprises a pump which controls the speed and/or direction of fluidic movement. In exemplary instances, the CFPS system does not comprise a pump. In some aspects, fluid moves through the CFPS system due to applied forces (vis-a-vis, e.g., shaking, rocking, tumbling, by e.g., vortexing, sonicating, spinning) or due to gravitational forces.

Additional and alternative embodiments and aspects of the presently disclosed CFPS systems are discussed below.

Structures

The structures may comprise any one of a variety of geometries. Preferably, the shape of the structure is one that has a large surface area for the attachment of the plurality of ribosomes. In some aspects, the structure has a substantially flat surface for ribosome attachment. In alternative aspects, the structure has a rounded surface for ribosome attachment. For instance, the structure may be spherical or cylindrical and the structure optionally is a bead, tube, pillar, column, string, wire, or thread. In some aspects, the structures can be as small as and irregularly-shaped as a single molecule (e.g., iron oxide tag that allows a single ribosome to be manipulated by a magnetic field). In alternative aspects, the structure may be substantially flat.

The structures may be made of any suitable, non-toxic, chemically-inert material. In exemplary instances, the structure is made of plastic, glass, silica, carbon, a carbon-based material (e.g., graphene), or a combination thereof. In exemplary aspects, the structure is made of a polymer. The polymer may be branched or unbranched. The polymer may be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). The average molecular weight of the polymer is in some aspect between about 5 kDa and about 50 kDa, between about 12 kDa to about 40 kDa or between about 20 kDa to about 35 kDa. In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene. Additionally, in some aspects, the polymer is a mixture of polymers, e.g., a co-polymer, a block co-polymer. In some instances, the polymer is a polysiloxane, e.g., polydimethylsiloxane (PDMS).

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion. In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). In some embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In some aspects, the water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C 10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

Structures: Beads

In some aspects, the structures are beads and optionally the beads are not attached to the solid support of the CFPS system or not attached to the solid support of the CFPS system under certain conditions. Optionally, the average bead size is about 10 nm to about 1 mm (e.g., about 10 nm to about 1 µm or about 1 µm to about 1 mm). For instance, the average bead size of the beads is about 10 nm to about 1 µm (e.g., about 10 nm to about 900 nm, about 10 nm to about 800 nm, about 10 nm to about 700 nm, about 10 nm to about 600 nm, about 10 nm to about 500 nm, about 10 nm to about 400 nm, about 10 nm to about 300 nm, about 10 nm to about 200 nm, about 10 nm to about 100 nm, about 100 nm to about 1 µm, about 200 nm to about 1 µm, about 300 nm to about 1 µm, about 400 nm to about 1 µm, about 500 nm to about 1 µm, about 600 nm to about 1 µm, about 700 nm to about 1 µm, about 800 nm to about 1 µm, about 900 nm to about 1 µm) in diameter. In exemplary aspects, the average bead size of the beads is about 1 µm to about 1 mm (e.g., about 1 µm to about 900 µm, about 1 µm to about 800 µm, about 1 µm to about 700 µm, about 1 µm to about 600 µm, about 1 µm to about 500 µm, about 1 µm to about 400 µm, about 1 µm to about 300 µm, about 1 µm to about 200 µm, about 1 µm to about 100 µm, about 200 µm to about 1 mm, about 300 µm to about 1 mm, about 400 µm to about 1 mm, about 500 µm to about 1 mm, about 600 µm to about 1 mm, about 700 µm to about 1 mm, about 800 µm to about 1 mm, about 900 µm to about 1 mm) in diameter. In some aspects, the average bead size of the beads is about 20 µm to about 500 µm in diameter (e.g., about 30 µm to about 500 µm, about 40 µm to about 500 µm, about 50 µm to about 500 µm, about 60 µm to about 500 µm, about 70 µm to about 500 µm, about 80 µm to about 500 µm, about 90 µm to about 500 µm, about 100 µm to about 500 µm) or about 40 µm to about 200 µm in diameter, about 50 µm to about 150 µm in diameter, about 70 µm to about 100 µm in diameter.

In some aspects, the beads are less than 500 nm in diameter or less than about 250 nm. In exemplary aspects, the beads are less than 100 nm. Optionally, the beads are about 1 nm to about 250 nm or about 1 nm to about 200 nm or about 1 nm to about 150 nm or about 1 nm to about 100 nm. In various aspects, the beads are at least about 1 nm in diameter and less than about 100 nm in diameter, e.g., the diameter of the bead is less than about 90 nm, less than about 80 nm, less than about 70 nm, less than about 60 nm, less than about 50 nm, less than about 40 nm, less than about 30 nm, less than about 20 nm, or less than about 10 nm. In various instances, the bead is about the same size as the ribosome and the ratio of ribosome:bead is about 1:1. In various aspects, a 1:1 ratio of ribosome:bead minimizes steric hindrance, but also ensures maximum mobility and activity similar to that of a free-floating ribosome. In various aspects, the ribosome mobility is inversely proportional to size and can be reused for future protein synthesis reactions (e.g., via magnetic manipulation).

In exemplary aspects, each bead has an average surface area of about 300 $nm^2$ to about 4 $mm^2$. In some aspects, each bead has an average surface area of about 300 $nm^2$ to about 10 $mm^2$ or about 300 $nm^2$ to about 1 $mm^2$ µm or about 300 $nm^2$ to about 100 $µm^2$ or about 300 $nm^2$ to about 10 $µm^2$ or about 300 $nm^2$ to about 1 $µm^2$ or about 300 $nm^2$ to about 900 $nm^2$. In some aspects, each bead has an average surface area of about 900 $nm^2$ to about 4 $mm^2$ or about 1 $µm^2$ to about 4 $mm^2$ or about 10 $µm^2$ to about 4 $mm^2$ or about 100 $µm^2$ to about 4 $mm^2$ or about 1 $mm^2$ to about 4 $mm^2$ or about 10 $mm^2$ to about 4 $mm^2$.

In exemplary aspects, the surface area per volume of packed beads is about 3 $mm^2$ per µL to about $4×10^5$ $mm^2$ per µL. In some aspects, the surface area per volume of packed beads is about 10 $mm^2$ per µL to about $4×10^5$ $mm^2$ per µL, about 50 $mm^2$ per µL to about $4×10^5$ $mm^2$ per µL, about 100 $mm^2$ per µL to about $4×10^5$ $mm^2$ per µL, about 1 $m^2$ per µL to about 400 $m^2$ per µL, about 10 $m^2$ per µL to about 400 $m^2$ per µL, about 100 $m^2$ per µL to about 400 $m^2$ per µL, about 200 $m^2$ per µL to about 400 $m^2$ per µL, about 300 $m^2$ per µL to about 400 $m^2$ per µL, or about 3 $mm^2$ per µL to about 300 $m^2$ per µL, about 3 $mm^2$ per µL to about 200 $m^2$ per µL, about 3 $mm^2$ per µL to about 100 $m^2$ per µL, about 3 $mm^2$ per µL to about 10 $m^2$ per µL, about 3 $mm^2$ per µL to about 1 $m^2$ per µL, about 3 $mm^2$ per µL to about 100 $mm^2$ per µL, about 3 $mm^2$ per µL to about 50 $mm^2$ per µL, or about 3 $mm^2$ per µL to about 10 $mm^2$ per µL.

In exemplary aspects, the plurality of structures (e.g., beads) of the CFPS system are approximately the same size. For example, the diameter of the beads vary by less than about 50%. In some instances, the diameter of the beads vary by less than about 40%, less than about 30%, less than about 25%, less than about 20%, less than about 15%, less than about 10%, or less than about 5%). In some aspects, the beads are uniform in size. In some aspects, the structures (e.g., beads) vary in diameter by about 50% or more. In some instances, the diameter of the beads vary by more than about 60%, more than about 70%, more than about 80%, more than about 90% or more than 100%.

In various aspects, the beads are packed in a solid support, e.g., a chromatographic column, a chamber of a chip. In such instances, the gaps between the beads is determined by bead diameter (or diameters if plurality of different bead sizes) and bead packing configurations. The beads in some aspects are not packed and are loosely distributed throughout the solid support. For instance, the bead may be encapsulated in a hydrogel, gelatin, or polymer. In such instances, the distance between the beads is greater than the diameter of the bead.

Structures: Pillars

In exemplary aspects, the structures of the CFPS system are pillars, e.g., micropillars, nanopillars. As used herein, a "nanopillar" refers to a cylindrical structure having a diameter that is less than 1 micron, and a "micropillar" refers to a cylindrical structure having a diameter of about 1 micron or higher. In various aspects, the pillars are made of silicon optionally produced by micromachining, 3-D printing or a combination thereof. In some aspects, the micropillars are about 1 μm to about 100 μm in diameter (e.g., about 5 μm to about 100 μm, about 10 μm to about 100 μm, 20 μm to about 100 μm, 30 μm to about 100 μm, 40 μm to about 100 μm, 50 μm to about 100 μm, 60 μm to about 100 μm, 70 μm to about 100 μm, 80 μm to about 100 μm, 90 μm to about 100 μm, 5 μm to about 90 μm, 5 μm to about 80 μm, 5 μm to about 70 μm, 5 μm to about 60 μm, 5 μm to about 50 μm, 5 μm to about 40 μm, 5 μm to about 30 μm, 5 μm to about 20 μm, 5 μm to about 10 μm in diameter). Optionally, the micropillars are greater than or about 100 μm in height, optionally, greater than or about 200 μm, greater than or about 300 μm, greater than or about 400 μm, greater than or about 500 μm, greater than or about 600 μm, greater than or about 700 μm, greater than or about 800 μm, greater than or about 900 μm, or about 1 mm in height. In some aspects, the nanopillars range in diameter from below 50 nm (e.g., down to about 10 nm) and up to about 900 nm (e.g., 50 nm up to about 900 nm, 50 nm up to about 900 nm, 50 nm up to about 900 nm, 50 nm up to about 900 nm, 50 nm up to about 900 nm, 50 nm up to about 900 nm, 50 nm up to about 900 nm, 50 nm up to about 900 nm, 50 nm up to about 900 nm, 50 nm up to about 900 nm, 50 nm up to about 900 nm). Optionally, the nanopillars are about 5 μm to 50 μm in height (e.g., about 10 μm, about 20 μm, about 30 μm, about 40 μm, in height). In some instances, the pillars have an aspect ratio which is greater than or about 1, for instance, greater than or about 2, greater than or about 5, greater than or about 10, greater than or about 15, greater than or about 25, or greater than or about 30.

In exemplary aspects, the ratio of length to diameter for the nanopillars or micropillars is about 0.1 to about 150, e.g., about 0.5, about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150).

In exemplary aspects, the surface area per volume structure is about 1 mm$^2$ per μL to about 4×10$^4$ mm$^2$ per μL. For instance, in some aspects, the surface area per volume structure is about 10 mm$^2$ per μL to about 4×10$^4$ mm$^2$ per μL, about 100 mm$^2$ per μL to about 40 m$^2$ per μL, about 1 m$^2$ per μL to about 40 m$^2$ per μL, about 10 m$^2$ per μL to about 40 m$^2$ per μL, about 20 m$^2$ per μL to about 40 m$^2$ per μL, about 30 m$^2$ per μL to about 40 m$^2$ per μL, about 1 mm$^2$ per μL to about 30 m$^2$ per μL, about 1 mm$^2$ per μL to about 20 m$^2$ per μL, about 1 mm$^2$ per μL to about 10 m$^2$ per μL, about 1 mm$^2$ per μL to about 1 m$^2$ per μL, about 1 mm$^2$ per μL to about 100 mm$^2$ per μL, or about 1 mm$^2$ per μL to about 100 mm$^2$ per μL).

In some aspects, the spacing between the nanopillars or micropillars is about 5 nm to about 1 mm, about 10 nm to about 1 mm, about 50 nm to about 1 mm, about 100 nm to about 1 mm, about 250 nm to about 1 mm, about 500 nm to about 1 mm, about 750 nm to about 1 mm.

In exemplary aspects, the pillars of the CFPS system are approximately the same size. For example, the diameter and/or length of the pillars vary by less than about 50%. In some instances, the diameter and/or length of the pillars vary by less than about 40%, less than about 30%, less than about 25%, less than about 20%, less than about 15%, less than about 10%, or less than about 5%). In some aspects, the pillars are uniform in size. In some aspects, the pillars vary in diameter and/or length by about 50% or more. In some instances, the diameter and/or length of the pillars vary by more than about 60%, more than about 70%, more than about 80%, more than about 90% or more than 100%.

Structures: Nanotubes

In exemplary aspects, the structures of the CFPS system are tubes, e.g., microtubes, nanotubes. In various aspects, the nanotubes are made of carbon or a carbon-based material, e.g., graphene, or an inorganic material, e.g., a metal oxide. The nanotube may be single-walled, double-walled, triple-walled, or multi-walled. In some instances, the length:diameter ratio of the nanotubes may be about 0.1 to about 1×10$^7$. In various aspects, the length:diameter ratio of the nanotubes is at least about 1, 5, 10, or 25. In various instances, the length:diameter ratio of the nanotubes is greater than 50, 100, 500, or 1000. In some aspects, the length:diameter ratio of the nanotubes is greater than 10$^4$, 10$^5$, 10$^6$, or 10$^7$. In various aspects, the length is at least about 5 μm, at least about 10 μm, at least about 15 μm, at least about 20 μm, at least about 25 μm, at least about 30 μm, at least about 35 μm, at least about 40 μm, at least about 45 μm, at least about 50 μm, at least about 55 μm, at least about 60 μm, at least about 65 μm, at least about 70 μm, at least about 75 μm, at least about 80 μm, at least about 85 μm, at least about 90 μm, at least about 100 μm, at least about 500 μm, at least about 1 mm, or at least about 2 mm). In some aspects, the diameter of the nanotube is at least about 0.5 nm, about 1 nm, about 2 nm, about 3 nm, about 4 nm, about 5 nm, about 6 nm, about 7 nm, about 8 nm, about 9 nm, about 10 nm, at least about 25 nm, at least about 50 nm, at least about 75 nm, at least about 100 nm, at least about 125 nm, at least about 150 nm, at least about 175 nm, at least about 200 nm, at least about 250 nm, or at least about 300 nm. In various aspects, the length is ~15 μm and the diameter is approximately 200 nm±40 nm.

In exemplary aspects, the surface area per volume structure is about 50 mm$^2$ per μL to about 40,000 mm$^2$ per μL. In exemplary instances, the surface area per volume structure is about 100 mm$^2$ per μL to about 40,000 mm$^2$ per μL, 500 mm$^2$ per μL to about 40,000 mm$^2$ per μL, about 1 m$^2$ per μL to about 40 m$^2$ per μL, about 10 m$^2$ per μL to about 40 m$^2$ per μL, about 20 m$^2$ per μL to about 40 m$^2$ per μL, about 30 m$^2$ per μL to about 40 m$^2$ per μL, about 50 mm$^2$ per μL to about 30 m$^2$ per μL, about 50 mm$^2$ per μL to about 20 m$^2$ per μL, about 50 mm$^2$ per μL to about 10 m$^2$ per μL, about 50 mm$^2$ per μL to about 1 m$^2$ per μL, about 50 mm$^2$ per μL to about 500 mm$^2$ per μL, or about 50 mm$^2$ per μL to about 100 m$^2$ per μL.

In some aspects, the spacing between the nanotubes is about 0.5 nm to about 100 μm, about 1 nm to about 100 μm, about 10 nm to about 100 μm, about 100 nm to about 100 μm, about 1 μm to about 100 μm, about 10 μm to about 100 μm, about 50 μm to about 100 μm, about 0.5 nm to about 50 μm, about 0.5 nm to about 10 μm, about 0.5 nm to about 1 μm, about 0.5 nm to about 100 nm, about 0.5 nm to about 50 nm, or about 0.5 nm to about 10 μm.

In exemplary aspects, the nanotubes of the CFPS system are approximately the same size. For example, the diameter and/or length of the nanotubes vary by less than about 50%. In some instances, the diameter and/or length of the nanotubes vary by less than about 40%, less than about 30%, less than about 25%, less than about 20%, less than about 15%, less than about 10%, or less than about 5%). In some aspects, the nanotubes are uniform in size. In some aspects, the nanotubes vary in diameter and/or length by about 50% or more. In some instances, the diameter and/or length of the nanotubes vary by more than about 60%, more than about 70%, more than about 80%, more than about 90% or more than 100%.

Structures: Lattice

In exemplary aspects, the ribosomes of the CFPS system are attached to a lattice. In various instances, the lattice comprises a plurality of nanostrips, nanostrings, nanowires, or nanothreads. In various instances, the nanostrips, nanowires, nanostrings, or nanothreads are weaved together to form a lattice. In exemplary instances, the nanostrips, nanowires, nanostrings, or nanothreads are crossed and, optionally, fastened together, to form a lattice, e.g., the lattice is a structure consisting of strips of material crossed or fastened together with square or diamond-shaped spaces between.

In exemplary aspects, the surface area per volume structure is about 0.1 mm$^2$ per µL to about 10,000 mm$^2$ per µL, e.g., about 1 mm$^2$ per µL to about 10,000 mm$^2$ per µL, about 10 mm$^2$ per µL to about 10,000 mm$^2$ per µL, about 100 mm$^2$ per µL to about 10,000 mm$^2$ per µL, about 1 m$^2$ per µL to about 10 m$^2$ per µL, about 2.5 m$^2$ per µL to about 10 m$^2$ per µL, about 5 m$^2$ per µL to about 10 m$^2$ per µL, about 7.5 m$^2$ per µL to about 10 m$^2$ per µL, about 0.1 mm$^2$ per µL to about 7.5 m$^2$ per µL, about 0.1 mm$^2$ per µL to about 5 m$^2$ per µL, about 0.1 mm$^2$ per µL to about 2.5 m$^2$ per µL, about 0.1 mm$^2$ per µL to about 1 m$^2$ per µL, about 0.1 mm$^2$ per µL to about 100 mm$^2$ per µL, or about 0.1 mm$^2$ per µL to about 10 mm$^2$ per µL, or about 0.1 mm$^2$ per µL to about 1 mm$^2$ per µL.

Structures: Aerogel, Foam, Sponge

In some aspects, the structure is an aerogel, a foam, or a sponge. In certain instances, the structure is a graphene aerogel or graphene-based aerogel or a graphene foam or graphene-based foam. Graphene based aerogels and foams and methods of making the same are known in the art. See, e.g., Gorgolis and Galiotis, 2D Materials 4: 032001 (2017) and Chen et al., Environ Sci Technol (2019); doi: 10.102/acs.est.8b04642. In certain aspects, the graphene aerogel is made by hydrothermal reduction, chemical reduction, crosslinking, template-directed reduction, 3D printing—freeze drying, chemical reduction-hydrothermal processing. In some aspects, the graphene aerogel is made by a method known as projection micro-stereolithography. Additional methods include those described in, e.g., Hensleigh et al., Mater. Horiz. 5: 1035-1041 (2018) and Biener, et al., Adv. Mater., 24:5083-5087 (2012).

In some aspects, the surface area per unit structure volume is about 500 mm$^2$ per µL to about 200,000 mm$^2$ per µL (e.g., about 1000 mm$^2$ per µL to about 200,000 mm$^2$ per µL, about 5000 mm$^2$ per µL to about 200,000 mm$^2$ per µL, about 10000 mm$^2$ per µL to about 200,000 mm$^2$ per µL, about 50000 mm$^2$ per µL to about 200,000 mm$^2$ per µL, about 100000 mm$^2$ per µL to about 200,000 mm$^2$ per µL, about 150,000 mm$^2$ per µL to about 200,000 mm$^2$ per µL, about 500 mm$^2$ per µL to about 150,000 mm$^2$ per µL, about 500 mm$^2$ per µL to about 100,000 mm$^2$ per µL, about 500 mm$^2$ per µL to about 50,000 mm$^2$ per µL, about 500 mm$^2$ per µL to about 10,000 mm$^2$ per µL, about 500 mm$^2$ per µL to about 5,000 mm$^2$ per µL, or about 500 mm$^2$ per µL to about 1,000 mm$^2$ per µL).

In exemplary instances, the aerogel comprises pores. In various instances, at least some pores are from about 10 nm to about 20 µm (e.g., about 10 nm to about 10 µm about 10 nm to about 1 µm, about 10 nm to about 500 nm, about 10 nm to about 100 nm) in diameter.

Structures: Encapsulating Polymers, Hydrogels, Gelatins

In some aspects, the structure is a structure comprising polymer, hydrogel, or gelatin and the structure encapsulates the ribosomes. In some aspects, the structure is a xerogel. In some aspects, the polymer is any one of the polymers described herein. In some aspects, the structure has a surface area of about 1 mm$^2$ per µL to about 700,000 mm$^2$ per µL. For instance, the structure has a surface about 10 mm$^2$ per µL to about 700,000 mm$^2$ per µL, about 100 mm$^2$ per µL to about 700,000 mm$^2$ per µL, about 1 m$^2$ per µL to about 700,000 mm$^2$ per µL, about 10 m$^2$ per µL to about 700 m$^2$ per µL, or about 100 m$^2$ per µL to about 700 m$^2$ per µL.

Ribosomes, Ribosome Density, and Attachment

The CFPS systems of the present disclosure comprises a plurality of ribosomes, each comprising the small ribosomal subunit and the large ribosomal subunit. In aspects, the ribosomes are not mitochondrial ribosomes. In various aspects, the ribosomes are eukaryotic ribosomes, or a variant of a eukaryotic ribosome. Alternatively, the ribosomes of the CFPS system are prokaryotic ribosomes. In some aspects, the prokaryotic ribosomes are bacterial ribosomes, such as, for instance, an *E. coli* ribosome. Optionally, the ribosomes are each around 20 nm in diameter and about 65% rRNa and 35% ribosomal protein. In some aspects, the ribosomes comprises a small (30S) subunit and a large (50S) subunit. In certain instances, the small subunit comprises a 16S RNA subunit and proteins, and the large subject comprises a 5S RNA subunit and 23S RNA subunit and proteins. In exemplary aspects, the ribosomes of the CFPS system are naturally occurring. In alterative aspects, the ribosomes of the CFPS system are modified or variant versions of naturally occurring ribosomes.

With respect to the CFPS systems of the present disclosure, the ribosomes are attached to the structure or a plurality of structures. In exemplary instances, the ribosomes are attached to the structure at high density. In some aspects, the ribosomes are attached to a structure of the CFPS system at a density of at least about $10^6$ to about $6 \times 10^{14}$ ribosomes per cm$^2$ of structure. In some instances, at least or about $10^3$, at least or about $10^4$, at least or about $10^5$, at least or about $10^6$, at least or about $10^7$, at least or about $10^8$, at least or about $10^9$, at least or about $10^{10}$, at least or about $10^{11}$ at least or about $10^{12}$, at least or about $10^{13}$, at least or about $10^{14}$ ribosomes are attached per cm$^2$ of structure.

In some aspects, the ribosomes are attached to a carbon nanotube at a density of at least about 100 to about $10^{14}$ ribosomes per cm$^2$ of structure In exemplary aspects, the structure is a bead and the ribosome density of the CFPS system is about $1 \times 10^{10}$ ribosomes to about $2 \times 10^{14}$ ribosomes per uL of packed beads. In exemplary aspects, the structure is comprised of micropillars and the ribosome density of the CFPS system is about $1 \times 10^9$ ribosomes to about $1 \times 10^{14}$ ribosomes per uL of micropillars. In exemplary aspects, the structure is comprised of nanotubes and the ribosome density of the CFPS system is about $1 \times 10^{11}$ ribosomes to about $1 \times 10^{14}$ ribosomes per uL of nanotubes. In exemplary aspects, the structure is a lattice and the ribosome density of the CFPS system is about $10^8$ to $10^{13}$ ribosomes per uL lattice. In exemplary aspects, the structure is an aerogel and the ribosome density of the CFPS system is about $1\times10^{12}$ ribosomes to about $6\times10^{14}$ ribosomes per uL of aerogel. In exemplary aspects, the structure is an encapsulating hydrogel and the ribosome density of the CFPS system is about $1\times10^{9}$ ribosomes to about $1\times10^{13}$ ribosomes per uL of hydrogel.

In various aspects, the ribosomes are attached to the structure at about a one to one ratio. Without being bound to any particular theory, a 1:1 ratio of ribosome to bead advantageously reduces steric hindrance, maximizes ribosome mobility and freedom of movement, which in turn maximized ribosome activity.

The ribosomes of the CFPS system may be directly or indirectly attached to the structure. In various instances, the ribosome is modified to comprise a molecule or chemical moiety which binds to a chemical moiety present on the structure. For example, ribosomes may be biotinylated as essentially described in Example 1. Briefly, E. coli ribosomes are incubated with sulfo-N-hydroxysulfosuccinimide (sulfo-NHS)-modified biotin molecules. Without being bound to a particular theory, multiple biotin molecules attach to accessible lysine and arginine residues of the ribosome. The biotinylated ribosomes are attached to the structure or structures by incubating with structures coated with a biotin binding partner. In some aspects, the structures are beads and the beads are coated with the biotin binding partner, streptavidin. In alternative aspects, the structures or beads are coated with a different biotin binding partner, e.g., avidin or neutravidin, or a combination thereof.

In alternative instances, the ribosomes are attached to the structure via a linker. In exemplary aspects, the length of the linker is about 1 angstrom to about 1 μm in length (e.g., about 1 Å to about 1 μm, about 1 nm to about 1 μm, about 10 nm to about 1 μm, about 100 nm to about 1 μm, about 0.1 nm to about 100 nm, about 1 Å to about 10 nm, about 1 Å to about 1 nm).

In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain of atoms are all carbon atoms. In some embodiments, the chain atoms in the backbone of the linker are selected from the group consisting of C, O, N, and S. In some embodiments, the length of the linker is long enough to reduce the potential for steric hindrance. In exemplary aspects, the linker comprises a chain of carbon atoms, e.g., an aliphatic chain, optionally saturated or unsaturated. In some aspects, the linker is a fatty acid. In exemplary aspects, the linker is a polymer. In some aspects, the polymer is a polyamide, polycarbonate, polyalkylene, polyalkylene glycol, polyalkylene oxide, polyalkylene terepthalate, polymer of acrylic and methacrylic ester, poly (methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), a polyvinyl polymer (including polyvinyl alcohols, polyvinyl ethers, polyvinyl esters, polyvinyl halides, poly(vinyl acetate), and polyvinylpyrrolidone), a polyglycolide, polysiloxane, polyurethane and derivatives or co-polymer thereof. In some aspects, the polymer is a cellulose, including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene. In certain aspects, the polymer is a polyethylene glycol, wherein n is about 1 to about 4000.

In some embodiments, the linker is an amino acid or a peptidyl linker. Such peptidyl linkers may be any length. Exemplary linkers are from about 1 to 50 amino acids in length, 5 to 50, 3 to 5, 5 to 10, 5 to 15, or 10 to 30 amino acids in length.

Optionally, all the linkers of the CFPS system are uniform in length. In exemplary instances, the linkers vary in length by less than about 20% (e.g., less than about 15%, less than about 10%, less than about 7.5%, less than about 5%).

In alternative aspects, the linkers vary in length by about 20% or more (e.g., about 30%, about 40%, about 50%, about 60%, about 70%, about 80%, about 90%, or more).

In various aspects, linker comprises a functional group at one or both ends. In exemplary aspects, the linker comprises a function group at each end, e.g., the linker is a bifunctional linker. In certain instances, the functional group contains oxygen, including but not limited to a hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, carboxylic anhydride. In certain aspects, the functional group contains nitrogen, such as, carboxamide, amine (primary, secondary, tertiary), ketimine, aldimine, imide, azide, azo, cyanate, isocyante, nitrate, nitrile, isonitrile, nitrosooxy, nitro, nitroso, oxime, pyridyl, and carbamate. In other aspects, the functional group contains sulfur, e.g., sulfydryl, sulfide, disulfide, sulfinyl, sulfonyl, sulfino, sulfo, thiocyanate, isothiocyanate, carbonothioyl, carbothioic S-acid, carbothioic 0-acid, thiolester, thionester, carbodithioic, carbodithio.

In exemplary instances, the linker is a bifunctional linker comprising a first functional group (e.g., chemical moiety) at one end and a second functional group (e.g., chemical moiety) at the other end, wherein the first functional group directly or indirectly attaches to the ribosome and the second functional group directly or indirectly attaches to the structure. Optionally, the first functional group comprises or binds to biotin and optionally the second functional group comprises an NHS ester. In some aspects, the structure is functionalized with an amine.

In exemplary aspects, the ribosomes are modified to comprise a molecule or chemical moiety which binds (directly or indirectly) to a first chemical moiety of a bifunctional linker. In some instances, the ribosomes are modified to comprise biotin, wherein biotin is attached to an amino acid, optionally through the side chain. In certain aspects, the biotin is attached to an epsilon amine of a Lys residue, such as one which is present in the small subunit of the ribosome. In exemplary instances, the biotin is attached the side chain of a surface exposed Lys residue of the small subunit of the ribosome. In certain instances, the biotin attached to the ribosome binds to a biotin-binding partner which in turn binds to another biotin molecule which is attached to a bifunctional linker. In some cases, the biotin-binding partner can bind to multiple biotin molecules. In certain aspects, the biotin-binding partner is avidin, streptavidin, or neutravidin. In exemplary instances, the biotin-binding partner binds to a biotin attached to the side chain of a surface exposed Lys residue of the small subunit of the ribosome and to another biotin attached to a bifunctional linker. Optionally, the bifunctional linker is a polymer which terminates in a moiety that binds to biotin. In some aspects, the bifunctional linker comprises an amine and the amine binds to biotin.

In some aspects, the eukaryotic 60S ribosomal subunit is biotinylated by expressing the L1 protein, part of the 60S subunit, as translational fusion with a biotin acceptor peptide (Avi) [50]-[52]. This biotin acceptor peptide is recognized by the E. coli BirA biotin ligase. The linker between the L1 ribosomal subunit protein and the biotin acceptor peptide is encoded by the sequence GGSSGSGSSGGSGSSGSSGGS (SEQ ID NO: 1); the biotin acceptor peptide is encoded by the amino acid sequence GLNDIFEAQKIEWHE (SEQ ID NO: 2), where the bold "K" residue denotes the site of biotinylation. After the biotin acceptor sequence, a 2A ribosomal slippage site is inserted, followed by the E. coli birA gene. The T2A sequence allows polycistronic expression of both the RPL1 and BirA genes from a single promoter in mammalian cells [53]. This RPL1-GS linker-biotin acceptor peptide-T2A-birA cassette is inserted into the plasmid pNTI194 and co-transfected into HEK 393 Flp-In cells with pOG44—a plasmid that expressed the Flp recombinase. Stable integrants are isolated using antibiotic selection. Supplementing the growth media with 1 mM biotin result in biotinylated L1 ribosomal proteins that are incorporated into the 60S subunit [51]. Biotinylated 60S ribosomal subunits are isolated by affinity purification with streptavidin. After elution, the biotinylated ribosomal subunits are attached to the functionalized CNT-streptavidin.

In some aspects, the prokaryotic 50S ribosomal subunit is biotinylated by incorporating the 15 amino acid biotin acceptor peptide onto the N-terminus of the L4 ribosomal protein [54]. Co-transformation of a plasmid expressing the biotin tag-L4 protein fusion with a plasmid expressing the BirA biotin ligase enzyme and incubation with a biotin solution yield biotinylated 50S ribosomal subunits [54].

Other methods may be used to attach the smaller and complementary 40S eukaryotic and 30S prokaryotic subunits to tethers. Other types of ribosomal subunits may be tethered to surfaces, including mitochondrial ribosomes (e.g., the mammalian 28S and 39S subunits) and other ribosomal subunits yet to be discovered. Complementary ribosomal subunits that are tethered together have been shown to translate proteins successfully [55]. The tethered pair may also be attached to surfaces, either via one of the subunits or the inter-subunit tether itself.

Once biotinylated, ribosomes may attach to the structure, e.g., nanotube, via an avidin-biotin interaction. Without being bound to a particular theory, multiple amine sites may be present on each subunit, resulting in multiple biotin attachment sites. Other specific chemistries may be used to facilitate consistent and optimized ribosomal orientation, resulting in a higher protein generation rate. For example, a protein tag such as a polyhistidine-tag may be able to connect a known specific site on a ribosomal subunit to a nanotube that is functionalized with a nickel or cobalt chelate [47]. The polyhistidine-tag's small size (800 Da) should not hinder ribosomal functionality. Chelation of nickel or cobalt may be done via incubating a multi-walled nanotube (MWNT) in a solution of $Ni^{2+}$ or $Co^{2+}$ ions with the chelating agent sodium diethyldithiocarbamate [48].

The single-walled nanotube (SWNT) surface may be functionalized using the method in [49]. Briefly, nonspecific protein adsorption to the surface of the SWNT is blocked by attachment of poly-ethylene glycol (PEG) to the SWNT. PEG adsorption is enhanced by incubation with Triton X-405, a surfactant that acts as a wetting layer. Amine-terminated PEG (diamino-PEG) may be used, such that the amine-reactive biotin species biotinamidocaproic acid 3-sulfo-N-hydroxysuccinimide ester may be covalently linked to the SWNT-Triton-PEG scaffold. These SWNT-Triton-PEG-Biotin scaffolds may be incubated with a solution of streptavidin and then with biotinylated ribosomal subunits to facilitate attachment of the ribosomal subunit to the SWNT. The PEG chain length may be varied to minimize steric effects from the close proximity to the SWNT.

Solid Support

In exemplary aspects, the CFPS system comprises a solid support. The solid support may comprise one of many different geometries designed for its intended purpose. For example, the solid support may comprise a geometry suitable for holding, housing or containing the structure(s) of the presently disclosed CFPS system and/or holding, housing or containing the inlet(s) and/or outlet(s) and/or serving as a base to which the inlet(s) and/or outlet(s) are attached. The solid support may comprise a geometry suitable for defining fluidic movement and/or for holding, housing or containing electrodes. In various aspects, at least a portion of the solid support is substantially cylindrical with one or two open ends. In some aspects, the walls of the solid support taper at one end. In some instances, one or both open ends may be stoppered or capped. In some aspects, the solid support comprises or is a tube, e.g., a micro centrifuge tube or a test tube. The tube may comprise one end which is U-shaped or V-shaped and optionally is capped or stoppered at the opposite end. In alternative aspects, the walls of the solid support are substantially parallel at each end. In some aspects, the solid support comprises or is a column, e.g., chromatographic column. In some aspects, the column comprises walls that do not taper at either end but may be fitted with a cap or stopper. In various aspects, at least a portion of the solid support is substantially flat. In some instances, the solid support is a chip comprising a chamber, which holds, houses, or contains the structures. In some aspects, the solid support is a plate, e.g., a multi-well plate. In various aspects, the solid support of the presently disclosed CFPS system comprises a tube, a column, or a chip comprising a chamber.

The solid support may be made of any suitable, non-toxic, chemically-inert material, including but not limited to plastic, glass, silica, carbon, metal, metal oxide, ceramic, semiconductor, organic materials or a combination thereof. In some aspects, the solid support is a chip and the chip is made of silicon. In some aspects, the solid support is made of a porous material. In some instances, the solid support comprises a plurality of pores, optionally, wherein each pore is adjacent to a structure.

The solid support of the presently disclosed CFPS system may have a volumetric capacity of 1 μL to about 10 L. In some aspects, the solid support has a volume of less than 1 L. For instance, the volume size of the solid support is less than about 900 mL, less than about 800 mL, less than about 700 mL, less than about 600 mL, less than about 500 mL, less than about 400 mL, less than about 300 mL, less than about 200 mL, less than about 100 mL. In various aspects, the solid support has a volumes of less than 100 mL, e.g., about 90 mL, about 80 mL, about 70 mL, about 60 mL, about 50 mL, about 40 mL, about 30 mL, about 20 mL, about 10 mL, about 5 mL, about 1 mL or less). In various aspects, the solid support has a volume of greater than 1 L. For instance, the volume size of the solid support is greater than about 1.5 L, greater than about 2.5 L, greater than about 3.0 L, greater than about 5 L, or about 10 L.

In exemplary aspects, the solid support is a silicon wafer chip and comprises one or more chambers which holds, houses, or contains the structures of the CFPS system. In some aspects, the chip comprises 1, 2, 3, 4, 5, 6, 7, 8, 9, 10 or more chambers, optionally, in parallel or series. In certain aspects, each chamber has a volume of about 1 nL to about 10 mL. Optionally, each chamber has a volume of about 10 nL to about 1 µL (e.g., about 10 nL to about 900 nL, about 10 nL to about 800 nL, about 10 nL to about 700 nL, about 10 nL to about 600 nL, about 10 nL to about 500 nL, about 10 nL to about 400 nL, about 10 nL to about 300 nL, about 10 nL to about 200 nL, about 10 nL to about 100 nL, about 100 nL to about 1 µL, about 200 nL to about 1 µL, about 300 nL to about 1 µL, about 400 nL to about 1 µL, about 500 nL to about 1 µL, about 600 nL to about 1 µL, about 700 nL to about 1 µL, about 800 nL to about 1 µL, about 900 nL to about 1 µL). In various aspects, each chamber has a volume of about 1 µL to about 10 mL (e.g., about 10 µL to about 10 mL, about 50 µL to about 10 mL, about 100 µL to about 10 mL, 200 µL to about 10 mL, about 300 µL to about 10 mL, about 400 µL to about 10 mL, about 500 µL to about 10 mL, about 600 µL to about 10 mL, about 700 µL to about 10 mL, about 800 µL to about 10 mL, about 900 µL to about 10 mL, about 1 mL to about 10 mL, about 2.5 mL to about 10 mL, about 5 mL to about 10 mL, about 7.5 mL to about 10 mL, about 1 µL to about 7.5 mL, about 1 µL to about 5 mL, about 1 µL to about 2.5 mL, about 1 µL to about 1.0 mL, about 1 µL to about 900 µL, about 1 µL to about 800 µL, about 1 µL to about 700 µL, about 1 µL to about 600 µL, about 1 µL to about 500 µL, about 1 µL to about 400 µL, about 1 µL to about 300 µL, about 1 µL to about 200 µL, about 1 µL to about 100 µL, about 1 µL to about 50 µL, about 1 µL to about 10 µL. In various aspects, each chamber on the chip is positioned between at least one inlet and at least one outlet. Optionally, the chip comprises a first chamber and a second chamber and each chamber is positioned between at least one inlet and at least one outlet, wherein at least one outlet of the first chamber serves as an inlet for the second chamber.

In exemplary aspects, the structures of the CFPS system are not attached to the solid support. In some aspects, the solid support holds, houses, or contains the structures. In exemplary instance, the spacing between each structure is about 10 nm to about 1 mm. In exemplary aspects, the structures are spherical, e.g., beads. The beads may accord with the above teachings and description of beads. For example, the average bead size is about 10 nm to about 1 mm, optionally about 20 µm to about 500 µm in diameter, optionally, about 40 µm to about 200 µm in diameter. In various aspects, the structures are approximately the same in diameter. In alternative aspects, the structures vary in diameter (e.g., by at least about 50%). In certain aspects, each bead has an average surface area of about 300 nm² to about 4 mm². In various aspects, the ribosomes are attached to the beads at a density of at least about $3 \times 10^{11}$ ribosomes per volume of packed beads. In some aspects, the solid support of the CFPS system is a column and the beads are housed in the column. In some aspects, the solid support is a chip comprising one or more chambers. Optionally, the beads are packed into a chamber of the chip and in some aspects, the chamber is coupled to the fluidic inlet(s) and fluidic outlet(s). The chip may be comprised of silicon. In some aspects, the volumetric capacity of the chamber of the chip is about 10 nL to about 10 mL (e.g., about 10 nL to about 1 µL, about 10 µL to about 10 mL) In some aspects, the volumetric capacity of the chamber of the chip is about 10 nL to about 100 nL, about 10 nL to about 1 µL, about 10 nL to about 10 µL, about 10 nL to about 100 µL, 10 nL to about 1 mL, about 1 mL to about 10 mL, about 100 µL to about 10 mL, about 10 µL to about 10 mL, about 1 µL to about 10 mL, about 100 nL to about 10 mL). In some aspects, the chip comprises more than one chamber, optionally, each of which is positioned between at least one inlet and at least one outlet. In some aspects, the chip comprises a first chamber and a second chamber and each chamber is positioned between at least one inlet and at least one outlet, wherein at least one outlet of the first chamber serves as an inlet for the second chamber.

In exemplary aspects, the structures of the CFPS system are attached to the solid support. In exemplary instances, the structures are attached to only a portion of the solid support, because other parts of the solid support are purposed for, e.g., holding, housing or containing the inlet(s) and/or outlet(s) and/or serving as a base to which the inlet(s) and/or outlet(s) are attached. Alternatively or additionally, the structures are attached to only a portion of the solid support, in some aspects, because of the way the fluids are designed to move through the CFPS system. In some aspects, the solid support is substantially flat, e.g., a chip, and the structures are attached to only one side of the solid support (e.g., chip). In some aspects, the spacing between each structure on the solid support is about 5 nm to about 10 µm. In some aspects, each structure has a surface area of at least about 3 nm² to about 4 mm² or at least about 10 µm² or at least about 15 µm². In exemplary aspects, the solid support is porous and a pore is positioned between or adjacent to each structure attached the solid support. In certain instances, each structure is a nanotube. The nanotube in some aspects accords with the descriptions of nanotubes above. Optionally, the nanotube is about 15 µm long and about 200 nm wide, optionally, the ribosomes are attached to the nanotubes at a density of about $3 \times 10^{13}$ ribosomes per µL of nanotube volume. Optionally, the nanotubes are approximately the same height. Alternatively, the nanotubes vary in height by at least about 50%. In some aspects, the nanotube is a carbon nanotube (CNT). In some aspects, the solid support (optionally a chip or a bead) comprises about $10^9$ CNTs per cm² of solid support.

In some aspects, the structures are functionalized to facilitate attachment of ribosomes to surfaces. In some instances, nanotube forests are grown directly on various solid supports [34], [35]. This method ensures vertical alignment, controllable spacing, and a robust connection to the substrate without the need of chemistry to attach the nanotube ends to the substrate. However, chemical linking may be needed in cases that ribosomes are attached to non-planar surfaces (e.g., micro/nanoparticles, matrices, pores, etc.) or to materials not compatible with nanotube growth processes. Various methods to attach the ends of nanotubes to substrates, including the avidin-biotin interaction [42], the condensation reaction of hydroxyl-terminated silicon substrate and carboxylic acid groups on the nanotubes [43], alkanethiol SAMs to attach nanotubes on metals surfaces [44], and the condensation reaction between amine groups on the nanotubes and carboxylic acid groups on the nanotubes [45] are known in the art. The present disclosure is not limited to end-attached nanotube tethers; sidewalls may be attached to surfaces and still leave adequate sidewall available for ribosome attachment. Single-walled carbon nanotubes in some aspects are deposited onto an $SiO_2$ surface in suspension in 1,2-dichloroethane [46]. In addition, sidewall attachment may be achieved using similar methods as with end attachment methods, except steps are necessary to ensure sidewalls are amenable to functionalization (e.g., carboxylic acid groups on sidewalls). Nanotube sidewalls may also be attached to surfaces using nonspecific methods including electrostatics, surface tension, non-specific adsorption, hydrophobicity, and any mechanical means to retain nanotubes or nanotube accumulations within the reaction chamber. Nanotubes may be attached to various material compositions, including—but not limited to—metal, glass, plastics and other polymers, hydrogels, semiconductors, epoxy resins (e.g., SU-8 photoresist), graphene layers, and fullerenes (e.g., buckyballs). The nanotubes may also be connected to other nanotubes of similar or different composition to create a nanotube mesh and maximize surface area per unit reaction chamber volume.

In exemplary aspects, the structures are attached to the solid support under a controlled condition. For example, the controlled condition may be one comprising an electrostatic or magnetic force, and, in some aspects, each structure is attached only when a magnetic field is applied to the system. In various aspects, the structures are magnetic, optionally, magnetic beads. Other controlled conditions are contemplated as described herein.

Additional Considerations

In exemplary aspects, the CFPS system comprises one solid support containing one or more structures to which a plurality of ribosomes are attached. In various aspects, the CFPS system comprises a plurality of ribosomes encapsulated within a structures, e.g., a hydrogel, polymer, gelatin. In alternative aspects, the CFPS system comprises more than one solid support or a single solid support comprising more than one chamber. In some aspects, the CFPS system comprises a series of columns (optionally, stacked vertically on top of another) or a chip comprising a series of chambers linked by fluidic connectors.

In exemplary aspects, the CFPS system is designed for fluids, liquids, or solutions to move through the structure or plurality thereof. In exemplary aspects, the CFPS system comprises at least one inlet purposed for fluids, liquids, or solutions to move into the CFPS system or a portion thereof and at least one outlet purposed for fluids, liquids, or solutions to move out of the CFPS system or portion thereof. In exemplary aspects, the plurality of structures is positioned between the at least one inlet and at least one outlet, such that the fluids, liquids, or solutions contact the structures. In some aspects, the CFPS system is designed for microfluidics and the CFPS system comprises at least one microfluidic inlet and at least one microfluidic outlet. In exemplary instances, the movement of fluids, liquids, or solutions through the CFPS system is cyclic and the inlet and outlet are connected to allow cyclic movement of the fluids, liquids, or solutions. In some aspects, the CFPS system comprises more than one inlet. In some aspects, the CFPS system comprises more than one outlet. Optionally, at least one inlet is purposed for adding new fluids, liquids, or solutions to the system. Also, optionally, at least one outlet is purposed for collecting fluids, liquids or solutions that have contacted the structures. In exemplary instances, the fluids, liquids, or solutions comprise one or more reagents for an in vitro translation (IVT) reaction. Exemplary IVT reaction reagents are described herein. In exemplary aspects, the solid support is a chip comprising a chamber which holds, houses, or contains structures (e.g., beads) to which ribosomes are attached. In exemplary instances, the chamber is positioned between an inlet and an outlet, optionally, a microfluidic inlet and a microfluidic outlet. In some aspects, the microfluidic inlet and microfluidic outlet are operably connected for fluids, liquids or solutions to enter through the inlet, contact the structures in the chamber, and exit out the outlet, wherein the fluids, liquids or solutions exit chamber and enter a connector which directs movement of the fluids, liquids or solutions back to the inlet to re-enter the chamber.

In exemplary aspects, the CFPS system comprises a pump which controls the speed and/or direction of fluidic movement. In exemplary instances, the CFPS system does not comprise a pump. In some aspects, fluid moves through the CFPS system due to applied forces (vis-a-vis, e.g., shaking, rocking, tumbling, by e.g., vortexing, sonicating, spinning) or due to gravitational forces. In exemplary aspects, the solid support is a column and the structures are beads to which ribosomes are attached. In some aspects, the column is packed with the beads and the fluids move through the packed beads in the column by way of gravity.

In various aspects, the CPFS system comprises a filter. Optionally, the filter is positioned near the outlet(s). In various instances, the filter is sized to allow IVT reaction reagents to pass through, while larger molecules, e.g., protein products of the IVT reactions, do not pass through the filter.

Kits

The present disclosure furthermore provides a kit comprising any one of the presently disclosed CFPS systems. In exemplary embodiments, the kit comprises a CFPS system of the present disclosure and one or more IVT reaction reagents. As used herein, the term "in vitro translation (IVT) reaction reagent" refers to any molecule, compound, factor, or salt, which functions in an IVT reaction. In some aspects, the IVT reaction reagents include a transfer RNA (tRNA), an amino acid, an enzymatic cofactor, and an energy source. In exemplary aspects, the kit comprises a tRNA for each of the 20 essential amino acids and, optionally, an amount of each of the 20 essential amino acids. In exemplary instances, the enzymatic cofactor is an initiation factor, elongation factor, termination factor. Also, for instance, the kit comprises one or more IVT reaction enzymatic co-factors, including but not limited to: an amino acdyl-tRNA synthetase, methionyl-tRNA transformylase, initiator methionyl tRNA, myokinase, creatine kinase, creatine phosphate, 10-formyl-5,6,7,8-tetrahydrofolic acid, pyrophosphatase, protein disulfide isomerase, and protein folding chaperone. In various aspects, the energy source is ATP or GTP. In exemplary instances, the kit further comprises an energy regenerating system, e.g., creatine phosphate and creatine phosphokinase or phosphoenol pyruvate and pyruvate kinase). In various aspects, the kit further comprises co-factors, such as, $Mg^{2+}$, $K^+$. In various instances, the kit comprises wheat germ extract and/or rabbit reticulocyte lysate. The kit in some aspects, comprise one or more reagents for in vitro transcription. For example, the kit may comprise prokaryotic phage RNA polymerase and promoter (T7, T3, or SP6) with eukaryotic or prokaryotic extracts to synthesize proteins from exogenous DNA templates.

In exemplary aspects, the IVT reaction reagent is one of the components described in the table below.

| Component | Process | Cell Type | Function |
| --- | --- | --- | --- |
| DNA | Transcription | Both | Template for transcription |
| T7 RNA polymerase | Transcription | Both | Transcribe DNA template to RNA |

| Component | Process | Cell Type | Function |
|---|---|---|---|
| Initiation factors (IF1, IF2, IF3) | Translation | Prokaryotic | Recognize AUG start codon, position mRNA correctly in the ribosome, and stimulate ribosomal subunit joining |
| Elongation factors (EF-G, EF-Tu, EF-Ts) | Translation | Prokaryotic | Mediate insertion of correct tRNA and translocation from A to P site |
| Termination factors (RF1, RF3, RRF) | Translation | Prokaryotic | Recognize stop codon and release the protein from the ribosome |
| Initiation factors | Translation | Eukaryotic | Recognize mRNA, position mRNA correctly in the ribosome, and stimulate ribosomal subunit joining |
| Elongation factors (eEF-1, eEF-2) | Translation | Eukaryotic | Mediate insertion of correct tRNA and translocation from A to P site |
| Termination factors (eRF1) | Translation | Eukaryotic | Recognize stop codon and release the protein from the ribosome |
| 20 aninoacyl-tRNA synthetases | Translation | Both | Catalyzes attachment of amino acid onto its cognate tRNA |
| Methionyl-tRNA transformylase | Translation | Prokaryotic | Catalyzes formation of N-formylmethoinine tRNA (initiator Met amino acid) |
| Initiator methionyl-tRNA | Translation | Eukaryotic | Initiator amino acid that localizes to the P site in the pre-initiation complex |
| Ribosome | Translation | Both (specific) | Catalyzes translation |
| tRNAs (46) | Translation | Both | Subunits for polypeptide chains |
| NTPs | Translation | Both | Subunits for DNA synthesis |
| Creatine phosphate | Translation | Both | Energy source; can provide phosphate group to convert ADP to ATP |
| 10-formyl-5,6,7,8-tetrahydrofolic acid | Translation | Prokaryotic | Necessary for formylation of the N-formylmethoinine tRNA (initiator Met amino acid) |
| Amino acids (20) | Translation | Both | Subunits for protein synthesis |
| Creatine kinase | Translation | Both | Converts ATP to ADP |
| Myokinase | Translation | Both | Catalyzes interconversion of adenine nucleotides (ATP and AMP to ADP) |
| Nucleoside-diphosphatekinase | Translation | Both | Catalyzes phosphorylation of nucleoside diphosphates to form NTPs |
| Pyrophosphatase | Translation | Both | Catalyzes hydrolysis of diphosphate bonds (e.g., GTP to GDP and inorganic phosphate) |
| Chaperones or other proteins to assist in proper folding | Translation | Both | Ensure that the nascent protein is properly folded during or immediately after translation and release from the ribosome |
| Protein disulfide isomerase | Translation | Both | Enzyme that catalyzes disulfide bond formation and breakage; aids in proper protein folding |
| Components to optimize redox potential | Translation | Both | Aid in proper disulfide bond formation and protein folding during and after translation |

Methods of Protein Production

Further provided herein are uses of the presently disclosed CFPS system. The present disclosure provides in exemplary embodiments the use of the presently disclosed CFPS system in a method for in vitro protein synthesis. Accordingly, provided herein are methods of producing a protein. In exemplary embodiments, the method comprises contacting one or more solutions comprising one or more in vitro translation reagents with the plurality of ribosomes of the presently disclosed CFPS system. In exemplary aspects, the method comprises adding one or more solutions comprising one or more in vitro translation reagents through the inlet(s) of the CFPS system of any one of the previous claims and collecting proteins through the outlet(s). Optionally, the in vitro translation reagents comprise a messenger RNA encoding the protein, a set of tRNAs, a set of amino acids, and an energy source. In some aspects, all reagents are provided to the CFPS system in a single solution, and, optionally, the single solution is passed through the inlet(s), through the plurality of structures comprising ribosomes, through a filter, and through the outlet(s) of the CFPS system. In some aspects, the single solution is cycled back through the inlet(s) of the CFPS system, after passing through the outlet(s) of the CFPS system. In various instances, a second solution comprising additional reagents are passed through an inlet(s) of the CFPS system simultaneously or sequentially with the cycled single solution. As discussed above, in some aspects, the solution is pumped through the CFPS system using a pump. In certain instances, the pump is set to deliver the one or more solutions at a rate of about 1 nL per min to about 1 mL per min, e.g., about 1 nL per min to about 100 µL per min, about 1 nL per min to about 10 µL per min, about 1 nL per min to about 1 µL per min, about 1 nL per min to about 100 nl per min, about 1 nL per min to about 10 nL per min, about 10 nL per min to about 1 mL per min, about 100 nL per min to about 1 mL per min, about 1 µL per min to about 1 mL per min, about 10 µL per min to about 1 mL per min, or about 100 µL per min to about 1 mL per min). In some aspects, the one or more solutions are delivered through the CFPS system without a pump. In some aspects, the one or more solutions move through the CFPS system due to applied forces (vis-a-vis, e.g., shaking, rocking, tumbling, by e.g., vortexing, sonicating, spinning, electroosmotic flow) or due to gravitational and/or capillary forces.

Methods of Treatment

A method of treating a disease in a subject is provided by the present disclosure. In exemplary embodiments, the method comprises administering a therapeutic protein to the subject in an amount effective to treat the disease, wherein the therapeutic protein was produced according to a presently disclosed method of producing a protein.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating a disease of the present disclosure can provide any amount or any level of treatment. Furthermore, the treatment provided by the method may include treatment of one or more conditions or symptoms or signs of the disease being treated. For instance, the treatment method of the presently disclosure may inhibit one or more symptoms of the disease. Also, the treatment provided by the methods of the present disclosure may encompass slowing the progression of the disease. The term "treat" also encompasses prophylactic treatment of the disease. Accordingly, the treatment provided by the presently disclosed method may delay the onset of the disease being prophylactically treated. In exemplary aspects, the method delays the onset of the disease by 1 day, 2 days, 4 days, 6 days, 8 days, 10 days, 15 days, 30 days, two months, 4 months, 6 months, 1 year, 2 years, 4 years, or more. The prophylactic treatment encompasses reducing the risk of the disease being treated. In exemplary aspects, the method reduces the risk of the disease 2-fold, 5-fold, 10-fold, 20-fold, 50-fold, 100-fold, or more.

In certain aspects, the method of treating the disease may be regarded as a method of inhibiting the disease, or a symptom thereof. As used herein, the term "inhibit" and words stemming therefrom may not be a 100% or complete inhibition or abrogation. Rather, there are varying degrees of inhibition of which one of ordinary skill in the art recognizes as having a potential benefit or therapeutic effect. The presently disclosed methods may inhibit the onset or re-occurrence of the disease or a symptom thereof to any amount or level. In exemplary embodiments, the inhibition provided by the methods is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition).

Subjects

In some embodiments, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human. In some aspects, the human is an adult aged 18 years or older. In some aspects, the human is a child aged 17 years or less.

Diseases

In some aspects, the disease treated by the presently disclosed method is a tumor or a cancer, an inflammatory disease, a neurodegenerative disease, a cardiac disease, or a metaolic disease.

The cancer in some aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma.

In exemplary instances, the inflammatory disease is allergy, asthma, an autoimmune diseases, coeliac disease, glomerulonephritis, hepatitis, inflammatory bowel disease, preperfusion injury and transplant rejection. In some aspects, the inflammatory disease is Crohn's disease or ulcerative colitis. In some aspects, the disease is an autoimmune disease, For purposes herein, "autoimmune disease" refers to a disease in which the body produces an immunogenic (i.e., immune system) response to some constituent of its own tissue. In other words the immune system loses its ability to recognize some tissue or system within the body as "self and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The neurodegenerative disease in some aspects is Alzheimer's disease, Parkinson's disease, Multiple Sclerosis, Amylotrophic Lateral Sclerosis, other demyelination related disorders, senile dementia, subcortical dementia, arteriosclerotic dementia, AIDS-associated dementia, or other dementias, a central nervous system cancer, traumatic brain injury, spinal cord injury, stroke or cerebral ischemia, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal dysmyotrophy, progressive supranuclear palsy, dystonia, muscle spasticity, tremor, retinitis pigmentosa, striatonigral degeneration, mitochondrial encephalo-myopathies, neuronal ceroid lipofuscinosis, hepatic encephalopathies, renal encephalopathies, metabolic encephalopathies, toxin-induced encephalopathies, and radiation-induced brain damage.

In some aspects, the cardiac disease is diastolic dysfunction. As used herein, the term "diastolic dysfunction" refers to a condition in which abnormalities in mechanical function are present during diastole. Diastolic dysfunction can occur in the presence or absence of heart failure and can co-exist with or without abnormalities in systolic function (Zile et al., JACC 41: 1519-1522 (2003)). Accordingly, in some embodiments, the diastolic dysfunction is diastolic dysfunction in the absence of systolic dysfunction, which is also known as, diastolic dysfunction with preserved ejection fraction, diastolic dysfunction with preserved systolic function, and diastolic dysfunction with preserved left ventricular function. As used herein, the term "preserved ejection fraction" refers to a left ventricular ejection fraction which is greater than or about 45%, e.g., greater than or about 50%. In some aspects, the preserved ejection fraction is one which is greater than or about 50%. In some embodiments, the diastolic dysfunction is an early diastolic dysfunction. As used herein, the term "early diastolic dysfunction" refers to a medical condition in which ventricle filling is impaired as evidenced by the ratio of the peak velocities of blood across the mitral valve in diastole in early filling, the E wave to that during atrial contraction, the A wave, (E/A ratio) <1 and peak early (E') and late (A') mitral annular velocities recorded by conventional pulsed wave Doppler method also <1 (Vasan et al., J Am Coll Cardiol 26:1565-1574 (1995); Xie et al., J Am Coll Cardiol 24:132-139 (1994); Moller et al., J Am Coll Cardiol 35:363-370 (2000)).

In some embodiments, the cardiac disease is systolic dysfunction. In simple terms, systolic dysfunction is a condition in which the pump function or contraction of the heart (i.e., systole), fails. Systolic dysfunction may be characterized by a decreased or reduced ejection fraction, e.g., an ejection fraction which is less than 45%, and an increased ventricular end-diastolic pressure and volume. In some aspects, the strength of ventricular contraction is weakened and insufficient for creating an appropriate stroke volume, resulting in less cardiac output.

In some embodiments, the cardiac disease comprises a lack of cardiac muscle health or function. In some aspects, the cardiac disease is cardiotoxicity, a condition wherein the heart muscle is damaged and often leads to the heart's inability to pump blood throughout the body.

In some embodiments, the cardiac disease is heart failure (HF), which is defined as the ability of the heart to supply sufficient blood flow to meet the body's needs. In some embodiments, the signs and symptoms of heart failure include dyspnea (e.g., orthopnea, paroxysmal nocturnal dyspnea), coughing, cardiac asthma, wheezing, dizziness, confusion, cool extremities at rest, chronic venous congestion, ankle swelling, peripheral edema or anasarca, nocturia, ascites, heptomegaly, jaundice, coagulopathy, fatigue, exercise intolerance, jugular venous distension, pulmonary rales, peripheral edema, pulmonary vascular redistribution, interstitial edema, pleural effusions, or a combination thereof. In some embodiments, the signs and symptoms of heart failure include dyspnea (e.g., orthopnea, paroxysmal nocturnal dyspnea), fatigue, exercise intolerance, jugular venous distension, pulmonary rales, peripheral edema, pulmonary vascular redistribution, interstitial edema, pleural effusions, or a combination thereof. In some embodiments, the symptom of heart failure is one of the symptoms listed in the following table, which provides a basis for classification of heart failure according to the New York Heart Association (NYHA).

| NYHA Class | Symptoms |
| --- | --- |
| I | No symptoms and no limitation in ordinary physical activity, e.g. shortness of breath when walking, climbing stairs etc. |

-continued

| NYHA Class | Symptoms |
| --- | --- |
| II | Mild symptoms (mild shortness of breath and/or angina) and slight limitation during ordinary activity. |
| III | Marked limitation in activity due to symptoms, even during less-than-ordinary activity, e.g. walking short distances (20-100 m). Comfortable only at rest. |
| IV | Severe limitations. Experiences symptoms even while at rest. Mostly bedbound patients. |

Patients presenting with signs and/or symptoms of heart failure may be suffering from systolic dysfunction, diastolic dysfunction, or a combination of the two. Heart failure with preserved ejection fraction, which is also known as, heart failure with preserved systolic function, heart failure without systolic dysfunction, and heart failure with preserved left ventricular function, is a clinical condition in which the subject exhibits a preserved ejection fraction (e.g., an ejection fraction which is greater than or about 45%, or greater than or about 50%) along with signs and/or symptoms of heart failure. In some embodiments, the heart failure is acute heart failure with preserved ejection fraction. In some embodiments, the heart failure is chronic heart failure with preserved ejection fraction. In some embodiments, the heart failure is acute and chronic heart failure with preserved ejection fraction. In some embodiments, the heart failure which is diagnosed is a Class I, Class II, Class III, or Class IV heart failure as defined by the New York Heart Association (NYHA). See, for example, The Criteria Committee of the New York Heart Association. Nomenclature and Criteria for Diagnosis of Diseases of the Heart and Great Vessels. 9th ed. Boston, Mass: Little, Brown & Co; 1994:253-256, and the table above. In some embodiments, the heart failure is an NYHA Class I or Class II heart failure.

In certain aspects the metabolic disease is metabolic syndrome. Metabolic Syndrome, also known as metabolic syndrome X, insulin resistance syndrome. or Reaven's syndrome, is a disorder that affects over 50 million Americans. Metabolic Syndrome is typically characterized by a clustering of at least three or more of the following risk factors: (1) abdominal obesity (excessive fat tissue in and around the abdomen), (2) atherogenic dyslipidemia (blood fat disorders including high triglycerides, low HDL cholesterol and high LDL cholesterol that enhance the accumulation of plaque in the artery walls), (3) elevated blood pressure, (4) insulin resistance or glucose intolerance, (5) prothrombotic state (e.g.,high fibrinogen or plasminogen activator inhibitor-1 in blood), and (6) pro-inflammatory state (e.g.,elevated C-reactive protein in blood). Other risk factors may include aging, hormonal imbalance and genetic predisposition. Metabolic Syndrome is associated with an increased the risk of coronary heart disease and other disorders related to the accumulation of vascular plaque, such as stroke and peripheral vascular disease, referred to as atherosclerotic cardiovascular disease (ASCVD). Patients with Metabolic Syndrome may progress from an insulin resistant state in its early stages to full blown type II diabetes with further increasing risk of ASCVD. Without intending to be bound by any particular theory, the relationship between insulin resistance, Metabolic Syndrome and vascular disease may involve one or more concurrent pathogenic mechanisms including impaired insulin-stimulated vasodilation, insulin resistance-associated reduction in NO availability due to enhanced oxidative stress, and abnormalities in adipocyte-derived hormones such as adiponectin (Lteif and Mather, Can. J. Cardiol. 20 (suppl. B):66B-76B (2004)). According to the 2001 National Cholesterol Education Program Adult Treatment Panel (ATP III), any three of the following traits in the same individual meet the criteria for Metabolic Syndrome: (a) abdominal obesity (a waist circumference over 102 cm in men and over 88 cm in women); (b) serum triglycerides (150 mg/dl or above); (c) HDL cholesterol (40 mg/dl or lower in men and 50 mg/dl or lower in women); (d) blood pressure (130/85 or more); and (e) fasting blood glucose (110 mg/dl or above). According to the World Health Organization (WHO), an individual having high insulin levels (an elevated fasting blood glucose or an elevated post meal glucose alone) with at least two of the following criteria meets the criteria for Metabolic Syndrome: (a) abdominal obesity (waist to hip ratio of greater than 0.9, a body mass index of at least 30 kg/m2, or a waist measurement over 37 inches); (b) cholesterol panel showing a triglyceride level of at least 150 mg/dl or an HDL cholesterol lower than 35 mg/dl; (c) blood pressure of 140/90 or more, or on treatment for high blood pressure). (Mathur, Ruchi, "Metabolic Syndrome," ed. Shiel, Jr., William C., MedicineNet.com, May 11, 2009). For purposes herein, if an individual meets the criteria of either or both of the criteria set forth by the 2001 National Cholesterol Education Program Adult Treatment Panel or the WHO, that individual is considered as afflicted with Metabolic Syndrome. In exemplary aspects, the metabolic disease is diabetes, which may be diabetes mellitus type I, diabetes mellitus type II, or gestational diabetes, either insulin-dependent or non-insulin-dependent. In some aspects, the metabolic disease is obesity.

Proteins/Peptides

The protein produced by the presently disclosed methods of producing a protein or the protein administered to the subject of the presently disclosed methods of treating may be any protein, or a fragment thereof. The protein in some aspects is an enzyme, hormone, growth factor, cytokine, lymphokine, coagulation factor (blood factor), hematopoietic factor, a ligand of a cell-surface receptor, or the like. In some aspects, the protein is any one of M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFa, TNF1, TNF2, G-CSF, Meg-CSF, GM-CSF, thrombopoietin, stem cell factor, and erythropoietin. Additional growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2 α, cytokine-induced neutrophil chemotactic factor 2 β, β endothelial cell growth factor, endothelin 1, epithelial-derived neutrophil attractant, glial cell line-derived neutrophic factor receptor α 1, glial cell line-derived neutrophic factor receptor α 2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor a, nerve growth factor nerve growth factor receptor, neurotrophin-3, neurotrophin-4, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor γ5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, and chimeric proteins and biologically or immunologically active fragments thereof.

In exemplary aspects, the protein is a tumor antigen. In exemplary aspects, the tumor antigen is an antigen derived from a viral protein, an antigen derived from point mutations, or an antigen encoded by a cancer-germline gene. In exemplary aspects, the tumor antigen is p53, KRAS, NRAS, MAGEA, MAGEB, MAGEC, BAGE, GAGE, LAGE/NY-ESO1, SSX, tyrosinase, gp100/pmel17, Melan-A/MART-1, gp75/TRP1, TRP2, CEA, RAGE-1, HER2/NEU, WT1.

In exemplary aspects, the protein is C1 esterase inhibitor, glucocerebrosidase, an antibody, insulin, a Fc fusion protein, an albumin fusion, a cytokine, interferon, hormone, or other soluble protein factor, an enzyme, antihemophilic factor, coagulation factor, and the like.

Exemplary Embodiments

The following provides an exemplary embodiment of the presently disclosed CFPS system and additional aspects thereof.

In exemplary embodiments, the CFPS system is a device that creates a purified, concentrated protein product from a nucleic acid input in vitro in a microfluidic device. FIG. 1 illustrates the process. A nucleic acid solution (DNA or RNA) that contains the target sequence for the desired protein (Input 1) is injected into the microfluidic device and transported to a reaction module. After protein synthesis, filtering and/or concentration modules may be used to remove unwanted byproducts and unreacted agents to produce a purified protein concentrate.

Exemplary Reaction Modules

Figure 2:
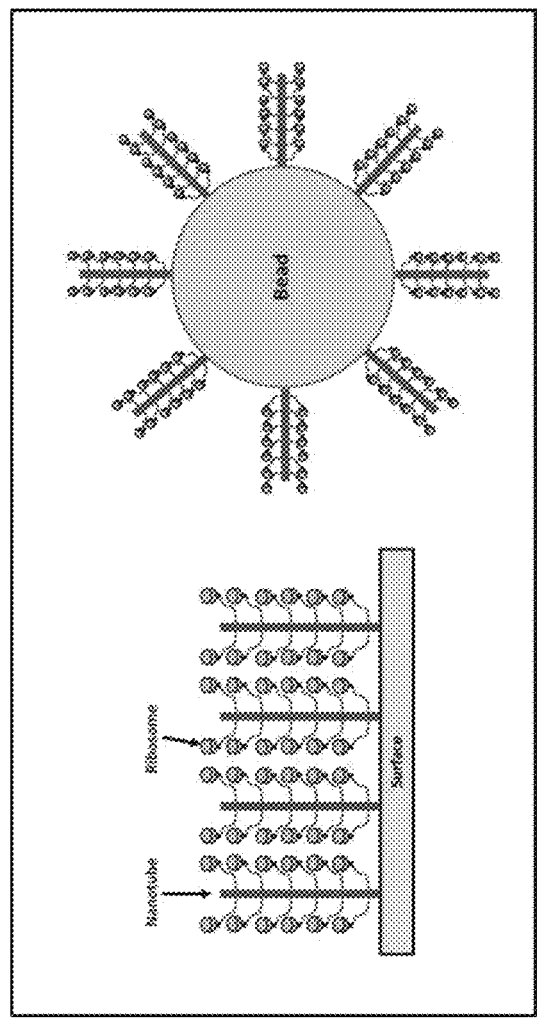
FIG. 2 is an illustration depicting nanotubes for use in greatly increasing the density of ribosomes on a surface by adding a third dimension (height) that enables multiple ribosomal attachment sites. Many surfaces may be modified using this method, including planar substrates and beads (shown) and other surfaces (e.g. gels, additive manufacturing matrices, etc.).

In exemplary aspects, the reaction module comprises a fluidic chamber that contains ribosomes localized to the reaction chamber. The ribosomes may represent an entire ribosome (e.g., eukaryotic cytoplasmic 80S, eukaryotic mitochondrial 55S, prokaryotic 70S), or a portion thereof, e.g., individual ribosomal subunits, such as, e.g., eukaryotic cytoplasmic 40S and 60S, eukaryotic mitochondrial 28S and 39S, prokaryotic 30S and 50S. Whole ribosomes and/or ribosome subunits are in some aspects attached to the chamber's walls and floors or attached to or encapsulated within entities inside the chamber that are either free-floating (e.g., particles) or fixed extensions—whether flexible, rigid, permeable (e.g., hydrogel)—to the chamber's walls and floors. In exemplary instances, an extension is a gel matrix or other matrix that fills the entire chamber (e.g., packed bead column, solid membrane), but allows perfusion of translation mixture and mRNA to interact with attached ribosomal parts. In various aspects, these extensions also are temporarily attached to the chamber's walls and floors, become free-floating, then subsequently reattached (or remain free-floating). In various instances, attachment of the ribosomes to the aforementioned entities is accomplished via polymer linkers (e.g., PEG), surface chemistries (e.g., thiol, oxysilane, etc.), physical adsorption (e.g., van der Waals forces), avidin-biotin complexes (i.e., avidin, streptavidin, and Neutravidin), antibody-antigen and other protein-protein interactions, protein tags (e.g., polyhistidine-tag), or a combination of the above. The present disclosure however is not limited to the aforementioned examples of physically linking the ribosomes to surfaces. In various aspects, ribosomal attachment is performed chemically, biologically, and electrically. In exemplary aspects, nanotubes of various compositions (carbon, DNA [Rothemund et al., J Am Chem Soc 126(50): 16344-16352 (2004)], metal and nonmetals, other organic compounds, inorganic compounds) are used to extend a ribosome's distance from the linked surface to up to tens of microns. Multiple ribosomes may be attached to each nanotube (FIG. 2), greatly increasing the density (e.g., possibly over three orders of magnitude) of protein generators when compared to single ribosome tethering methods [Puglisi et al., U.S. Pat. No. 7,297,532]. In some aspects other structures, e.g., nanowires; nanorods; nanofibers; graphene layers; nanocrystals; and fullerenes such as Bucky balls, Bucky tubes, and fullerene rings are used in place of "nanotubes". A second input (Input 2) in exemplary aspects supplies the reaction chamber with the remaining components required for protein translation (amino acids, tRNA, energy sources, translation factors, etc. listed in Table 1). This mixture may also include components for transcription from DNA to mRNA in the case the desired starting sample is DNA. Depending on the design of the reaction module, the transcription mixture in some aspects is included in Input 1 instead of Input 2.

Some exemplary manifestations of the reaction module are shown in FIGS. 3-5. FIG. 3(a) shows how ribosomes can be tethered to a substrate locally around one side of a microscale or nanoscale pore. Although only one ribosome is shown attached to each tether, multiple ribosomes or ribosomal subunits may be attached to a single tether, as previously shown in FIG. 2. This and further representations of single ribosome/tether pairs also may represent individual tethers with multiple ribosomes attached. A solution containing the necessary components for protein translation are loaded into the same side as the ribosomes (FIG. 1, Input 2). A concentrated mRNA solution, or a solution of DNA and appropriate transcription components to create mRNA, is injected on the opposing side of the pore. Target protein synthesis occurs when the mRNA molecules translocate through the pore and are translated into their corresponding polypeptide sequences. Messenger RNA translocation through the pore may be via diffusion through molecular concentration and/or thermal gradients, electrophoresis by an alternating or direct current electric field, electroosmotic flow (i.e., plug flow), pressure driven flow (i.e., parabolic flow), or magnetic field. This example is not limited to a single pore, but in some aspects includes an array of pores, effectively creating a membrane that separates the translation solution from the mRNA template (FIG. 3(b)). This advantageously supplies the ribosome with the needed mRNA at extremely small diffusion distances and high localized concentrations, minimizing the amount of time taken for diffusion and subsequent protein expression. To summarize, since the ribosomes are captive or immobilized to the device or substrate and near the mRNA "feed points", expression is optimized and can be increased by: (1) increasing mRNA concentration, (2) supplying polymerized or concatenated repeats of mRNA sequences, (3) lowering pore diffusion or transport impedance, or (4) applying concentration, chemical, electrostatic, or other motive gradients.

Another benefit of the above approach is that once the translation process has expended enough energy sources (or created enough inhibitory byproducts) that reduce the translation rate significantly, the translation products and reactants can be washed out of the reaction module, leaving concentrated mRNA (or DNA with transcription mixture) and linked ribosomes to interact with a fresh aliquot of translation mixture from Input 2 (FIG. 1). In some aspects, the washing is performed in discrete volumes upon demand, or via continuous infusion. It should be noted that this method of using a porous membrane for in vitro protein synthesis differs significantly from other ideas ([Siuti et al., Lab Chip 11(2): 3523-3529 (2011)], [Siuti et al., Anal Chem 84(2): 1092-1097 (2012)], [Timm et al., Small 12(6):810-7. doi: 10.1002/smll.201502764., 2015]) that use porous membranes to keep nucleic acid template and transcription/translation mixtures together, but allow the exchange of metabolites, energy, and inhibitory byproducts with a fresh source stream. The present disclosed CFPS system purposely draws the nucleic acids through the porous membrane to subsequently react with the ribosomes and translation chemistry. This approach is advantageous, since the total flux of mRNA through the pores and into the translation side of the reaction chamber may be controlled to regulate the effective protein synthesis rate. For instance, local depletion of necessary translation components can be reduced by lowering the mRNA flux as well as increase the flux of translation solution (FIG. 1, Input 2). In this instance, the translation mixture (minus all or part of ribosomes) may be included in the nucleic acid template solution (FIG. 1, Input 1) to reduce localized depletion. An additional benefit is that the mRNA fragments are forced to flow through a region of tethered ribosomes at the pore that otherwise may not be accessible from the bulk volume because of steric hindrance of having the ribosomes relatively close to a substrate.

FIG. 4 illustrates ribosomes tethered to nanoparticle (or microparticle) substrates within the reaction module. Nanoparticles in some aspects are tactically positioned in the chamber using various force fields, including—but not limited to—magnetic force induced by permanent magnets or electromagnets on paramagnetic particles, electrophoretic or dielectrophoretic forces induced by static or alternating electric fields on particles of various materials (e.g., metal, polymer, semiconductor, etc.), acoustic radiation forces on particles of any material induced by acoustic focusing devices, optical force on particles of any material induced via optical tweezers. These positioning methods are used in some aspects to distribute the particle-ribosome complexes within the reaction module's bulk volume in ways that would optimize ribosomal interaction with mRNA fragments and the translation mixture. Without being bound to a particular theory, levitating the particles within the reaction module reduces the effects of steric hindrance found at a fixed substrate. In some aspects, the particles are small enough and the tethers between the particles and ribosomes are long enough to reduce steric hindrance at the particles themselves. In some aspects, the force field is manipulated to create a periodic variance of particle position in time to enhance ribosomal interactions with the mRNA and translation mixture by ensuring fresh reactants are provided to the ribosomes before depletion occurs. During wash steps, the aforementioned force fields may be used to keep the particle-ribosomes complexes within the reaction module and then redistribute them when fresh translation mixture and mRNA are infused. In alternative or additional aspects, the infusion process is constant with the particle-ribosomes complexes levitating (with time varying positions or stationary) within the reaction module.

In exemplary instances, magnetic micro- or nanoparticles conjugated with ribosomes are used in bead-based chemistries to perform protein translation in a vessel. An external magnet in some aspects is used to ensure ribosomes are not lost when exchanging reactants or collecting protein product. The vessel in certain instances is placed in a magnetic or electromagnetic field that would continuously mix the particle-ribosome complex during translation to ensure fresh reactants are available, thus creating a higher protein generation rate.

FIG. 5 shows how ribosomes (or particle-ribosome complexes) in various aspects are attached directly to a substrate (a) or 2D or 3D matrix (b) of any material via linkers/tethers. The method shown in FIG. 5(a) is a simple method to create a reaction module that contains reusable ribosomes or ribosomal parts. However, such a system in certain aspects may suffer from steric hindrance and local depletion of reactants at the interface between the substrate and liquid. Adding a 3-dimensional (3D) lattice greatly increases the surface area and interactions between the ribosomes, translation mixture, mRNA—resulting in a faster translation rate per unit volume. In some instances, localized depletion still occurs at ribosomal sites, but constant perfusion of mixture alleviates this issue by providing fresh reactants and washing away inhibiting byproducts. In various instances, ribosomes are attached to the external surfaces of the lattices or are contained within a permeable lattice (i.e., polymerized within a hydrogel [Blanchette et al., *Nature communications,* 7, 11900 (2016)] https_colon_forward slash_forward slash_doi.org/10.1038/ncomms11900]). Particle-ribosome complexes are used in various aspects to ensure ribosomes remain within the boundaries of the hydrogel/polymer material or within the lattice of any material.

Exemplary Filtration Modules

In various instances, the filter module in FIG. 1 is used to remove reaction byproducts and unused reactant from the reaction module to create a purified target protein product. The filter design itself in various aspects incorporates an H-filter to separate the larger target proteins from smaller reactants and byproducts via differences in diffusion rates in laminar flow (FIG. 6) [Brody and Yager, Sensors Actuators A Phys 58(1): 13-18 (1997)]. In alternative or additional aspects, porous membrane filters, gel electrophoresis channels, capillary electrophoresis columns, dielectrophoresis with alternating [Washizu et al., IEEE Trans Ind Appl 30(4): 835-843 (1994)] or static [Lapizco-Encinas et al., J Chromatogr A 1206(1): 45-51 (2008)] electric fields, isoelectric focusing [Hofmann et al., Anal Chem 71(3): 678-686 (1999)], dialysis [Song et al., Anal Chem 76(8): 2367-2373 (2004)], or a combination of the aforementioned, is used to separate the larger target proteins from smaller reactants and byproducts. Said aspects may be integrated on the same microfluidic chip as the reaction module (e.g., lab-on-a-chip) or manifested in a separate module that is connected through standard fluidic tubing and components.

In various instances, the filtration process itself provides the benefit of inherently concentrating the target product (e.g., dialysis [Song et al., 2004, supra]). However, an additional module may be used to concentrate the product independent of the filtration module's operating parameters. In some aspects, concentrating proteins via electrokinetics is used since the electric field forces are relatively strong compared to other forces at the micro and nanoscale regimes. In some aspects, electrokinetic methods include free-flow isoelectric focusing [Kohlheyer et al., Anal Chem 79(21): 8190-8198 (2007)], combination electrophoresis with nanoporous membranes [Khandurina et al., Anal Chem 71(9): 1815-1819 (1999)], hydrogel plugs [Dhopeshwarkar et al., Lab Chip 5(10): 1148-1154 (2005)], or nanofissures in polymer materials [Kim et al., Anal Chem 78(14): 4779-4785 (2006)].

Exemplary Reaction Module Fabrications

As previously mentioned, the protein generation system is in some aspects realized in the microfluidic regime. FIG. 7 illustrates one of many possible fabrication techniques used in creating the reaction module with the nanoporous membrane, per FIG. 3. In certain instances, a membrane comprised of aluminum oxide ($Al_2O_3$) is desirable, as it has shown to be more robust and easier to fabricate than with other materials [Venkatesan et al., Adv Mater 21(27): 2771-2776 (2009)]. In various instances, a thin layer of aluminum oxide is deposited on a silicon (Si) wafer, followed by a thin layer of silicon nitride (SiN). In various aspects, the $Al_2O_3$ membrane is created by etching a window in the SiN, followed by etching a complementary window on the back side of the Si wafer. A single micro/nanochannel or an array of said channels in certain instances is created through drilling by transmission electron microscopy (TEM) [Venkatesan et al., 2006, supra] or focused ion beam (FIB) [Lo et al., Nanotech 17(13): 3264 (2006)] or by etching via controlled dielectric breakdown [Kwok et al., PLoS One 9(3): 2014); e92880]. In certain aspects, conventional photolithography, nanoimprint lithography [Chou et al., J Vac Sci Technol B 14(6): 4129-4133 (1996)], or electron beam lithography [Vieu et al., Appl Surf Sci 164(1): 111-117 (2000)] techniques are used to pattern the channels before a wet or dry etch.

FIG. 8 illustrates how the reaction module is completed by sandwiching and bonding the membrane in FIG. 7 between two channel layers. In certain instances, this allows the inflow of reactants and outflow of products and byproducts in addition to fluidically connecting the reaction module with other modules up and downstream on a microfluidic device. For example, the proteins and byproducts from the outlet of the top chamber may be routed to a dialysis chamber to concentrate the target protein. Electrodes in some aspects are patterned on the channel walls of the reaction module to control infusion rates of the nucleic acids in Input 1 via electrophoresis and/or electroosmotic flow.

Simpler reaction chamber designs (FIGS. 4 and 5(a)) may be fabricated using standard microfabrication technique as shown in FIG. 9. In certain instances, fluidic channel patterns are created in exposing and developing photoresist before etching the silicon or glass substrate with a wet or dry etch. The channels are in some aspects hermetically sealed by bonding two wafers together. In various aspects, less expensive manufacturing methods are used to create the fluidics, such as injection molding [McCormick et al., Anal Chem 67(14): 2626-2630 (1997)], hot embossing [Becker and Heim, Sensors Actuators, A Phys 83(1): 130-135 (2000)], and laser ablation [Roberts et al., Anal Chem 69(11): 2034-2042 (1997)] of plastics/polymers and other materials. Also, in some aspects, additive manufacturing methods such as stereo lithography (SLA) and 3D printing are employed to combine fluidics and matrices as a single part.

FIG. 5(b) shows a lattice reaction chamber design, which may be created in many ways. In exemplary aspects, the simple chamber in FIG. 9 is filled with microspheres before sealing it, or microspheres are in various aspects flowed into the chamber after it is sealed (FIG. 10) [Wang et al., Rapid Commun Mass Spectrom 14(15): 1377-1383 (2000)], with filters (mechanical, electrical, magnetic, etc.) ensuring beads are localized to the reaction chamber (see FIGS. 22, 24, and 25). A possible benefit of the latter packing method allows beads to be functionalized with ribosomal tethers off-chip before being injected into the chip, in various aspects. This would alleviate issues found in the laminar flow domain of microfluidics, where necessary mixing is slow and limited to molecular diffusion. In various aspects, a system is created via selectively polymerizing a hydrogel or other polymer inside the sealed reaction chamber [Beebe et al., Nature 404(6778): 588-590 (2000)]. In some instances, uncured polymer is flowed through the chip and selectively cross-linked in the reaction chamber with ultraviolet light that is patterned by photomask. In certain aspects, any uncured polymer is evacuated from the chip, leaving a system with pore sizes that can be controlled through modifying the polymer's composition and cross-linking methods [Hoffman, Adv Drug Deliv Rev 64 (Suppl): 18-23 (2012)], [Ozmen and Okay, 46(19 Spec Iss): 8119-8127 (2005)]. Ribosomes or ribosomal parts in various instances are then attached to the polymerized matrix using various attachment chemistries and other methods.

In various instances, ribosomes are also encapsulated within the polymer before cross-linking, similar to [Blanchette et al., 2016, supra]. A hydrogel with encapsulated ribosomal parts is used in certain instances in a non-microfluidic domain. In some aspects, after polymerization, a hydrogel with encapsulated ribosomes or ribosomal parts is incubated in a vessel or flow cell containing nucleic acids and necessary protein translation reactants. The vessel or flow cell is in certain instances shaken to create chaotic mixing and enhance the diffusion of fresh reactants to the hydrogel. The vessel's size and shaking velocity in some instances is controlled to ensure a high enough Reynold's number for chaotic mixing conditions.

In various aspects, systems are created in the reaction chamber via arrays of pillars or other objects to increase the surface area and biomolecular interactions [Watkins et al., Sci Transl Med 170(214): 214ra170 (2013)] (FIG. 11). The pillars illustrated in FIG. 11 are in some instances created by anisotropic etching of silicon, but in some aspects may be patterned in other materials. Laser ablation, injection molding, or hot embossing is used in certain instances to create the pillar arrays and supporting fluidics in plastics or other polymers.

In various aspects, an alternative to vertical pillars, a series of micro- or nanoporous membrane walls [Timm et al., 2016, supra] orthogonal to the flow of reactants increase surface area and force the mRNA to interact with the tethered ribosomes (FIG. 12). In various instances, a combination of electron beam lithography reactive ion etching is used to create lateral pores in silicon walls; pore size is precisely tuned via plasma-enhanced chemical vapor deposition (PECVD) and atomic layer deposition (ALD) of silicon dioxide [Shankles et al., J Vac Sci Technol B 33 (6): 06FM03 (2015)].

In certain instances, vertically-aligned carbon nanotube (VACNT) forests provide relatively high surface area per volume and are grown directly on various substrates using various forms of PECVD [Ren et al., Science 282 (5391) 1105-1107 (1998)], [Stadermann et al., Mech Eng 78(16): 5639-5644 (2006)]. In certain instances, these forests are directly grown in the microfluidic channels that comprise the reaction chamber [Stadermann et al., 2006, supra], grown on a flat surface that would be encapsulated by the microfluidic channels, or grown on both surfaces before sealing the chamber to maximize surface area. The following an exemplary implementation of using nanotubes to enhance off-chip protein synthesis and the advantages thereof.

In various aspects, aerogels are used in the CFPS systems presently disclosed. Aerogels are synthetic porous bulk materials that provide an even higher surface area per unit volume than nanotube forests by providing true 3-dimensional porous fluidic systems with surface areas that exceed 2,000 $m^2$ per g of material [Biener et al., Adv. Mater., 24:5083-5087 (2012)]. Aerogels can be cast or machined (e.g., laser cut, dicing saw, scribe and cleave, etc.) into the appropriate shape for a CFPS flow cell. Even though in some instances much of this surface area cannot be used because it consists of micro- and mesopores features that are smaller than the diameter of ribosomes, the surface area from the macropores still provides an order of magnitude larger than that of VACNT forests. For example, a mostly macroporous (0.5 to 1 μm pore size) aerogel provides up to 110 $m^2$ per g of material [Kovalenko et al., J. Porous Mater., 25:1017-1026 (2018)]. Given the density of graphene to be 0.56 g per mL, an aerogel in some aspects provides 61,600 $mm^2$ per μL vs. 6,150 $mm^2$ per μL for a VACNT that has similar effective spacing of ~500 nm. The latter was calculated from 175 nm diameter, 50 μm tall CNTs at a density of $2.2 \times 10^8$ per $cm^2$. Even the maximum surface area per volume of 11,000 $mm^2$ per μL for VACNTs with minimal spacing to be practiced with ribosomes (spacing of ~50 nm from 175 nm diameter, 50 μm tall CNTs with $2 \times 10^9$ per $cm^2$ density) is considerably less than an aerogel. In addition, the surface area of the aerogels can be further increased by reducing the macropore size to the practical limits for handling ribosomes (~50 to ~200 nm).

Exemplary Nanotube Linkers

In some aspects, nanotubes are used as linkers/tethers, which have several advantages over nucleic acid linkers. The nanotubes (1) are mechanically stronger [Kim and Kim, PLoS One 11(4): e0153228 (2016)], [Yu, Science 287 (5453): 637-640 (2000)]; (2) are more chemically resistant; (3) have a larger length-to-diameter ratio [Wang et al., Nano Lett 9(9): 3137-3141 (2009)]; (4) have diameters that are controllable in addition to their lengths (nucleic acids share the latter); (5) provide attachment sites for ribosomes or other entities not only at their ends (e.g., the 3' and 5' ends of DNA), but all along their lengths as well. This last advantage greatly increases ribosomal density in the reaction module when compared to using end-only attachment sites. For example, a biotin-streptavidin system to attach ribosomes to single walled carbon nanotubes (SWNTs) would give approximately a ribosome for every 20 nm of nanotube length for nanotubes with 1.3 nm diameters [Liu et al., J Phys Chem C 114(10): 4345-4352 (2010)]. A 5 μm long SWNT of said diameter would provide on the order of 250 ribosome attachment sites. The diameter of the nanotubes in some aspects is increased to provide more carbon atoms and resulting attachment sites per unit length. Larger diameters also give the mechanical stability to increase length and provide even more attachment sites. As a result, a 20 nm-wide multi-walled carbon nanotube (MWNT) that is 20 μm long may have as many as 23,000 ribosomes attached to it. In self-assembled monolayer (SAM) surface chemistries, surface attachment sites are on the order of $10^{14}$ per $cm^2$ [Wayment and Harris, Anal Chem 78(22): 7841-7849 (2006)], [Dubois and Nuzzo, "Organic Surfaces" 43: 437-463 (1992)]. The surface attachment sites in some aspects are reduced [Wayment et al., 2006, supra] to ensure access of mRNA and other translation components to the ribosome subunits within the CNT forest. Assuming a CNT density of one 20 µm-long, 20 nm-wide CNT every 1,600 nm$^2$, a 1 cm$^2$ protein generation region (i.e., FIG. 9) could contain 6.3× 10$^{10}$ CNTs. This would result in 9.6×10$^{14}$ ribosomes. For comparison, a single E. coli cell contains approximately 7.2×10$^4$ ribosomes during a rapid growth rate [Dennis and Bremer, 1996, supra]. Assuming the protein generation module is a 1 cm×1 cm×20 µm (2 µL) volume and the maximum E. coli concentration during the log growth phase (just before transition to stationary phase) is 2×10$^9$ cells per mL, the presently disclosed CFPS system that incorporates a cell-free protein generation method with CNT-ribosome systems has the potential to produce target proteins at the same rate of conventional cell fermentation methods but using over 3,300 times less volume. For perspective, the on-chip volume needed to replicate the processing rate of a 12,000 liter E. coli fermenting tank would be 3.6 L in a microfluidic device. This assumes that mRNA and other reagents are able to be fed to (and protein and waste products are able to be withdrawn from) the CNT-ribosomal network at optimal rates. Assuming a translation rate of 21 amino acids per second for each ribosome [Dennis and Bremer, 1996, supra] and an average amino acid mass of 110 Da, a 1 cm$^2$ reaction module footprint would produce 319 mg of protein product per day.

Figure 13:
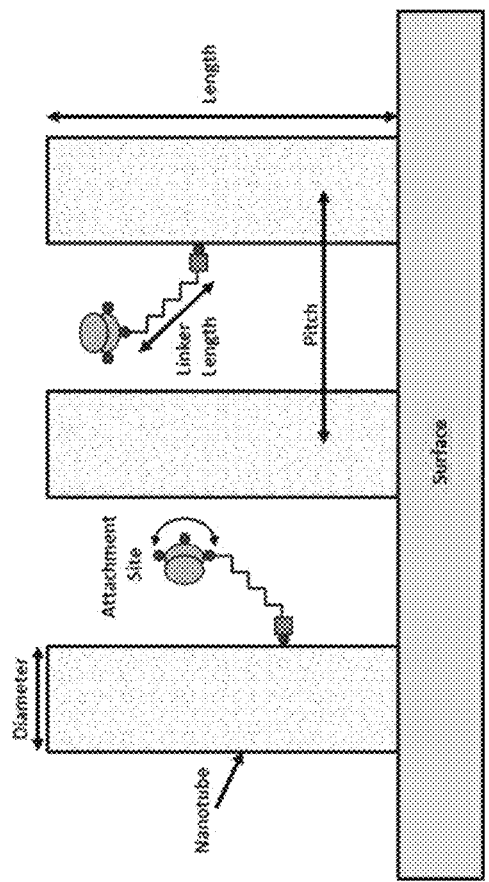
FIG. 13 is an illustration depicting a vertically-aligned carbon nanotube forest showing several parameters that may affect protein generation efficacy.

FIG. 13 illustrates the nanotube forest modified to maximize protein generation efficiencies and rates. Some parameters include nanotube diameter, nanotube length, nanotube pitch, nanotube chirality, length of linkers between nanotube and ribosome subunits, and attachment orientation of ribosomal subunits. In some aspects, nanotubes are conjugated with either the small or large subunits or a mixture of both complementary subunits (eukaryotic, cytoplasmic: 60S/40S; eukaryotic, mitochondrial: 39S/28S; prokaryotic: 50S/30S). The concentration of ribosomes, linking chemistry reactants, and translation chemistry reactants are also parameters that may be modified. The success of a particular set of parameters may be measured by quantifying target protein concentration with a liquid chromatography (LC), mass spectrometry (MS), or both where the LC output feeds into the mass spectrometer (i.e., LC-MS). Protein production may be verified qualitatively by generating fluorescing proteins, such as green fluorescent protein (GFP), and observing fluorescence intensity. Fluorescent tags specific to target proteins may also be used.

The above is not limited to planar surfaces. Lattices, matrices, bead columns, and other methods with various materials may be used to increase surface area for nanotube attachment within a particular volume.

As a comparison, a gel-enapsulated ribosomal system in the spirit of [Blanchette et al., Nature Communications volume 7, Article number: 11900 (2016)] in some aspects provides an alternative to the nanotube-based tethering system. Using similar concentrations of the 1.3 MDa prokaryotic ribosome subunit 50S as pMMO enzyme used in [Blanchette et al., 2016, supra] (1 µg/µL) with 85% retained in the gel, approximately 7.9×10$^{11}$ 50S subunits in a 1 cm×1 cm×20 µm gel. Although the ribosomal density is several orders of magnitude less than that found in the CNT method for the same volume, the thickness may be increased to provide a higher ribosomal density per cm$^2$. In some instances, a membrane of 10 mm thickness would result in ~131 mg of protein generated per day for each 1 cm$^2$ of gel matrix.

The following examples are given merely to illustrate the present invention and not in any way to limit its scope.

EXAMPLES

Example 1

This example describes the manufacture of an exemplary CFPS system and its use in manufacturing proteins through in vitro translation (IVT) reactions.

Figure 14:
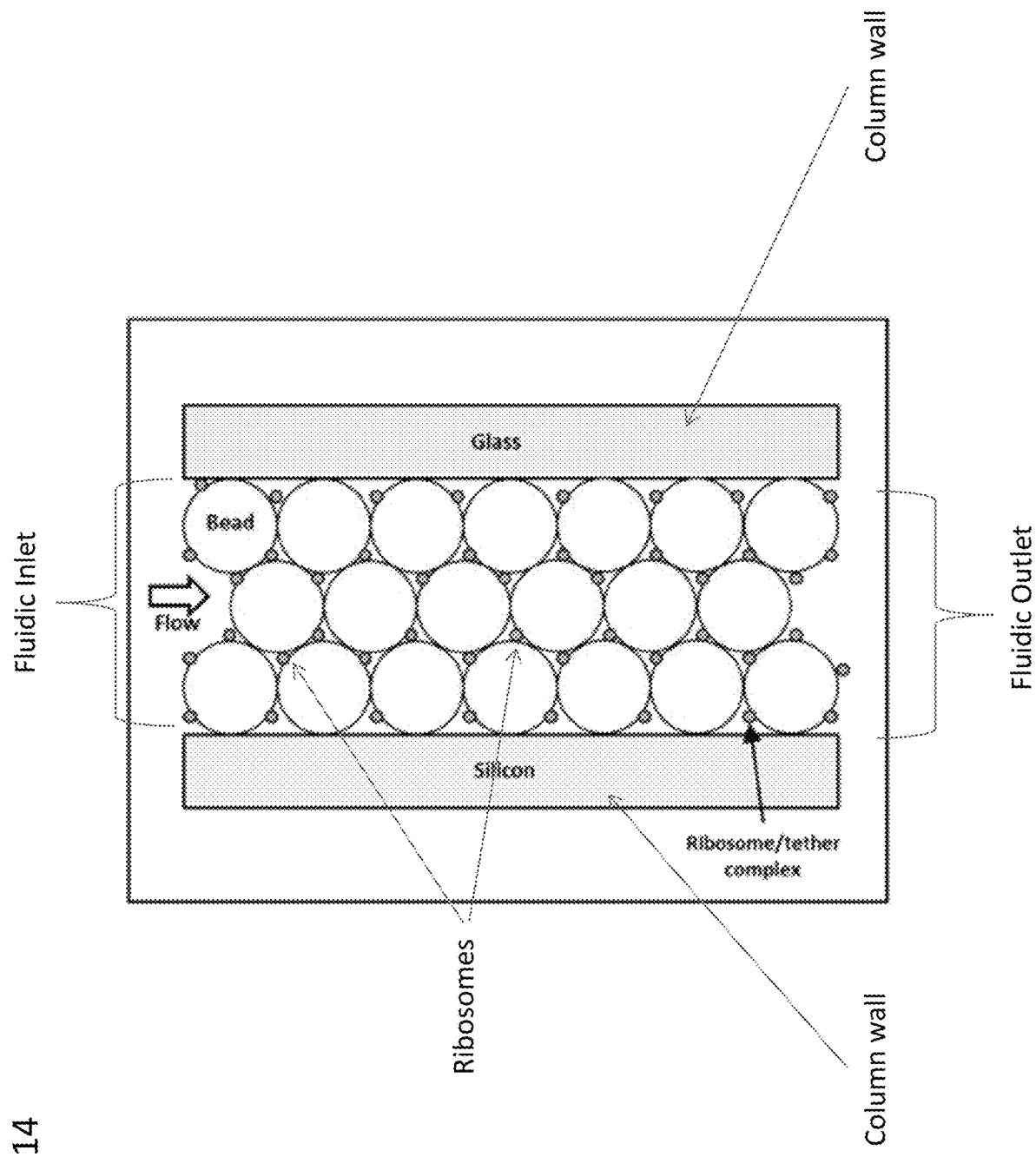
FIG. 14 is an illustration depicting a column packed with ribosome-attached beads.

Streptavidin-coated microbeads (ThermoFisher, 20361) were labeled with biotinylated E. coli ribosomes to produce an exemplary CFPS system of the disclosure. An illustration of the beads is shown in FIG. 14.

Biotinylated ribosomes were first made by incubating E. coli ribosomes with sulfo-N-hydroxysulfosuccinimide (sulfo-NHS)-modified biotin molecules with 22.4 Å spacer arms (ThermoFisher, A39257) for 48 hours at 4° C. Multiple biotins were attached to each 70S ribosome unit through accessible lysine and arginine residues of the 70S unit. Successful biotin attachment onto ribosomes was verified with a fluorescence biotin quantitation kit (46610, ThermoFisher). Biotinylated ribosomes were then incubated with streptavidin beads (20361, ThermoFisher) for two or three days at 4° C., followed by thorough washing to remove unattached ribosomes. The attachment of biotinylated ribosomes to beads was determined as described in Example 2 below.

A control was made by incubating non-biotinylated ribosomes with streptavidin beads and placing this mixture into a 1.5 mL centrifuge tube. The tube contents was thoroughly washed to remove unattached ribosomes.

A custom-designed plasmid encoding the mCherry protein with a histidine tag (his-mCherry) was made. For IVT reactions, a 25 µL solution containing the his-mCherry plasmid along with the components in the PURExpress Δ Ribosome kit (E3313S, New England Biolabs) were added to (A) a 1.5 mL centrifuge tube containing 30 µL streptavidin-coated microbeads labeled with biotinylated E. coli ribosomes or (B) a 1.5 mL centrifuge tube containing 30 µL of the control mixture of non-biotinylated ribosomes and beads. The IVT reactions took place overnight at 37° C., and the IVT reactions were quenched by placing tubes on ice. The reaction mixture was next centrifuged for 10 s at 2000×g to separate the beads from the supernatant containing the his-mCherry protein, and the supernatant was collected. Pellets containing beads were washed with ribosome washing buffer: 20 mM Tris solution (pH 7.5 to 8) containing 10 mM magnesium acetate, 30 mM potassium chloride, and 7 mM 2-Mercaptoethanol.

Proteins from the supernatant were separated by SDS-PAGE and immunoassayed by Western blotting with an mCherry primary antibody (AB356482, Millipore-Sigma) coupled to a fluorescent secondary antibody (925-68071, Licor). Fluorescence was measured using a Licor Near-Infrared gel imager (Li-Cor Odyssey CLx, Lincoln, NE).

The IVT reactions were repeated by washing and spinning down the beads, removing ribosome washing buffer, and adding 25 µL of new IVT buffer containing his-mCherry plasmid along with the components in the PURExpress Δ Ribosome kit and incubating as described above.

Figure 15:
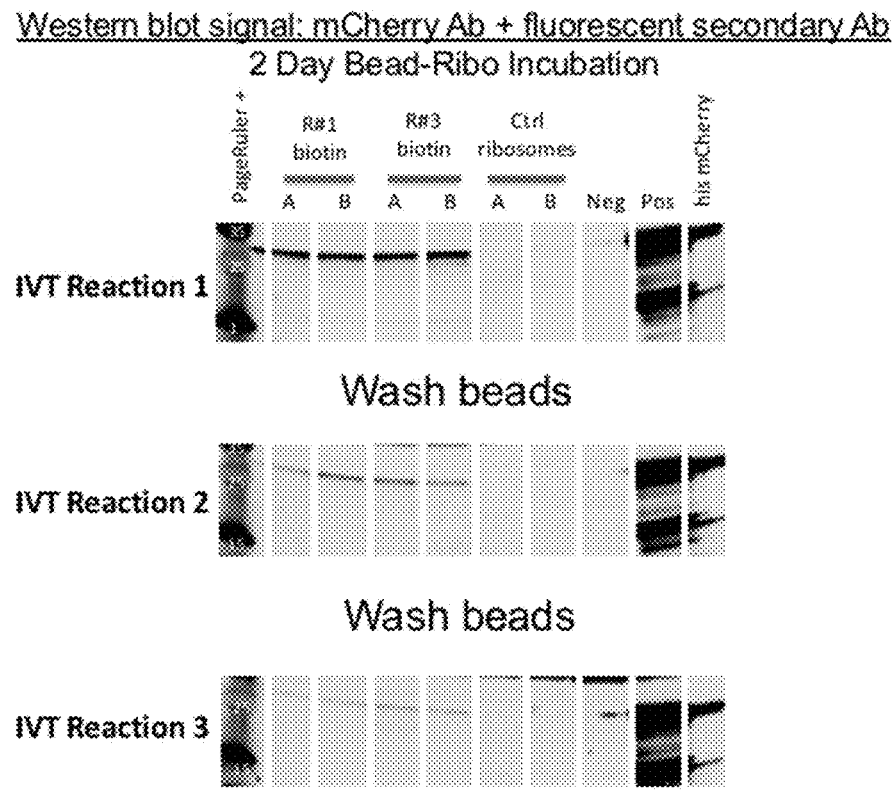
FIG. 15 is a Western blot using mCherry antibody (ab) demonstrating protein production after IVT reaction 1 (prior to any wash), IVT reaction 2 (after a single wash of beads), and IVT reaction 3 (after a second wash of beads).
Figure 16:
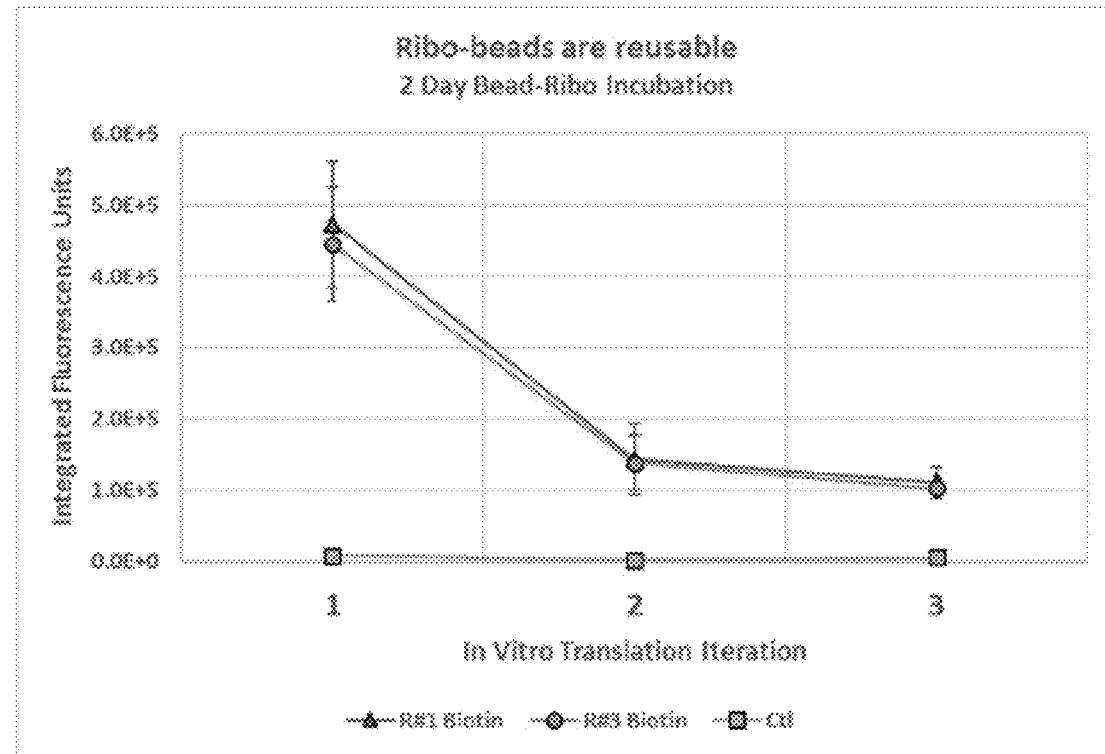
FIG. 16 is a graph of integrated fluorescence units plotted as a function of IVT reaction.

FIG. 15 shows the Western blots of the supernatants after the first, second, or third IVT reaction using streptavidin-coated microbeads labeled with biotinylated E. coli ribosomes, wherein the beads were incubated with the biotinylated ribosomes for two days, or with the control mixture of ribosomes and beads. FIG. 16 is a graph of the fluorescent signal for his-mCherry production after 1, 2, or 3 IVT reactions. As shown in FIGS. 15 and 16, the matrix of ribosome-labeled microbeads achieved successive synthesis of his-mCherry during the initial IVT iteration and also achieved continued synthesis of the protein after two more wash-IVT iterations. These data demonstrate that the CFPS system is functional and advantageously re-useable. While protein synthesis decreases for each iteration, the ribosome-labeled microbeads still achieved significant levels of protein production, relative to control.

Figure 17:
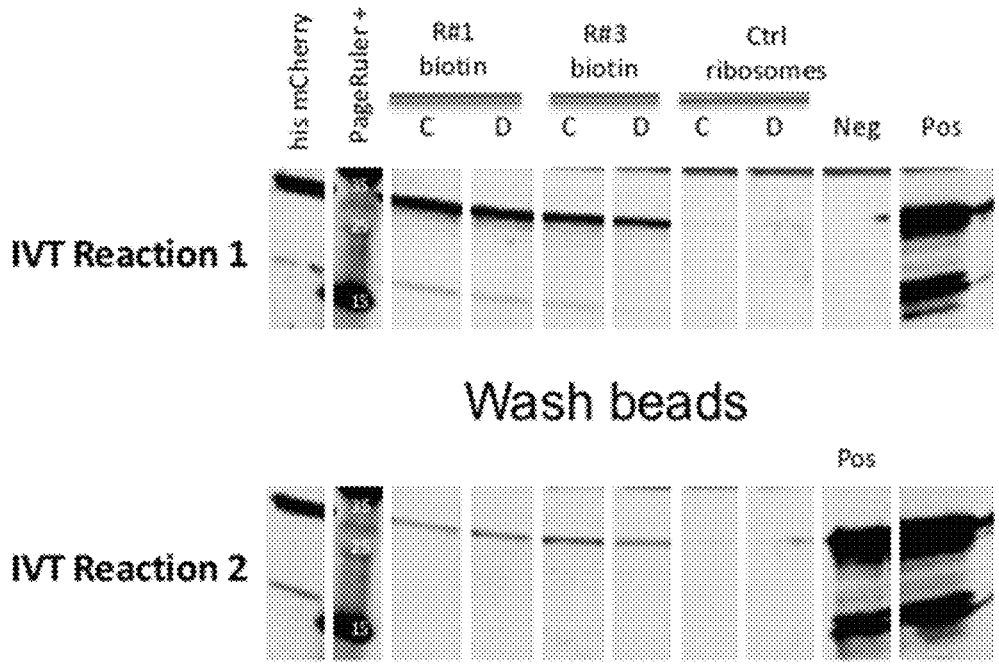
FIG. 17 is a Western blot using mCherry antibody (ab) demonstrating protein production after IVT reaction 1 (prior to any wash) and IVT reaction 2 (after a single wash of beads).
Figure 18:
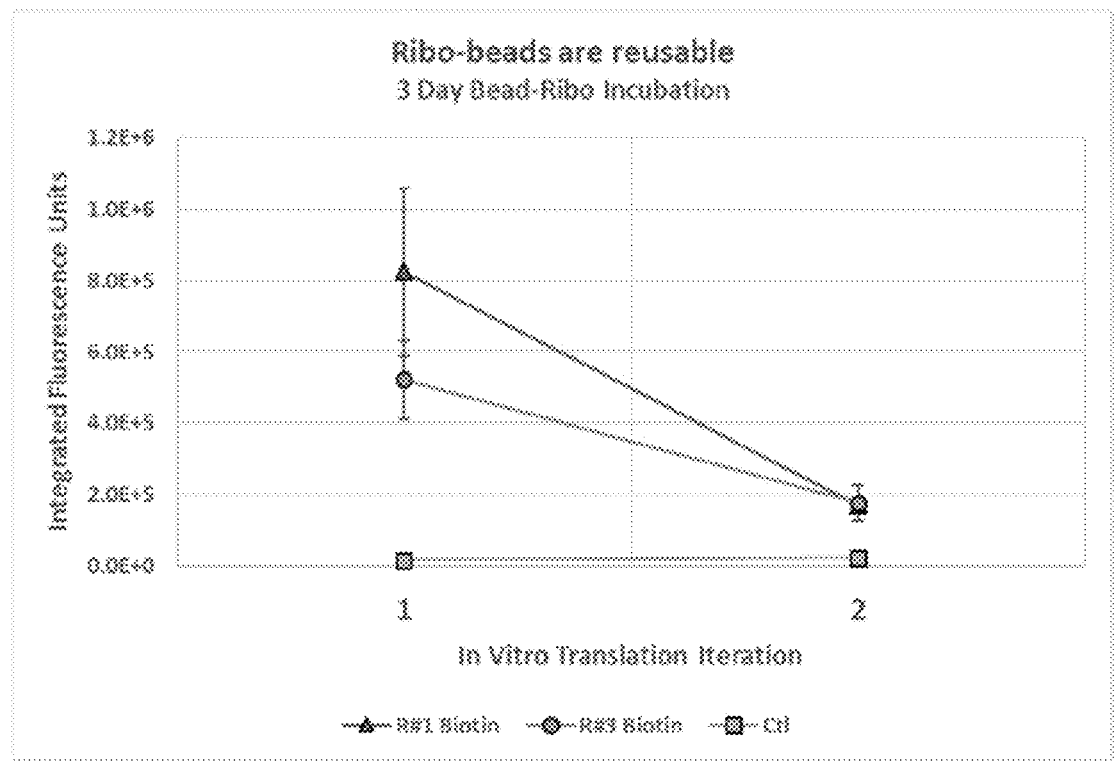
FIG. 18 is a graph of integrated fluorescence units plotted as a function of IVT reaction.

The experiment was repeated only this time streptavidin-coated microbeads labeled were incubated with biotinylated E. coli ribosomes for three days, not two days, as in the first experiment. FIG. 17 shows the Western blots of the supernatants after the first or second IVT reaction using streptavidin-coated microbeads labeled with biotinylated E. coli ribosomes or with the control mixture of ribosome and beads. FIG. 18 is a graph of the fluorescent signal representing his-mCherry production after the IVT reactions. As shown in FIGS. 17 and 18, the matrix of ribosome-labeled microbeads was able to synthesize his-mCherry during the initial IVT iteration and also a subsequent IVT reaction. These data further confirm the reusability of ribosomes.

Collectively, the data from these experiments validate the use of ribosomes localized to a 3-dimensional matrix in repeated IVT reactions to produce protein.

Example 2

This example describes the measurement of ribosome density of an exemplary CFPS system.

Quantification of biotinylated ribosome attachment to beads was determined by comparing the optical absorbance of the supernatant at 280 nm wavelength before and after incubation. The beads were saturated with ribosomes at 0.6 µmol per µL of beads (dry bed volume; packed bead volumes are assumed to be dry bed volume in this document) or roughly 2.5×10⁸ ribosomes per agarose bead (measured mean diameter of 94 µL) or 3.6×10¹¹ ribosomes per µL bead volume. The streptavidin-coated microbeads labeled with biotinylated E. coli ribosomes were placed in a 1.5 mL centrifuge tube before an IVT reaction.

Example 3

This example describes protein production levels of CFPS systems comprising microbeads attached to ribosomes via linkers of varying length.

A first series of ribosome-labeled microbeads, streptavidin-coated beads having varied length linkers are made as essentially described in Example 1, but using NHS-modified biotin molecules having different spacer arm lengths. See FIG. 19. Sulfo-NHS-biotin molecules having spacer arm lengths of 22.4 Å, 30.5 Å, or 56.0 Å are used by reacting ribosomes with sulfo-NHS-LC-biotin (22.4 Å length, ThermoFisher, 21335), sulfo-NHS-LC-LC-biotin (30.5 Å length, ThermoFisher, 21338), and NHS-PEG12-biotin (56.0 Å length, ThermoFisher, 21312), respectively. Briefly, to make biotinylated ribosomes, E. coli ribosomes are incubated with one of the sulfo-NHS-biotin molecule products (having 22.4 Å, 30.5 Å, or 56.0 Å spacer arms) following the procedure described in Example 1. The biotinylated ribosomes are incubated with streptavidin beads (20361, ThermoFisher) for 2 or 3 days at 4° C., followed by washing to remove unattached ribosomes, as essentially describe in Example 1.

For a second series of ribosome-labeled microbeads, streptavidin-coated beads containing a spacer arm of 10.8 Å which terminate in primary amine groups (CarboxyLink™ Coupling Resin, ThermoFisher, 20266) are used to attach to different biotin molecules having different spacer arm lengths. See FIG. 20. The primary amine groups of the beads react with the sulfo-NHS groups of sulfo-NHS-biotin molecules having spacer arm lengths of 22.4 Å, 30.5 Å, or 56.0 Å. CarboxyLink™ Coupling Resin (ThermoFisher, 20266) is reacted with sulfo-NHS-LC-biotin (22.4 Å length, ThermoFisher, 21335), sulfo-NHS-LC-LC-biotin (30.5 Å length, ThermoFisher, 21338), or NHS-PEG12-biotin (56.0 Å length, ThermoFisher, 21312). Biotinylated beads are next reacted with one of the biotinylated ribosomes described for the first series having different linker lengths to arrive at a series of ribosome-bead complexes having linkers ranging in length from 55.6 Å to 122.8 Å by first reacting the biotinylated beads with neutravidin, followed by washing, then incubating with biotinylated ribosomes, following the same procedure described in Example 1. The combinations of biotinylated beads and biotinylated ribosomes yields total linker lengths varying from 55.2 Å to 122.8 Å. The different combinations are shown in the table below:

| Length of Spacer Arm Attached to Biotinylated Ribosome | Length of Spacer Arm attached to biotinylated bead | Length of spacer arm attached to bead | Total approximate distance between ribosome and bead |
| --- | --- | --- | --- |
| 22.4 | 22.4 | 10.8 | 55.6 |
| 22.4 | 30.5 | 10.8 | 63.7 |
| 22.4 | 56 | 10.8 | 89.2 |
| 30.5 | 22.4 | 10.8 | 63.7 |
| 30.5 | 30.5 | 10.8 | 71.8 |
| 30.5 | 56 | 10.8 | 97.3 |
| 56.0 | 22.4 | 10.8 | 89.2 |
| 56.0 | 30.5 | 10.8 | 97.3 |
| 56.0 | 56 | 10.8 | 122.8 |

All numbers are length in angstroms.

For a control group, the ribosome-labeled microbeads of Example 1 are used.

IVT reactions are carried out with each group of ribosome-labeled microbeads and the control group and protein production levels are measured, as essentially described in Example 1. Each group of ribosome-labeled microbeads is measured for ribosome density as essentially described in Example 2. It is theorized that the group having the highest ribosome density will be the same group having the highest protein production levels.

Example 4

This example describes the manufacture of a CFPS system comprising microbeads attached to ribosomes via a mixture of linkers of varying length and the protein production achieved by this system.

Ribosome-labeled microbeads are produced as essentially described in Example 3 except that a mixture of linkers having different lengths is used in a single reaction. Specifically, CarboxyLink™ Coupling Resin (ThermoFisher, 20266) is agarose beads that contain 10.8 Å linkers that are terminated by primary amine groups. These beads are biotinylated with two different spacer arm lengths (sulfo-NHS-biotin, 13.5 Å, ThermoFisher, 21217 and NHS-PEG12-biotin, 56 Å, ThermoFisher, 21312) at equal proportion. These beads are washed and reacted with free-floating neutravidin, creating neutravidin at two different lengths across the beads' surfaces. Next, two different aliquots of E.

coli ribosomes are each biotinylated with the same spacer arms as listed above: one aliquot with 13.5 Å length, the other with 56 Å length. These two aliquots are combined and then reacted with the biotinylated beads, creating ribosome-bead complexes with total spacer arm lengths of 37.8 Å, 80.3 Å, and 122.8 Å. The ribosome-labeled microbeads from Example 1 that have only one length linker (22.4 angstroms) are used as a control.

Ribosome density is measured for each group as essentially described in Example 2. IVT reactions are subsequently carried out with each test group of beads and with the control group. Protein production levels are measured, as essentially described in Example 1.

Example 5

This example describes a CFPS systems comprising microbeads attached to ribosomes loaded into a chromatography column.

Biotinylated ribosomes attached to streptavidin beads are made as essentially described in Example 1 and 1 mL is loaded into an empty 1 mL Bio-Scale™ Mini Cartridge (Bio-Rad, 7324660). The 7 to 12 μm frit pore size ensures the beads will be retained in the column but allow any protein products to pass through.

The column is mounted in a vertical position with the arrow pointed downward. The top screw cap is opened and 1 mL (dry bead volume) ribosome-beads are pipetted into the column. The column is sealed by re-tightening the top screw cap. The column inlet is directly connected to a Luer-Lok syringe that contains 3 mL of ribosome wash solution: 1 M HEPES-KOH buffer with 10 mM magnesium acetate, 30 mM potassium chloride, and 7 mM 2-Mercaptoethanol. In lieu of a syringe and syringe pump, a HPLC pump is used to drive column flow with the appropriate tubing, fittings, and adapters needed to make the fluidic connections. In this case, a sample loop of 3 mL or greater volume is used. The syringe is loaded in a syringe pump and the beads are washed with 3 mL (3 column volumes) of the solution at 0.1 mL/min. Once waste starts flowing out the column's exit port, a 1/16" OD outlet tubing is connected to the exit using adapters and fittings that convert from Luer-Lok male connectors to 1/16" OD tubing. When the washing is complete, the syringe is replaced with a new syringe containing 3 mL of IVT reaction buffer, minus the free-floating ribosomes. The PURExpress Δ Ribosome kit (E3313S, New England Biolabs) recipe and contents, including the DNA plasmid encoding the protein of interest, is scaled up to 3 mL in the appropriate instances. The column is heated to 37° C. with heater tape (BriskHeat, SLCAB10120B) and the IVT mixture is infused at 10 μL/min, the column output (synthesized protein) is collected in an appropriately-sized conical tube. When infusion is complete, a new syringe is loaded with 3 mL ribosome storage buffer, including the same ingredients of the ribosome wash buffer in addition to 6% bovine serum albumin (BSA). Ribosome storage buffer (1 mL) is infused at 0.1 mL/min, and the remaining synthesized protein solution is collected. The remaining 2 mL of ribosome storage buffer is infused at 0.1 mL/min, remove all fluidic connections, plug the ends of the column, and store column at 4° C. until next use.

Example 6

This example describes an exemplary method of manufacturing a CFPS system comprising a chip comprising a packed array of ribosome-bead complexes with fluidic chambers.

Figure 22:
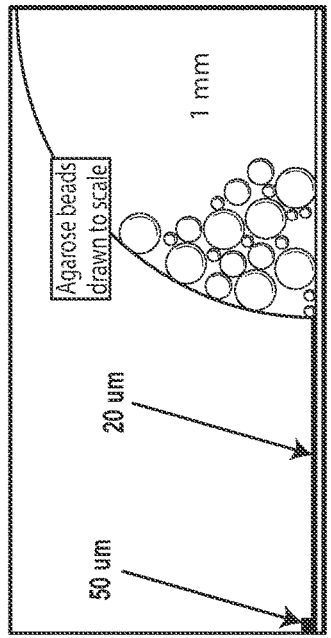
FIG. 22 is an illustration of an enlargement of the boxed portion of FIG. 21 showing the different sized cast inlets/outlets connected to the chamber which holds agarose beads.
Figure 21:
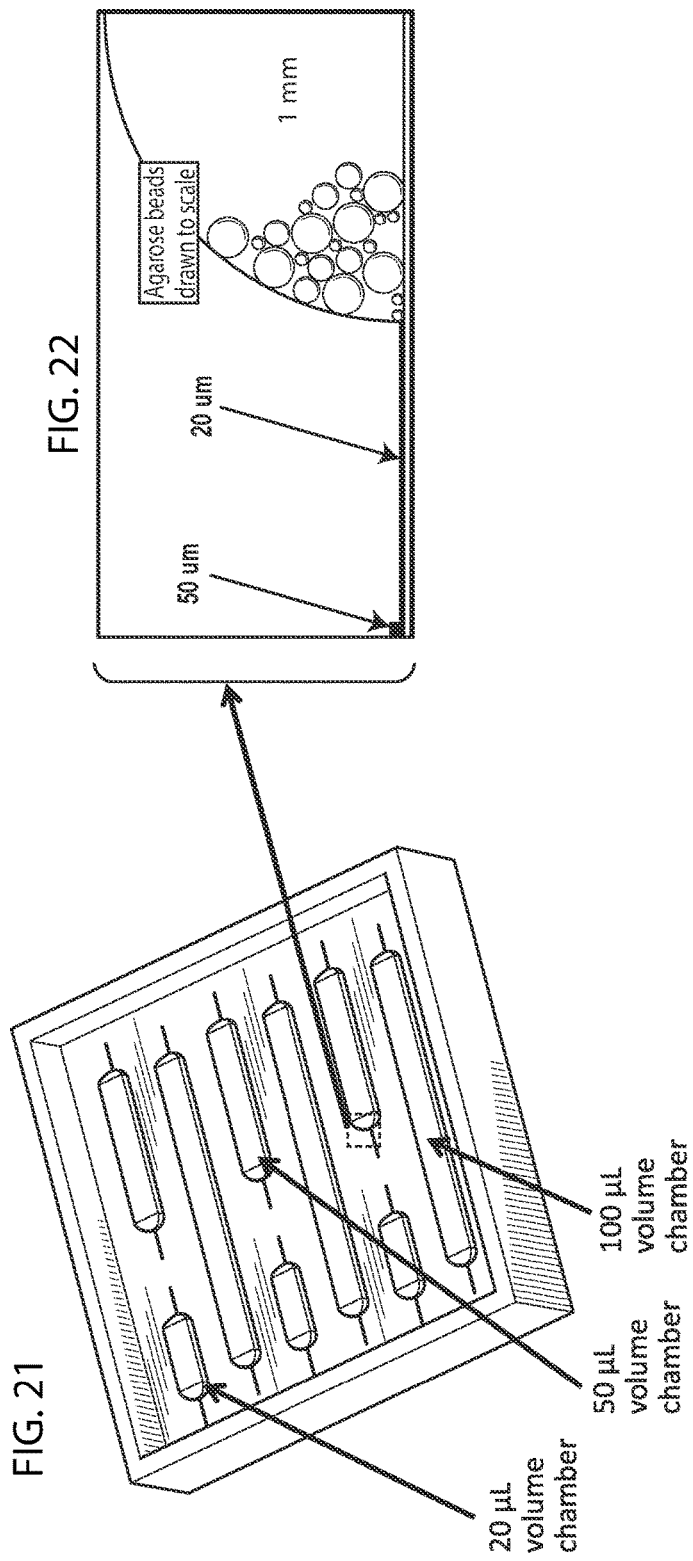
FIG. 21 is an illustration of a cast of a microchip comprising different sized chambers.

Fluidic chambers for on-chip packed arrays of ribosome-bead complexes were designed and fabricated. A negative mold was first created using stereolithography (Formlabs Form 2 SLA printer). FIG. 21 provides a schematic of the mold and shows that the chip was designed to have three different chamber types varying in chamber volume (25 μL, 50 μL, and 100 μL). The chambers were designed to hold agarose beads having a minimum bead diameter of ~40 um. The chip was designed to have two channels at the two opposing ends of each chamber. As shown in FIG. 22, which is an enlargement of the red dotted box of FIG. 21, the channels were designed to have a channel with ~20 μm vertical constriction linked to a channel with a ~50 μm vertical constriction. The channel with ~20 μm vertical constriction functioned as a filter, allowing IVT reactants and products to flow in/out the chamber but preventing the beads from exiting the chamber.

Figure 23:
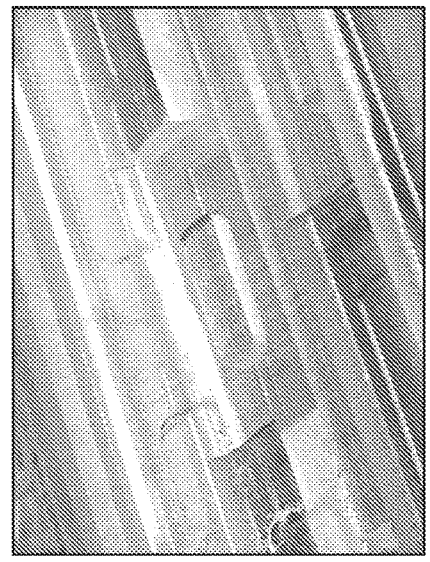
FIG. 23 is a photograph of a portion of the chip made using the cast of FIG. 21.
Figure 25:
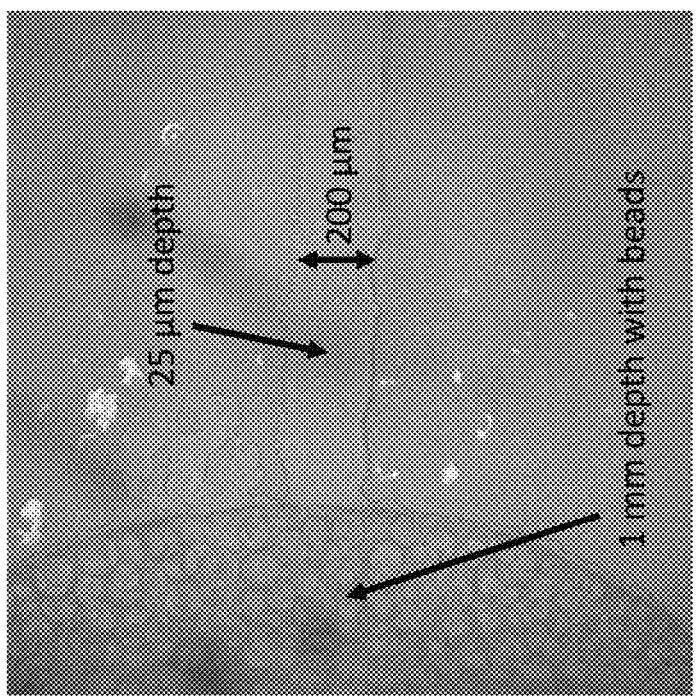
FIG. 25 is a photograph of a microscopic image of the chamber, inlet port and bead loading port referenced in FIG. 24.
Figure 24:
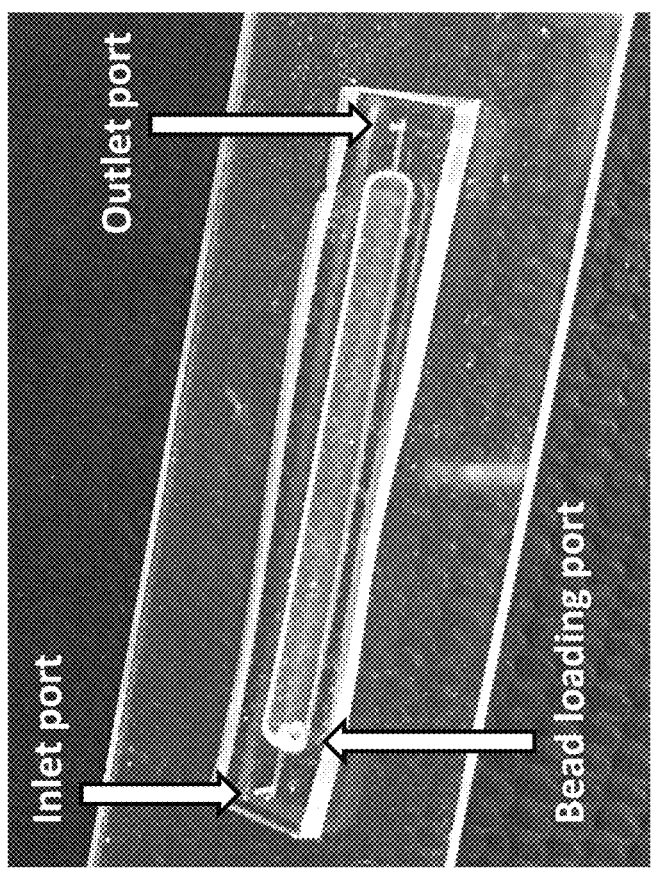
FIG. 24 is a photograph of the different parts of a chip comprising a chamber, an inlet port, a bead loading port, and an outlet port.

A chip was made by pouring polydimethylsiloxane (PDMS), 1:10 curing agent to base ratio, into the mold and curing it for two hours at 80° C. A relief of a 25 μL chamber in the mold is shown in FIG. 23. Inlets and outlet ports were punched at the ends of the PDMS channels. Beads were loaded into each chamber via a larger punched vertical port that bypasses the filters. FIG. 24 illustrates a 100 μL chamber with inlet, outlet, and bead loading port punched out. The bead loading port was then plugged and fluid infusion was carried out through the two filters, delivering surface chemistry and/or IVT solutions to the array. FIG. 25 shows a 100 μL chamber loaded with streptavidin beads (mean diameter was measured to be ~90 μm) that were successfully retained by the 25 μm filter that is between the main chamber and the outlet at the tested flow rate of 20 μL/min.

Figure 26:
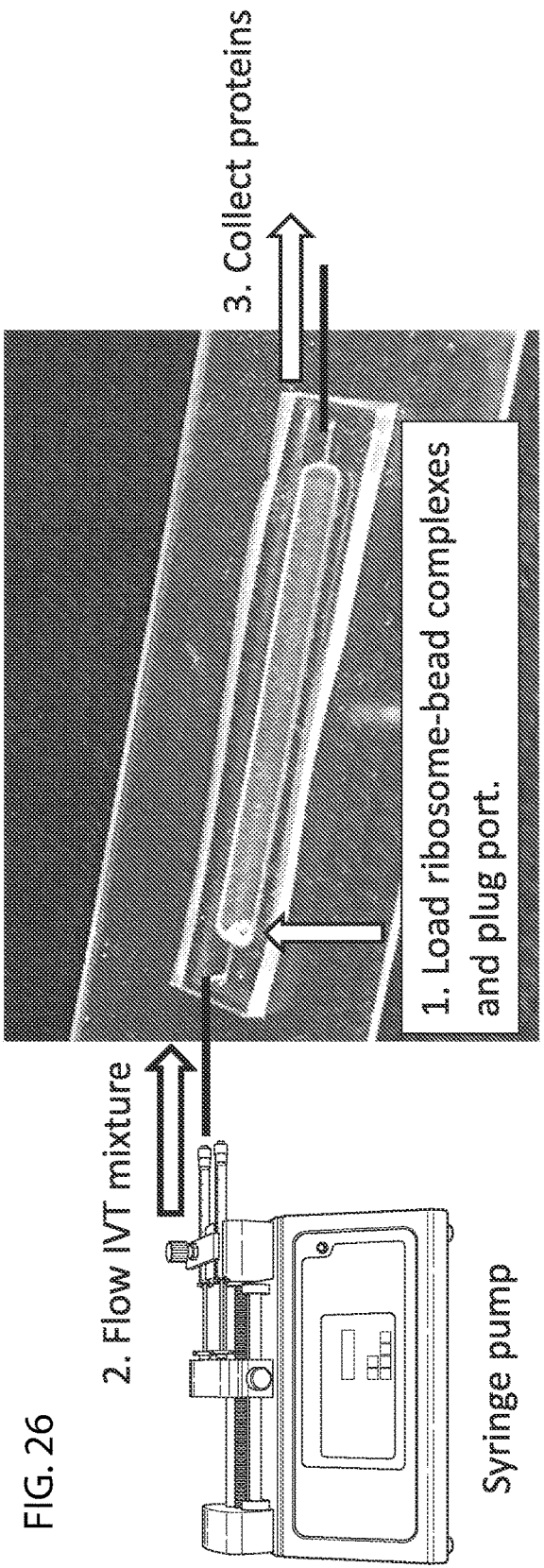
FIG. 26 is an illustration of a basic set-up of a chip described in Example 6, wherein the chip comprises a chamber, inlets and outlets with a syringe pump for IVT protein production.

FIG. 26 illustrates a basic setup for on-chip IVT of proteins using a syringe pump and a 100 μL chip containing ribosome-bead complexes. First, 100 μL of ribosome-bead complexes would be loaded into the main chamber, followed by plugging the bead loading port with knotted tubing. Second, 300 μL of ribosome washing solution (recipe described in Example 4, Step 4) is infused through the chip. Third, the chip is heated to 37° C. using a hotplate or microscope slide heater. Fourth, 300 μL of IVT mixture without free-floating ribosomes was loaded into a new syringe and infused through the chip at 1 μL/min while collecting the protein product in a centrifuge tube at the chip outlet. The IVT mixture are created by scaling the PURExpress Δ Ribosome kit (E3313S, New England Biolabs) recipe and contents, including the DNA plasmid encoding the protein of interest, to 300 μL. Fifth, a new syringe is loaded with 300 μL ribosome storage buffer (recipe described in Example 4, Step 9); 100 μL is infused through the chip to collect the remaining synthesized protein. Sixth, the remaining 200 μL is infused through the chip to waste, the chip's inlet and outlet are plugged, and the chip is stored in a humid environment at 4° C. for future use.

Figure 27:
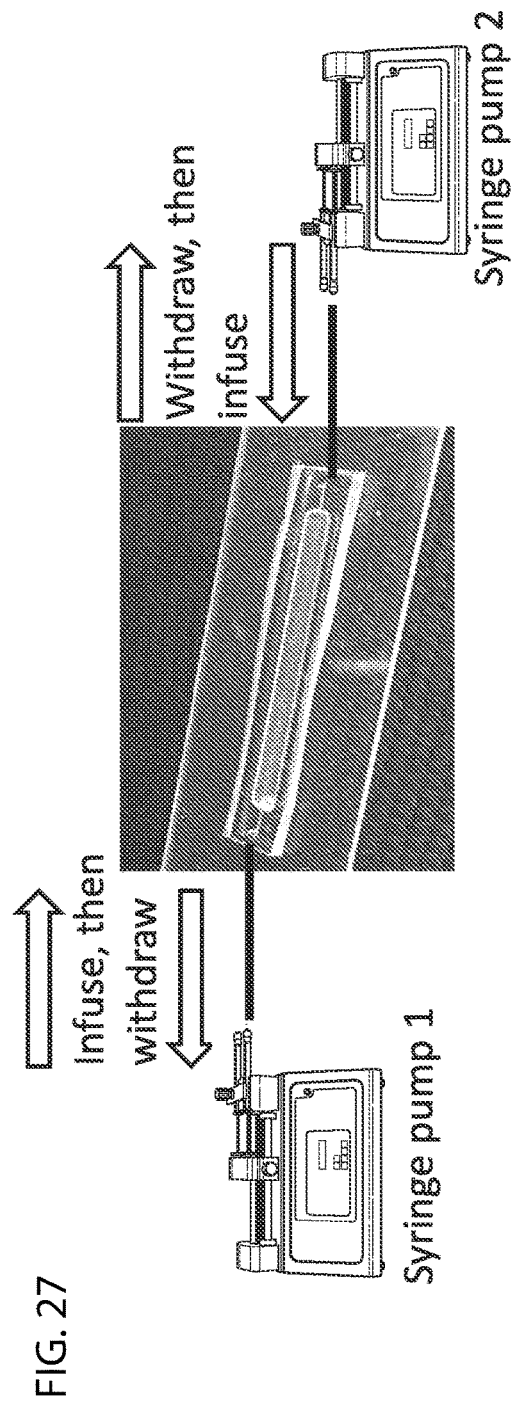
FIG. 27 is an illustration of a different set-up comprising two syringe pumps synchronized to infuse and withdraw fluid volume simultaneously.

A different setup comprising two syringe pumps may be used to recirculate the IVT mixture to increase its interaction with the ribosome-bead matrix, possibly synthesizing more protein than the single-iteration flow setup, described above. FIG. 27 illustrates this setup, where pump 1 and pump 2 are synchronized to infuse and withdraw 300 μL simultaneously, respectively. Flow is then reversed (pump 1 is withdrawing, pump 2 is infusing) and this cycle can be repeated overnight or longer at 37° C. The protein product would be collected from the two syringes and from the chamber's outlet while it is being washed it with 100 μL of ribosome storage buffer.

Example 7

Figure 28:
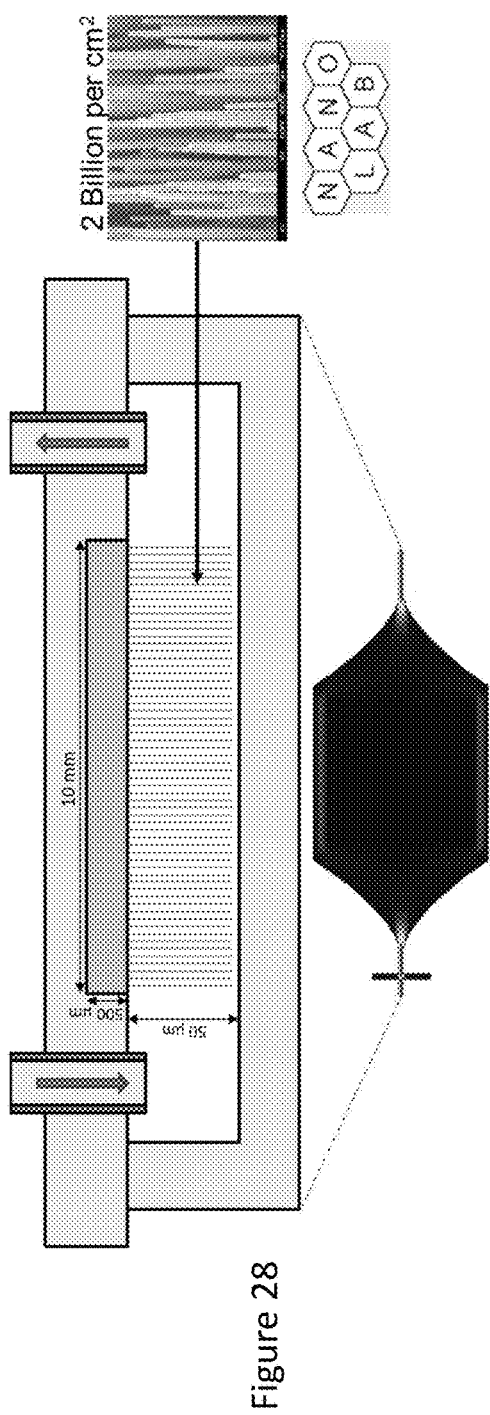
FIG. 28 is an illustration that depicts a CFPS system with a polymeric flow cell containing a silicon chip with micromachined micropillars or nanotubes.
Figure 29:
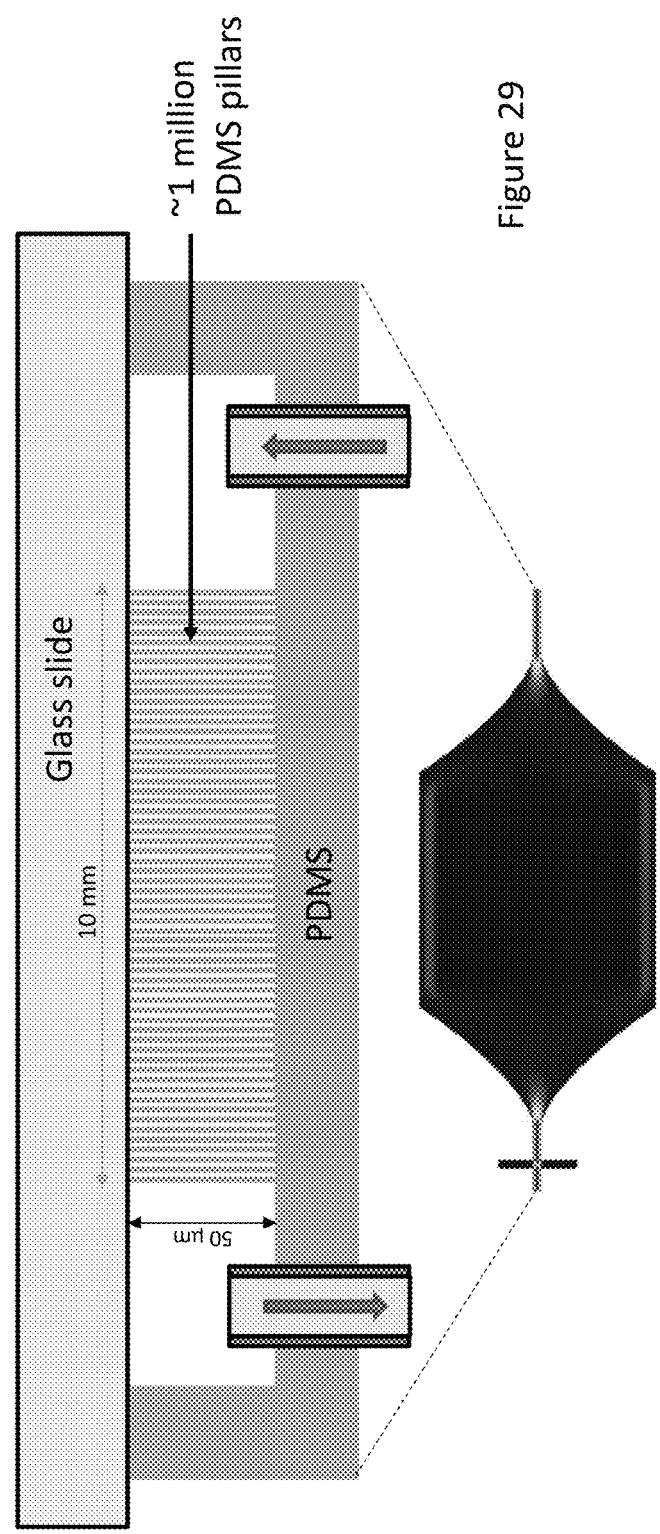
FIG. 29 is an illustration that depicts a CFPS system with PDMS micropillars integrated into the PDMS flow cell.

This example describes an exemplary method of manufacturing a CFPS system. In this example, the CFPS system comprises a chip comprising a plurality of micropillars to which ribosomes are attached via linkers A micromachining approach is used to create an array of micropillars on a silicon substrate. Briefly, silicon chips (1 cm$^2$) having an array of attached micropillars are manufactured by micromachining as essentially described in [K. Miller, M. Li, K. M. Walsh, and X.-A. Fu, Journal of Micromechanics and Microengineering, 23(3), 035039 (2013)]. The chips contain approximately 2×10$^6$ freestanding micropillars of about 50 µm height and the diameter of each micropillar is about 5 µm (~2 µm spacing). The micropillar chips are integrated into a polymeric flow cell that will be defined by microfabrication. This molding method allows for single-day turnaround if flow cell design improvements are needed [Duffy et al., Anal Chem 70(23): 4974-4984 (1998)]. Alternatively, micropillars and their encompassing flow cell may be fashioned out of polydimethylsiloxane (PDMS) or other polymer that is poured into a negative-image mold (created on a Si wafer with SU-8 2050 photoresist, Microchem Corp.), cured, peeled from the mold, then bonded to a glass slide using oxygen plasma bonding [J. Xiao, et al., RSC Advances, 5, 52161 (2015)]. FIG. 28 may be used to depict the CFPS system with a polymeric flow cell containing the silicon chip with micromachined micropillars (replacing the carbon nanotube forest array as noted in the figure). FIG. 29 illustrates a CFPS system with PDMS micropillars that are integrated into the PDMS flow cell.

Ribosomes were prepared for attachment by biotinylation as essentially described in Example 1.

Figure 30:
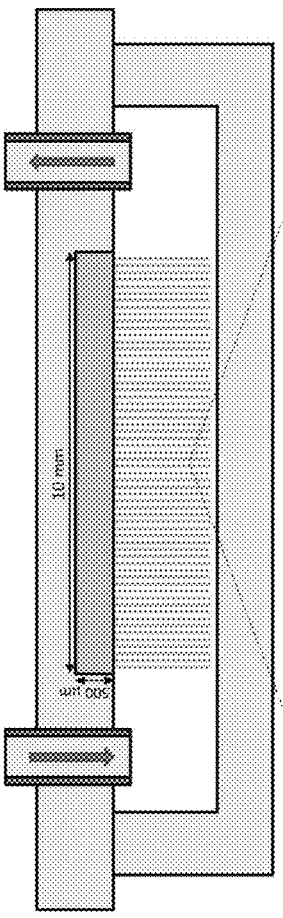
FIG. 30 is an illustration that depicts a CFPS system with CNTs and shows the attachment chemistry between ribosome and CNT.
Figure 31:
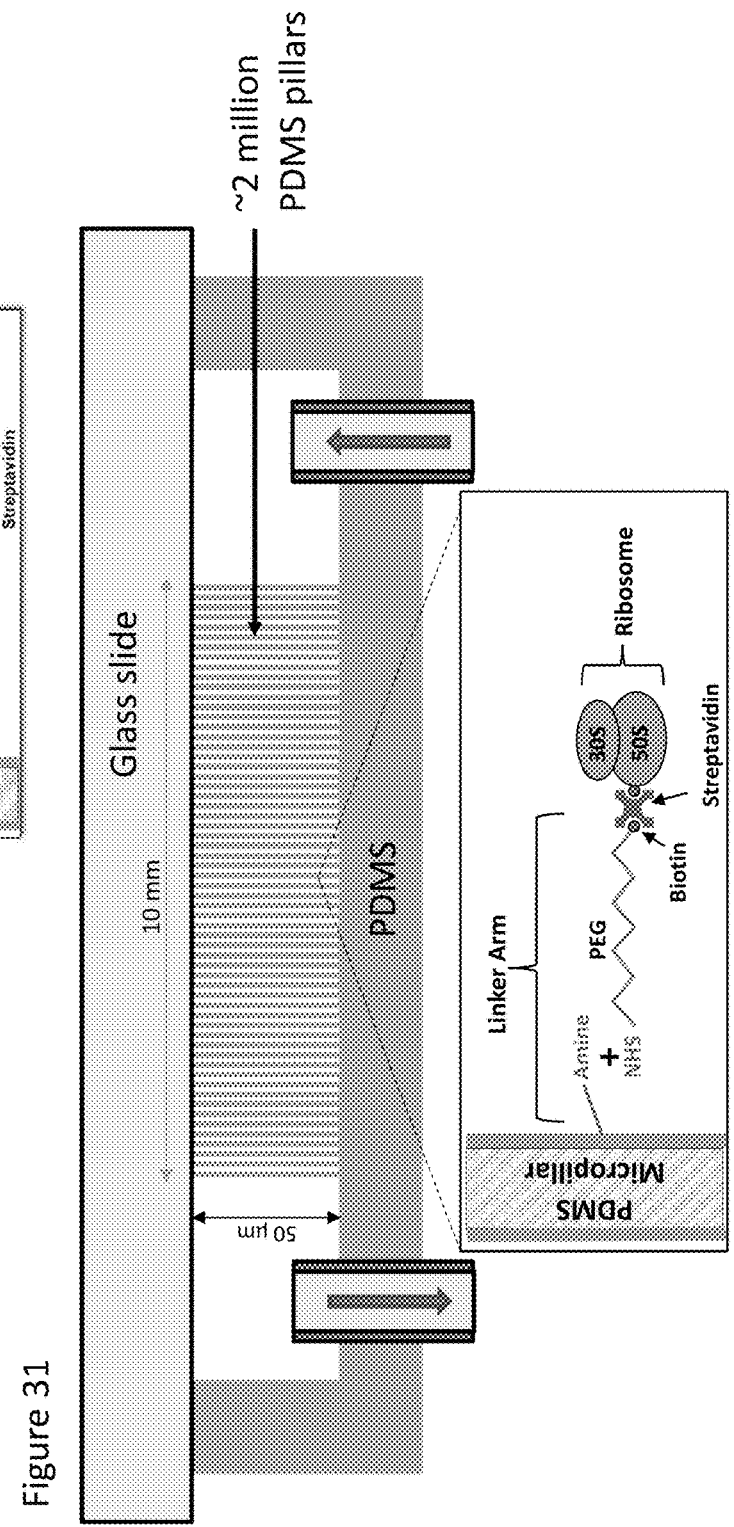
FIG. 31 is an illustration that depicts a CFPS system with PDMS micropillars and shows the attachment chemistry between ribosome and micropillar.

The micropillar array inside the flow cell is first coated with multiple polyelectrolyte layers that are subsequently modified to expose surface amine groups following the procedure described in [Yost et al., Microsystems Nanoeng 1:15037 (2015)]. Proper coating is verified through fluorescence microscopy of the fluorescently-labeled polyelectrolyte layers. Linker arms comprising a PEG chain terminating in NHS groups (which react with the surface amine groups of the modified CNT array) and biotin is then added to the CNT array (specifically NHS-PEG4-biotin, 29 Å length, ThermoFisher, 21330). Linker attachment is verified with fluorescently-labeled neutravidin (Oregon Green Neutravidin, ThermoFisher, A6374), which has a high affinity for biotin. Neutravidin is added to the array to attach to the biotinylated ends of the linker arms. The biotinylated ribosomes are flowed into the array to attach to each of the tethered neutravidins (each neutravidin reacts with four biotins, creating a bond between the linker arms and the ribosomes). Ribosome attachment verification is performed by fluorescently labeling the ribosomes using 5(6)-Carboxy-X-rhodamine (see [Stapulionis et al., Biol Chem 389(9): 1239-1429 (2008)]) and observing with fluorescent microscopy or a fluorescent scanner. In addition, SDS-PAGE gel analysis is used to verify the presence of the ribosomes after they are released from the arrays by denaturing the ribosomes (i.e., exposure to sodium dodecyl sulfate) or releasing one of the ribosomal subunits (50S or 30S) by decreasing magnesium levels in solution [Nierhaus, J Bateriol 196(22): 3817-3819 (2014)]. See FIG. 30 for silicon micropillars, replacing carbon nanotube ("CNT") with micropillar. See FIG. 31 for PDMS micropillars. The chemistry depicted in the biotinylation of the 50S subunit of the ribosome itself in these figures is highly truncated, as this process indeed contributes a spacer arm of nonzero length in the same way as the linkers that are attached to the micropillar forest.

The pETM6-mCherry plasmids (DNA templates that express the mCherry gene) were purchased from Addgene. Ample plasmid stock was created onsite via culturing *E. coli* and harvesting the plasmids with Qiagen Plasmid Maxiprep kits. The plasmid's quality was verified by inducing the *E. coli* line to express the mCherry protein [Marbach and Bettenbrock, J Biotechnol 157(1): 82-88 (2012)]. This protein product was analyzed with SDS-PAGE and/or fluorimetry. A dilution series of a mCherry standard (BioVision) was used to produce a concentration vs. fluorescence intensity curve. This was used to estimate mCherry production for on- and off-chip translation experiments. See FIG. 32 for an example with a silicon micropillar chip replacing a carbon nanotube forest chip.

The PURExpress kit (New England Biolabs) contained all the components to create proteins from a DNA template, and was used to verify that the mCherry plasmid expresses a functional protein that fluoresces within a cell-free system. Protein synthesis was quantified with fluorimetry and SDS-PAGE with Western blot analysis. The synthesis rate (0.14 amino acids per second, per ribosome) was calculated with the known protein product (8.6 µg), protein size (28.8 kDa, 256 amino acids), number of ribosomes per reaction (60 picomoles), and synthesis duration (2 hours).

The PURExpress mixture and mCherry template are continually infused into the flow cell with a Harvard Apparatus Pump 11 Elite syringe pump. A fluorescence microscope and heated stage is used to allow real-time observation of mCherry synthesis. The mCherry product is collected at the flow cell's outlet and quantified with fluorimetry and/or SDS-PAGE with Western blot analysis. The number of attached ribosomes can estimated by quantifying the 30S subunits with spectrophotometry after they are released from the tethered 50S subunits via decreasing Mg$^{2+}$ levels [Nierhaus, J Bacteriol 192(22): 3817-3819 (2014)]. The average synthesis rate of attached ribosomes is calculated and compared to the rate of free-floating ribosomes. If no fluorescence is observed (incomplete assembly/folding), then SDS-PAGE or LC-MS/MS is used to see how far along failure occurred during synthesis. The reusability of the CFPS system comprising the micropillar array is tested by washing away all reactants except the immobilized ribosomes with a compatible buffer, then repeating synthesis. The stability of the system is monitored by observing the total protein product for each iteration.

The table in FIG. 33 depicts that the CFPS micropillar system is estimated to produce protein at a rate of ~0.07 mg protein per hour for a chamber having a 5 µL reaction volume. Thus, the amount of protein made per unit time per volume chamber is estimated at 1.4×10$^{-2}$ mg/hr/µL, which is ~80% higher than the latest research [Timm et al., Small 6: 810-817 (2015)], which uses free-floating ribosomes in a microfluidic chip. An additional advantage of this technology over the latest research is that the localized ribosomes can be re-used for subsequent protein synthesis reactions.

Example 8

This example describes an exemplary method of manufacturing a CFPS system comprising a chip comprising a plurality of carbon nanotubes (CNTs) to which ribosomes are attached via linkers.

Figure 34:
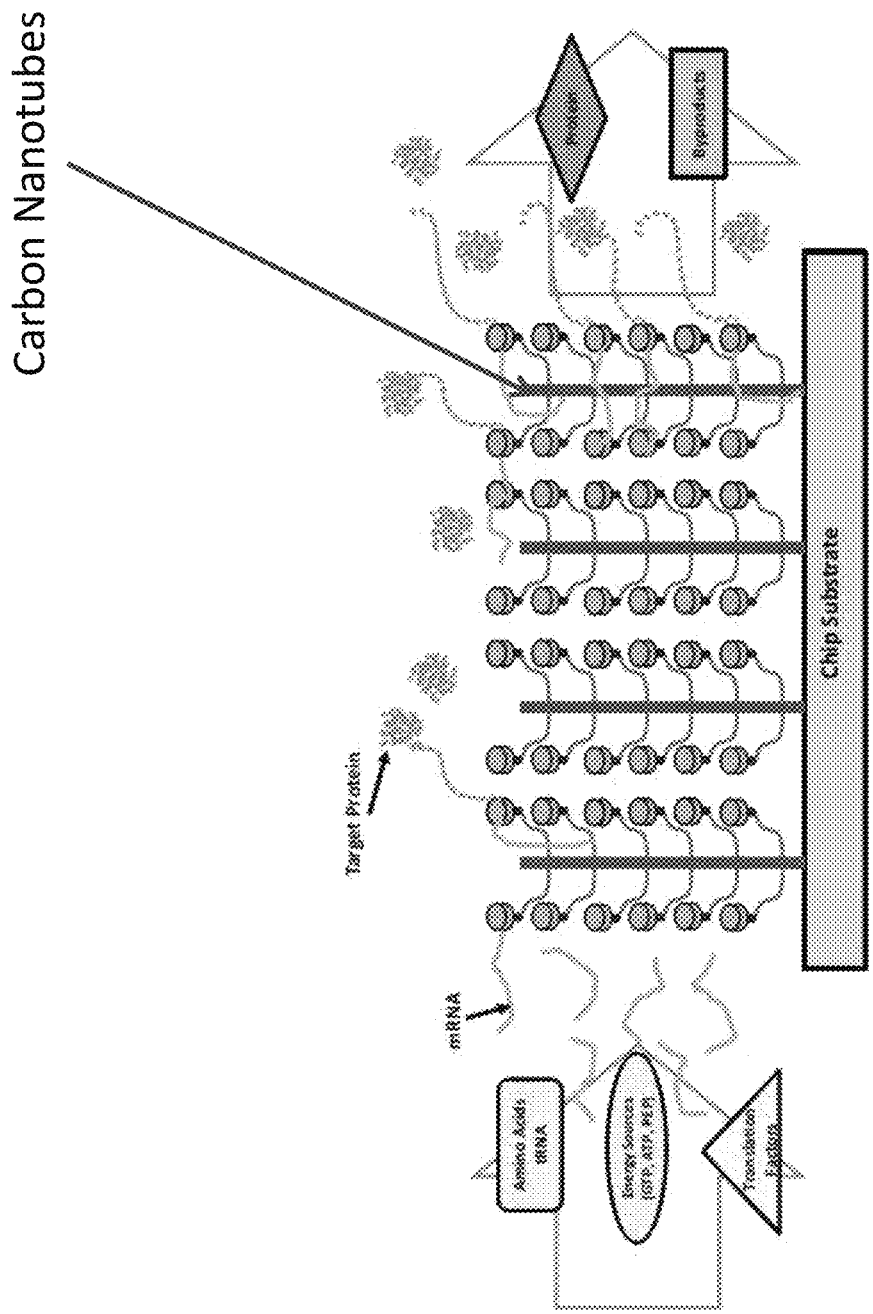
FIG. 34 is an illustration of a CFPS system comprising a microfluidic flow cell with an array of CNTs.

An illustration of the CFPS system comprising a microfluidic flow cell with an array of carbon nanotubes (CNTs) is shown in FIG. 34. In this CFPS system, a multiplicity of ribosomes is linked to the array. The CFPS system is characterized by a large surface-to-volume ratio of the CNTs which maximizes the surface area available for biomolecular interactions between the components of the IVT reactions, e.g., ribosomes, translation mixture, and mRNA. This system, like the CFPS system of Example 5, is designed to run as a continual process, such that reaction products (synthesized proteins) and inhibitory reaction byproducts are continually washed away for downstream processing and replaced by fresh consumables to repeat the manufacturing process with the same high-density array of ribosomes.

Figure 35:
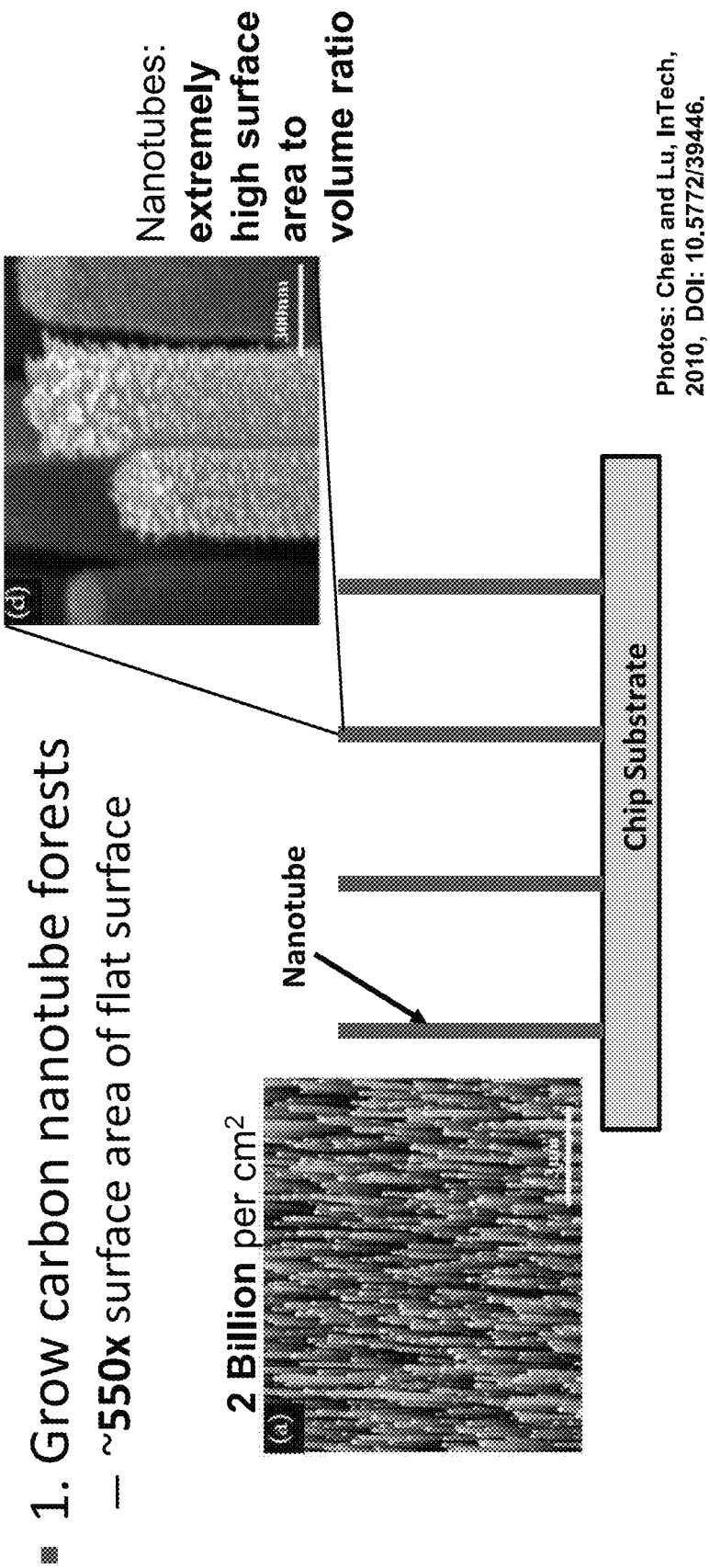
FIG. 35 is an illustration of a bottom-up creation of vertically-aligned carbon NT forests. Photos taken from Chen and Lu, InTech 2010, doi:10.5772/39446.

Compared to top-down fabrication approaches such as the photolithographic patterning and reactive ion etching of micropillars, the bottom-up creation of vertically-aligned carbon nanotube (VACNT) forests realize pillars with smaller diameter, spacing, and higher aspect ratio (height: diameter). See FIG. 35. For example, a 1 cm$^2$ chip containing 2×10$^9$ CNTs with 175 nm diameter and 50 µm length will provide ~30 times larger surface area and production rate for the same chip comprising 2×10$^6$ micropillars with 5 µm diameter and 50 µm length (FIG. 33). The table in FIG. 33 also shows, this CNT system has the potential to produce protein at over 90 times the rate per reaction chamber volume than the latest research described in [Timm et al., 2015, supra] and at a fraction of its footprint. Specifically, this CFPS system is estimated to produce protein at a rate of ~2.3 mg protein per hour for a 5 µL reaction chamber volume. The amount of protein made per unit time per volume chamber volume is estimated at 0.45 mg/hr/µL, which is over four orders of magnitude denser than the current industry standard practice of cell-based fermentation tanks.

The CFPS system were fabricated using photolithographic methods. Briefly, chips (1 cm$^2$) having an array of attached CNTs were manufactured by NanoLab, Inc. These chips contained approximately 1×10$^9$ freestanding CNTs of precisely-controlled length (~15 µm) and diameter (approximately 200 nm±40 nm). The chips comprising the CNT array were integrated into a polymeric flow cell that was defined by microfabrication. This molding method allows for single-day turnaround if flow cell design improvements are needed [Duffy et al., 1998, supra]. A top-down illustration of the chip (blue hexagonal shape at bottom) and an expanded view of the chip's cross-section (top) is shown in FIG. 28.

Ribosomes were prepared for attachment by biotinylation as essentially described in Example 1.

The CNT array inside the flow cell was first coated with multiple polyelectrolyte layers that were subsequently modified to expose surface amine groups following the procedure described in [Yost et al., 2015, supra]. Proper coating was verified through fluorescence microscopy of the fluorescently-labeled polyelectrolyte layers. Linker arms comprising a PEG chain terminating in NHS groups (which react with the surface amine groups of the modified CNT array) and biotin was then added to the CNT array (specifically NHS-PEG4-biotin, 29 Å length, ThermoFisher, 21330). Linker attachment was verified with fluorescently-labeled neutravidin (Oregon Green Neutravidin, ThermoFisher, A6374), which has a high affinity for biotin. Neutravidin was added to the array to attach to the biotinylated ends of the linker arms. The biotinylated ribosomes were flowed into the array to attach to each of the tethered neutravidins (each neutravidin reacts with four biotins, creating a bond between the linker arms and the ribosomes). Ribosome attachment verification is performed by fluorescently labeling the ribosomes using 5(6)-Carboxy-X-rhodamine (see [Sapulionis et al., Biol Chem 389(9): 1239-1249 (2008)]) and observing with fluorescent microscopy or a fluorescent scanner. In addition, SDS-PAGE gel analysis was used to verify the presence of the ribosomes after they were released from the arrays by denaturing the ribosomes (i.e., exposure to sodium dodecyl sulfate) or releasing one of the ribosomal subunits (50S or 30S) by decreasing magnesium levels in solution [Nierhaus, 2014, supra]. See FIG. 30. The chemistry depicted in the biotinylation of the 50S subunit of the ribosome itself in this figure is highly truncated, as this process indeed contributes a spacer arm of nonzero length in the same way as the linkers that are attached to the CNT forest.

The pETM6-mCherry plasmids (DNA templates that express the mCherry gene) were purchased from Addgene. Ample plasmid stock was created onsite via culturing *E. coli* and harvesting the plasmids with Qiagen Plasmid Maxiprep kits. The plasmid's quality was verified by inducing the *E. coli* line to express the mCherry protein [Marbach and Bettenbrock, J Biotechnol 157 (1): 82-88 (2012)]. This protein product was analyzed with SDS-PAGE and/or fluorimetry. A dilution series of a mCherry standard (BioVision) was used to produce a concentration vs. fluorescence intensity curve. This was used to estimate mCherry production for on- and off-chip translation experiments. See FIG. 32.

The PURExpress kit (New England Biolabs) contained all the components to create proteins from a DNA template, and was used to verify that the mCherry plasmid expresses a functional protein that fluoresces within a cell-free system. Protein synthesis was quantified with fluorimetry and SDS-PAGE with Western blot analysis. The synthesis rate (0.14 amino acids per second, per ribosome) was calculated with the known protein product (8.6 µg), protein size (28.8 kDa, 256 amino acids), number of ribosomes per reaction (60 picomoles), and synthesis duration (2 hours).

The PURExpress mixture and mCherry template are continually infused into the flow cell with a Harvard Apparatus Pump 11 Elite syringe pump. A fluorescence microscope and heated stage is used to allow real-time observation of mCherry synthesis. The mCherry product is collected at the flow cell's outlet and quantified with fluorimetry and/or SDS-PAGE with Western blot analysis. The number of attached ribosomes can estimated by quantifying the 30S subunits with spectrophotometry after they are released from the tethered 50S subunits via decreasing Mg$^{2+}$ levels [Nierhaus, 2014, supra]. The average synthesis rate of attached ribosomes is calculated and compared to the rate of free-floating ribosomes. If no fluorescence is observed (incomplete assembly/folding), then SDS-PAGE or LC-MS/MS is used to see how far along failure occurred during synthesis. The reusability of the CFPS system comprising the CNT array is tested by washing away all reactants except the immobilized ribosomes with a compatible buffer, then repeating synthesis. The stability of the system is monitored by observing the total protein product for each iteration.

Example 9

This example demonstrates in silico modeling of CFPS systems described herein.

In initial experiments, diffusion and advection of reactants into the CFPS system were simulated in silico using the COMSOL Multiphysics simulation package. Based on the simulation, the design of the flow cell that encapsulates the CNT array was modified to ensure that ribosomes (bioparticle in this study with lowest diffusion coefficient) are able to reach the center of the array [Yost et al., 2015, supra]. In the simulation, the CNT array is represented by a porous media with a certain porosity and permeability, while ribosomes were treated as simple particles with a diffusion constant and inlet concentration. Ribosome concentrations throughout the CNT array were monitored during a time-dependent study to understand the minimal duration needed to create an even concentration throughout the array during attachment procedures.

Figure 36:
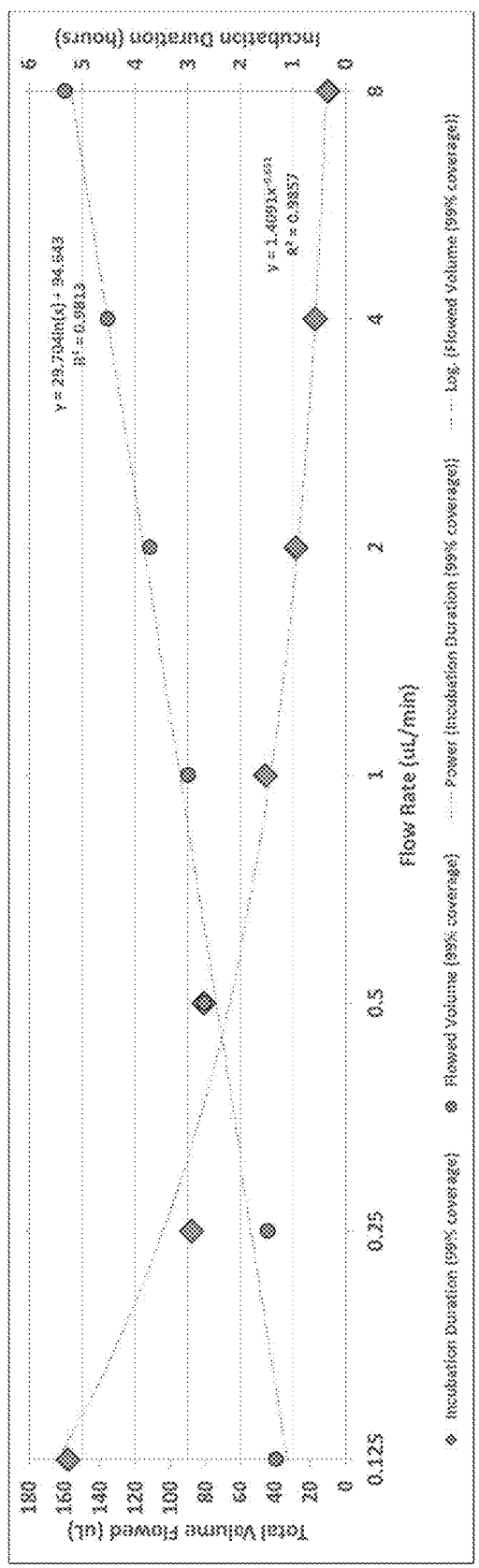
FIG. 36 is a graph of total volume flowed plotted as a function of flow rate and incubation duration.
Figure 37:
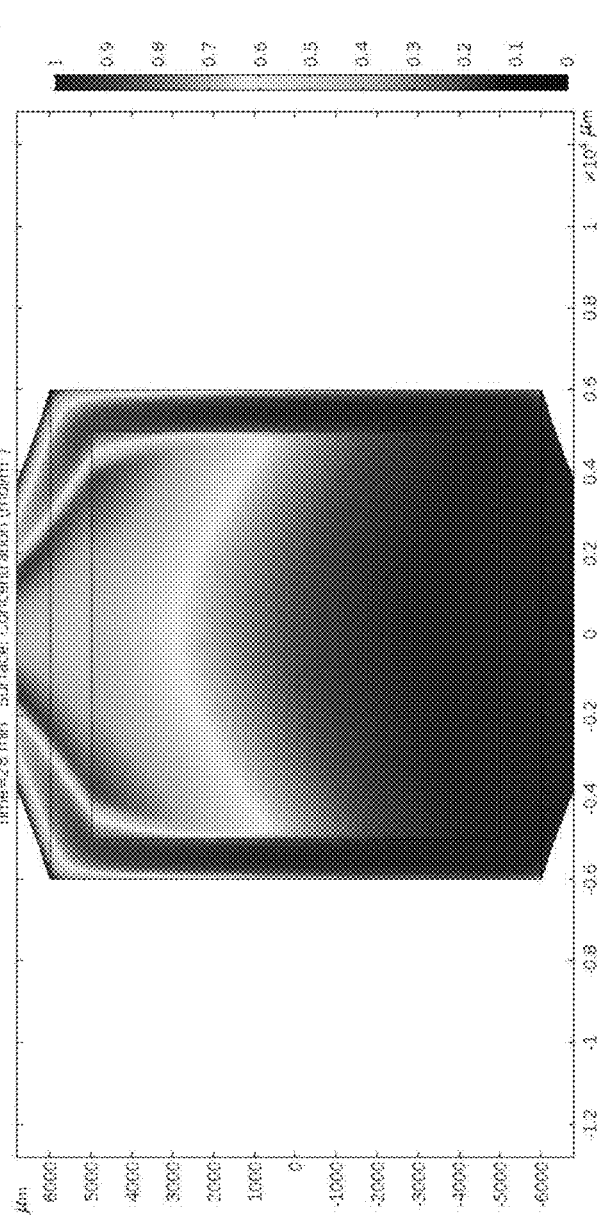
FIG. 37 is a graph that shows the concentration of ribosomes with the square VACNT chip after 28 minutes of infusion duration described in Example 9.

Simulations were run in a 150 µm tall flow cell that contained a 1 cm×1 cm array of vertically-aligned CNTs (VACNTs) with two 1 mm-wide lateral shunts between the edge of the array and the walls of the flow cell. The CNT parameters were as follows: 200 nm diameter, 200 nm spacing, 50 µm length, and in square unit cell configuration that gave $6.85 \times 10^8$ CNTs/cm$^2$. The 150 µm tall flow cell gave 100 µm space between the flow cell's ceiling and the top of the array to ensure enough ribosomes sample volume was available to diffuse into the array from above [Yost et al., 2015, supra]. These parameters were used to simulate the array as a porous medium within the flow cell with a porosity of 0.804 and permeability of $3.57 \times 10^{-15}$ m$^2$. The porosity was simply calculated by the ratio of the void space to the entire volume encompassed by the CNT array (1 cm×1 cm×50 µm). The permeability was estimated based on the porosity, CNT diameter, and tortuosity of the VACNT array, per [A. Tamayol and M. Bahrami, Physical Review E, 83, 046314 (2011)]. The molecular diffusion coefficient for a ribosome in aqueous buffer was estimated to be $1.43 \times 10^{-11}$ m$^2$/s, assuming it is represented as a sphere with radius of 15 nm. FIG. 36 illustrates the total volume and time needed to ensure the entire array was able to interact with the free-floating ribosomes for flow rates that varied from 0.125 to 8 µL/min. It was found that the ribosomes can be delivered throughout the entire array within reasonable amounts of sample volume (~90 µL) and duration (1.5 hr) with a 1 µL/min infusion duration. FIG. 37 shows the concentration of ribosomes within the square VACNT chip after 28 minutes of 1 µL/min infusion duration. The concentration was acquired by taking an X-Y cut plane at 1 µm above the flow cell's floor.

Example 10

This example describes an exemplary method of manufacturing a CFPS system comprising a carbon aerogel.

A carbon aerogel was produced via sol-gel polymerization of resorcinol and formaldehyde; acetic acid was used as a catalyst to create a micron-sized porous network [T. Baumann, et al., Journal of Non-Crystalline Solids, 354:3513-3515 (2008)]. Briefly, a 37% formaldehyde solution (17.9 g, 0.224 mol) and resorcinol (12.3 g, 0.112 mol) were dissolved in 15 mL water before adding glacial acetic acid (0.44 g, 0.007 mol). The mixture was then cast into glass molds and cured at 80° C. for 72 hours. Water was removed from the newly formed organic hydrogels by acetone wash, followed by drying with supercritical $CO_2$. The organic aerogels were then carbonized at 1050° C. for 3 hours under an $N_2$ atmosphere, creating aerogel monoliths with densities of ~0.55 g/cm$^3$. An activation step was performed under flowing $CO_2$ (10 sccm) at 950° C.

Figure 38:
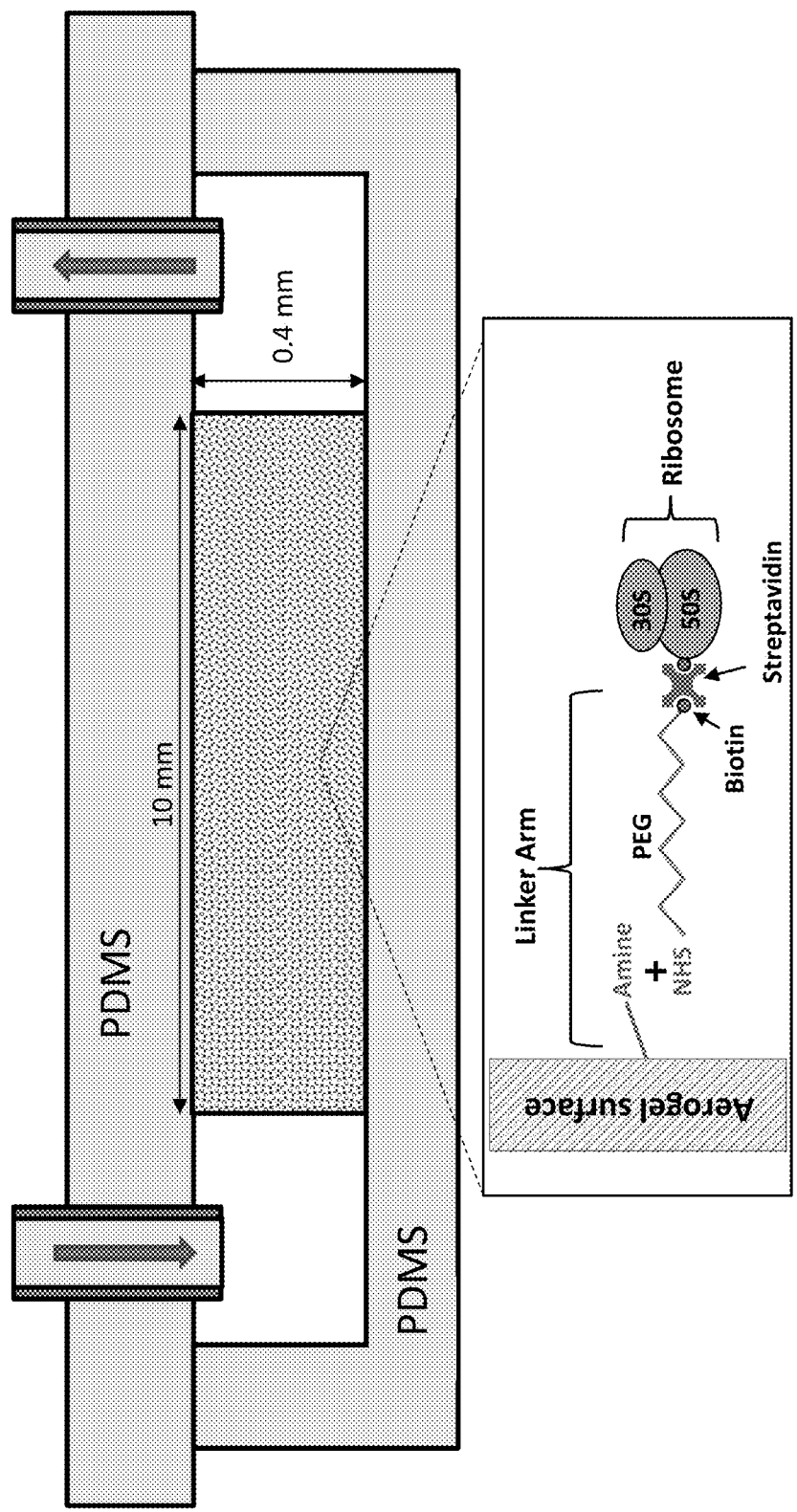
FIG. 38 is an illustration of a CFPS system comprising an aerogel and shows the attachment chemistry between the aerogel surface and ribosomes.
Figure 40:
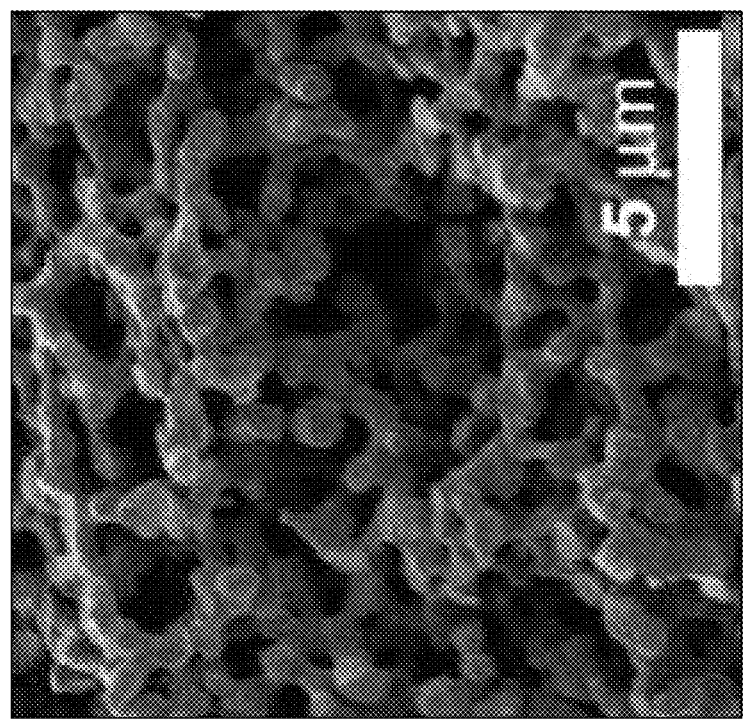
FIG. 40 is a scanning electron microscope image of an aerogel before assembly highlighting its surface area and porous network. Image provided by P. Campbell at Lawrence Livermore National Laboratory.
Figure 39:
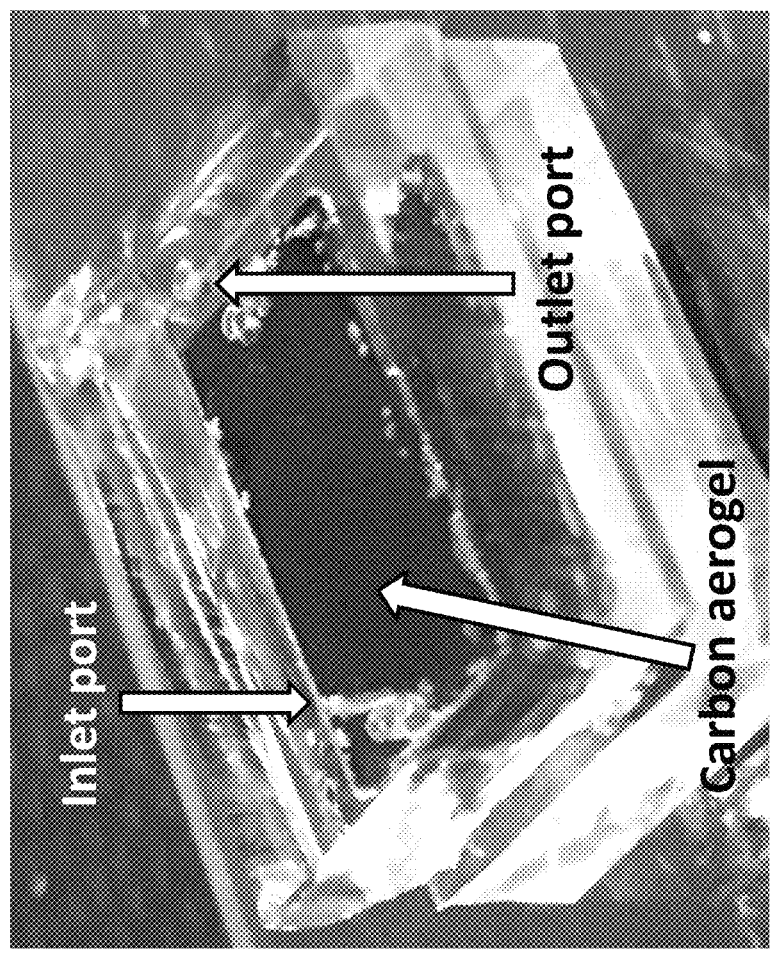
FIG. 39 is a photograph of a completely assembled CFPS system described in Example 10.

A 0.4 mm×5 mm×10 mm (height×width×length) piece of aerogel was cut via laser scribing and inserted into a polydimethylsiloxane (PDMS) flow cell with matching dimensions. Fluidic ports were cored out of the PDMS beforehand. FIG. 38 illustrates how the inlet port and outlet port are used to infuse and dispose, respectively, various fluids that will interact with the aerogel. FIG. 39 shows a completed assembly. FIG. 40 shows a scanning electron microscope (SEM) image of an aerogel before asseembly, highlighting its high surface area and porous network (photo courtesy of P. Campbell, Lawrence Livermore National Laboratory, Livermore, CA).

The aerogel inside the flow cell is first impregnated with primary amines as described in [L. Marques, Adsorption Science & Technology, 31, 223 (2013)]. Linker arms comprising a PEG chain terminating in NHS groups (which react with the surface amine groups of the modified CNT array) and biotin is then added to the CNT array (specifically NHS-PEG4-biotin, 29 Å length, ThermoFisher, 21330). Linker attachment is verified with fluorescently-labeled neutravidin (Oregon Green Neutravidin, ThermoFisher, A6374), which has a high affinity for biotin. Neutravidin is added to the array to attach to the biotinylated ends of the linker arms. The biotinylated ribosomes are flowed into the array to attach to each of the tethered neutravidins (each neutravidin reacts with four biotins, creating a bond between the linker arms and the ribosomes). Ribosome attachment verification is performed by fluorescently labeling the ribosomes using 5(6)-Carboxy-X-rhodamine (see [Stapulionis et al., Biol Chem 389 (9): 1239-1249 (2008)]) and observing with fluorescent microscopy or a fluorescent scanner. In addition, SDS-PAGE gel analysis is used to verify the presence of the ribosomes after they are released from the arrays by denaturing the ribosomes (i.e., exposure to sodium dodecyl sulfate) or releasing one of the ribosomal subunits (50S or 30S) by decreasing magnesium levels in solution [Nierhaus, J Bacteriol 196(22) 3817-3819, (2014)]. See FIG. 38. The chemistry depicted in the biotinylation of the 50S subunit of the ribosome itself in this figure is highly truncated, as this process indeed contributes a spacer arm of nonzero length in the same way as the linkers that are attached to the aerogel structure.

Figure 41:
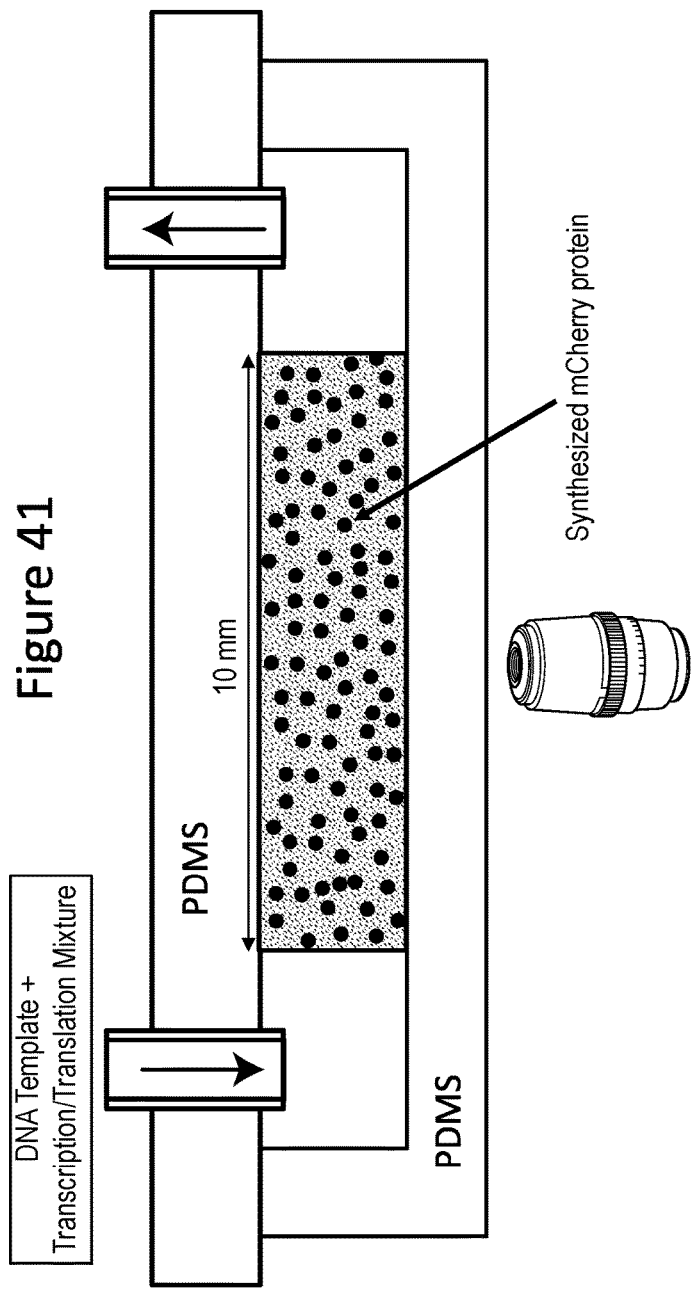
FIG. 41 is an illustration showing how mCherry DNA template and transcription and translation reagents are introduced into a CFPS system comprising an aerogel to produce mCherry fluorescent protein, which may be detected via microscopy.

The pETM6-mCherry plasmids (DNA templates that express the mCherry gene) were purchased from Addgene. Ample plasmid stock was created onsite via culturing E. coli and harvesting the plasmids with Qiagen Plasmid Maxiprep kits. The plasmid's quality was verified by inducing the E. coli line to express the mCherry protein [Marbach and Bettenbrock, 2012, supra]. This protein product was analyzed with SDS-PAGE and/or fluorimetry. A dilution series of a mCherry standard (BioVision) was used to produce a concentration vs. fluorescence intensity curve. This was used to estimate mCherry production for on- and off-chip translation experiments. See FIG. 41.

The PURExpress kit (New England Biolabs) contained all the components to create proteins from a DNA template, and was used to verify that the mCherry plasmid expresses a functional protein that fluoresces within a cell-free system. Protein synthesis was quantified with fluorimetry and SDS-PAGE with Western blot analysis. The synthesis rate (0.14 amino acids per second, per ribosome) was calculated with the known protein product (8.6 µg), protein size (28.8 kDa, 256 amino acids), number of ribosomes per reaction (60 picomoles), and synthesis duration (2 hours).

The PURExpress mixture and mCherry template are continually infused into the flow cell with a Harvard Apparatus Pump 11 Elite syringe pump. A fluorescence microscope and heated stage is used to allow real-time observation of mCherry synthesis. The mCherry product is collected at the flow cell's outlet and quantified with fluorimetry and/or SDS-PAGE with Western blot analysis. The number of attached ribosomes can estimated by quantifying the 30S subunits with spectrophotometry after they are released from the tethered 50S subunits via decreasing $Mg^{2+}$ levels [Nierhaus, 2014, supra]. The average synthesis rate of attached ribosomes is calculated and compared to the rate of free-floating ribosomes. If no fluorescence is observed (incomplete assembly/folding), then SDS-PAGE or LC-MS/MS is used to see how far along failure occurred during synthesis. The reusability of the CFPS system comprising the aerogel structure is tested by washing away all reactants except the immobilized ribosomes with a compatible buffer, then repeating synthesis. The stability of the system is monitored by observing the total protein product for each iteration.

As the table in FIG. 33 shows, this CFPS system is estimated to produce protein at a rate of ~50 mg protein per hour and for a chamber having a 20 µL reaction volume. Thus, the amount of protein made per unit time per volume chamber is estimated at 2.5 mg/hr/µL with a footprint of 0.5 cm². This production rate per volume is the highest of all methods listed in the table in FIG. 33, generating ~6 times more protein per µL than the CNT method. This is assuming macropore aerogel surface area (large enough to be useful for ribosome attachment purposes) is approximately 110 m² per g, or 61.6 m² per mL [Kovalenko et al., J. Porous Mater., 25:1017-1026 (2018)].

Example 11

This example describes an exemplary method of manufacturing a CFPS system comprising a bead comprising a plurality of carbon nanotubes (CNTs) to which ribosomes are attached via linkers.

Figure 42:
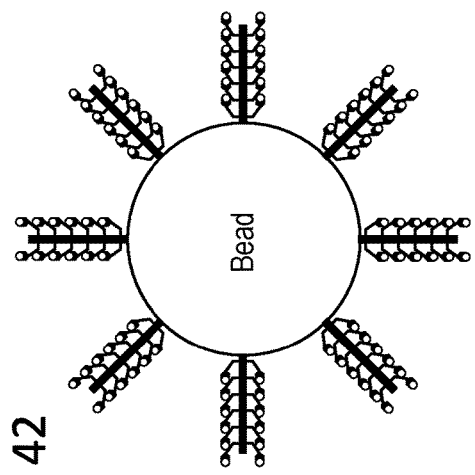
FIG. 42 is a CFPS system comprising CNTs attached to a bead as described in Example 11.

CNTs are attached to beads as depicted in FIG. 42.

Single-walled CNTs (SWCNTs) are attached to amine-coated beads (ThermoFisher, 20266) by the following process. Carboxylated SWCNTs (Sigma-Aldrich, 652490) are modified to have NHS functionality using the same methods as in [S. Madani, et al., *International Journal of Nanomedicine*, 7, 905 (2012)]. Succinctly, 1.2 mg of the carboxylated SWCNTs are suspended in 1 mL phosphate buffered saline (PBS), pH 7.4, containing 6 mg of EDC (Sigma-Aldrich, 03449) and 6 mg of NHS (Sigma-Aldrich, 130672). The mixture is placed on a rocker at room temperature for 30 minutes, followed by removing the excess reactants with a 10 kDa centrifugal column (Sigma-Aldrich, Z677108). The NHS-functional SWCNTs are resuspended in 1 mL PBS, pH 7.4. Five hundred µL of amine-coated beads (dry bed volume) are then added to the SWCNT solution and rocked for 3 hours at room temperature. Excess SWCNTs are removed by repeatedly centrifuging the beads and resuspending them in fresh PBS three times.

Thirty µL of the CNT beads are coated with multiple polyelectrolyte layers to expose surface amine groups as essentially described in Example 7. Linker attachment to the CNTs via the exposed amines and ribosome attachment are carried out as essentially described in Example 7. Verification of each attachment is performed as described above in Example 7.

The CNT beads with attached ribosomes are either packed into a column as described in Example 1 or into a microfabricated chip as described in Example 6. For each system, the PURExpress mixture and mCherry template are continually infused into the flow cell with a syringe pump and IVT reactions are carried out as essentially described in Examples 1 and 7. Protein levels are measured and quantified as described in Example 1.

Example 12

This example demonstrates the reusability of the presently disclosed CFPS system.

In separate studies, batch synthesis of proteins was carried out in a centrifuge tube as essentially described in Example 1, but in these studies, the streptavidin-coated polystyrene beads were about 1 micron in diameter.

Figure 43:
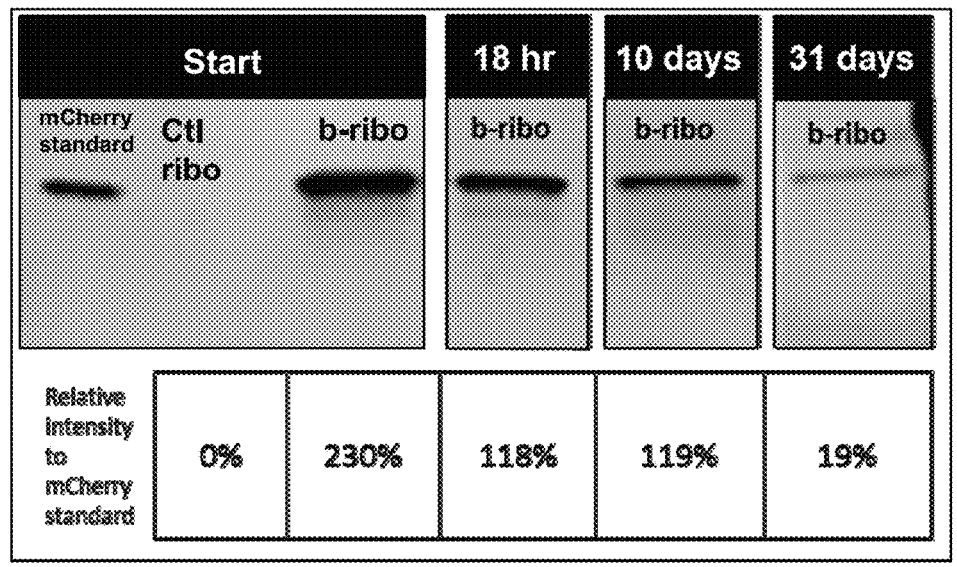
FIG. 43 is a combined image of Western blots from four CFPS reactions performed at different time point (at to and at 18 hr, 10 days and 31 days after $t_0$) using the same set of bead-bound ribosomes and a table listing the relative total intensities of the bands. These data show the reusability of the CFPS system in synthesizing the mCherry protein. Labels: "Ctl ribo" are a CFPS system that contains streptavidin beads that have been incubated with ribosomes that have no biotin linker; "b-ribo" is a CFPS system that contains streptavidin beads that have been incubated with ribosomes that have a biotin linker. The mCherry standard is used to verify that indeed mCherry was created by the bead-based system. The relative total intensity of each band is compared to its respective standard (only the standard for the first reaction is shown).

In a first study, the streptavidin-coated polystyrene beads were used to make mCherry protein multiple times over a one-month period. IVT reactions were used with the beads at $t_0$ and then IVT reactions were carried out 18 hours, 10 days and 31 days after $t_0$. The beads were washed with ribosome washing buffer (described in Example 1) after each IVT reaction time point and then stored at 4° C. until the next IVT reaction was carried out. At each time point, samples of the mCherry protein produced were collected, separated by SDS-PAGE and then transferred onto a membrane for Western blotting using an anti-mCherry antibody. FIG. 43 is an image of the Western blots of the mCherry samples made using beads for the first time (at $t=t_0$) or at 18 hours, 10 days or 31 days after to. FIG. 43 also provides the relative densities of the Western blot bands for mCherry (densities of bands relative to the control band present on each SDS-PAGE gel). This figure shows that the CFPS system makes detectable amounts of protein even after multiple uses of the beads and even 31 days after the first use. In addition, these data support the requirement for biotinylated ribosomes ("b-ribo") used with the streptavidin beads, as beads incubated with ribosomes without biotin linkers ("Ctl ribo") did not produce any detectable amounts of mCherry.

Figure 44:
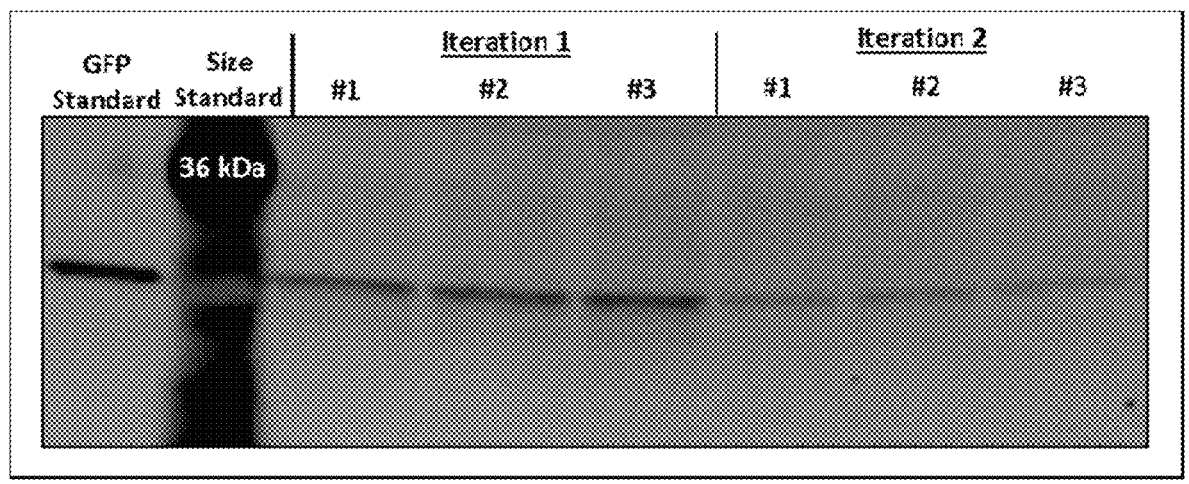
FIG. 44 is an image of a Western blot of synthesized GFP protein using the same set of bead-bound ribosomes in two different iterations (Iteration 1 and Iteration 2). The experiment was carried out in triplicate (and labeled #1, #2, and #3). These data show the reusability of CFPS system in synthesizing protein. The GFP standard is used to verify that indeed GFP was created by the bead-based system.

In a second study, the CFPS system described in the first study of this example was used with plasmids comprising a sequence encoding GFP instead of mCherry. In this study, IVT reactions using the beads and GFP plasmids were carried out in two rounds to synthesize two batches of GFP protein. Each time the same beads were used. Washes were performed between each round and the beads were stored at 4° C. between each round. The experiments were carried out in triplicate and therefore centrifuge tubes comprising the beads, plasmids and reagents were numbered 1-3. FIG. 44 is a Western blot of GFP samples produced within each tube (#1, #2, #3) from each of the two iterations (Iteration 1 and Iteration 2) using bead-bound ribosomes. A GFP standard was used as a reference. As shown in FIG. 44, the bead-based CFPS system was able to be reused to create detectable amounts of GFP. This data supports the reusability of the CFPS system.

Figure 45:
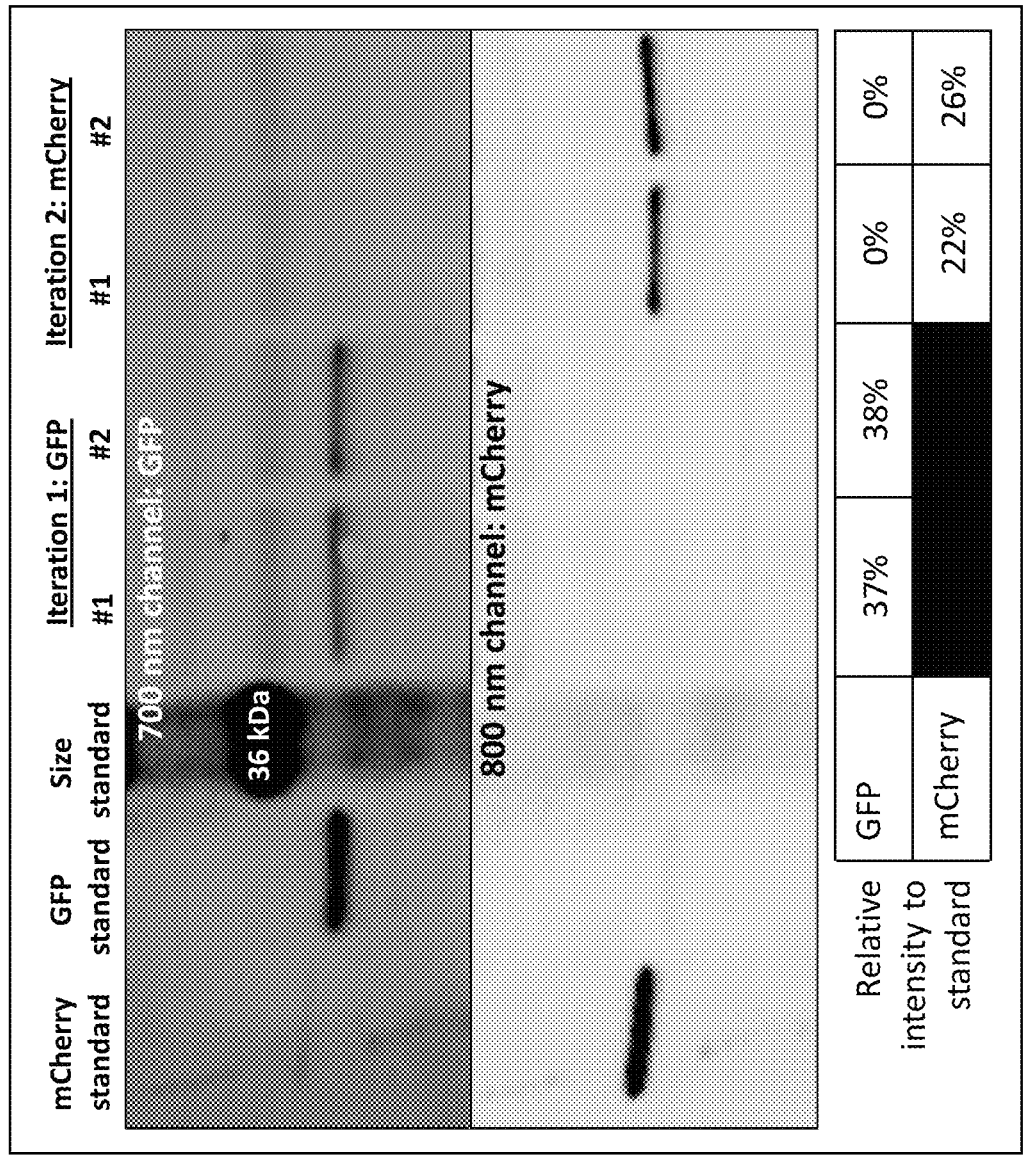
FIG. 45 is a combination of images of Western blots of synthesized proteins made in two subsequent IVT reactions using the same set of bead-bound ribosomes. The experiment was carried out in duplicate (and labeled #1 and #2). The top panel shows the GFP protein synthesized in Iteration 1. This panel also shows the lack of mCherry protein synthesized. The middle panel shows the mCherry protein synthesized in Iteration 2 and the absence of detectable GFP protein. The table at the bottom lists the relative total intensities of the bands. These results show the programmability of the CFPS system. Western analysis is of the same gel, but under two optical interrogation channels: 700 nm for GFP and 800 nm for mCherry. The mCherry and GFP standards were used to verify that indeed mCherry and GFP were created by the bead-based system. The total intensity of each band is compared to its respective standard.

In a third study, the CFPS system described in the first study of this example was used to produce two different proteins, GFP and mCherry, in two separate but sequential iterations with the same set of ribosome-coated beads. In the 1st iteration, GFP plasmids were used to produce GFP and in the $2^{nd}$ interation, which occurred ~5 hours after the 1st iteration, mCherry plasmids were used to produce mCherry protein. The beads were washed with ribosome washing buffer (as described in Example 1) between the 1st and $2^{nd}$ iterations. The results of this study are shown in FIG. 45. The Western blot analysis of FIG. 45 shows the same CFPS system may not only be used more than once to produce proteins, but also that the same set of beads can be used to produce different proteins. Importantly, the absence of GFP bands for the $2^{nd}$ iteration (mCherry synthesis) shows that no contamination or carry-over was observed from the $1^{st}$ iteration. This demonstrates the potential for this system to be highly modular that can synthesize various proteins on demand without the need to replace the beads or vessel containing the beads.

Example 13

This example demonstrates the functional activity of the proteins produced by the CFPS systems of the present disclosure.

Figure 46:
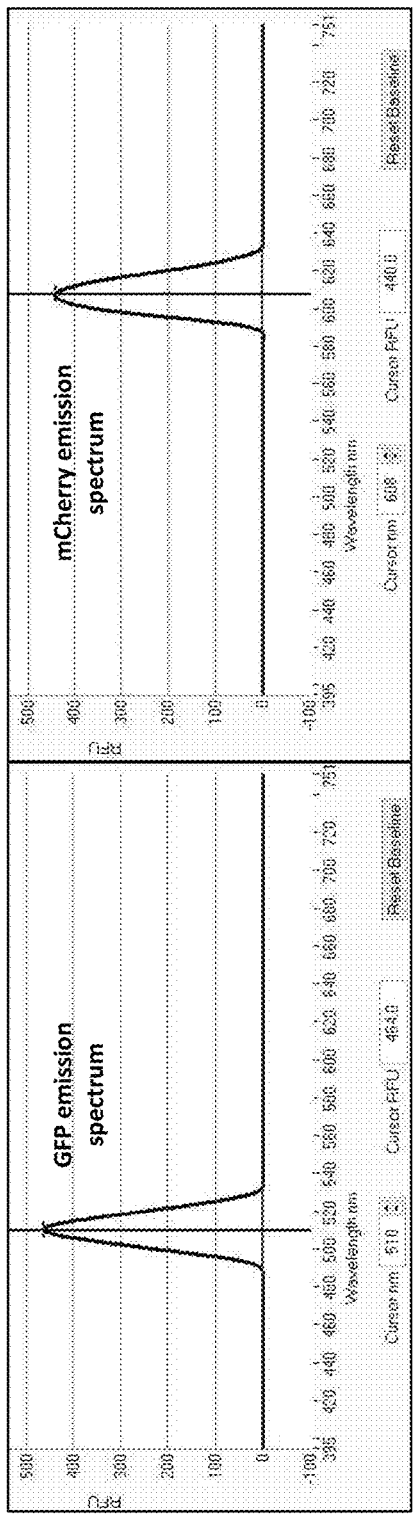
FIG. 46 is a pair of graphs of the relative fluorescence units (RFU) response of the GFP and mCherry proteins, both created in separate bead-based CFPS reactions. A Nanodrop 3300 fluorometer with white light excitation was used. Both responses were centered around the expected maxima for each fluorescent protein.

The CFPS system described in Example 12 was used to produce mCherry or GFP. The functionality of the produced proteins was demonstrated by measuring the fluorescence activity as evaluated using a Nanodrop 3300 (ThermoFisher). The results of the assay are shown in FIG. 46. This figure shows the fluorescence emission spectra of each protein (under white light excitation) are both centered around their expected peaks (510 nm for GFP and 608 nm for mCherry).

Taken together, the data of Examples 12 and 13 demonstrate the reusability, (re-) programmability, storage life, and ability to make functional proteins of the presently disclosed CFPS systems. The overall practicality of the CFPS systems of the present disclosure are thus demonstrated.

Example 14

Figure 47:
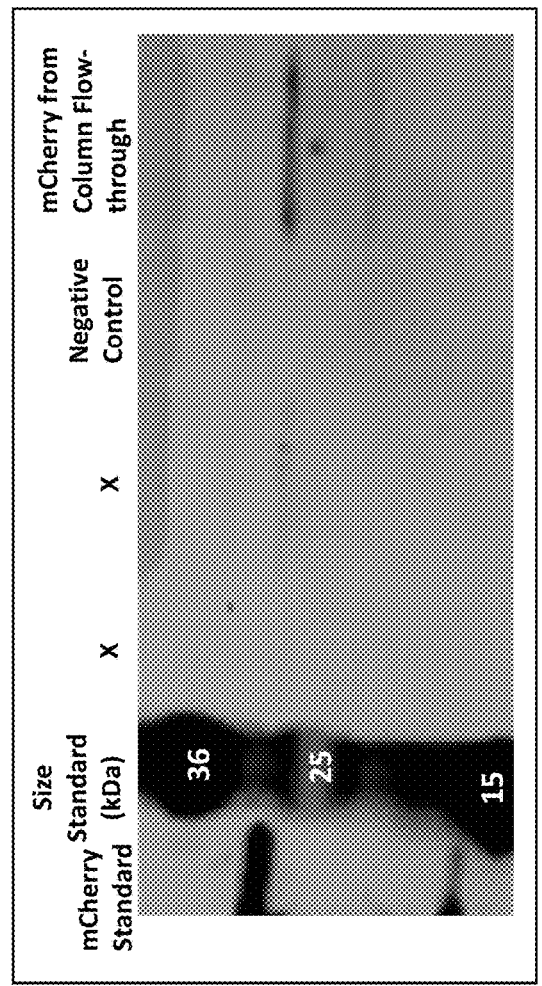
FIG. 47 is an image of a Western blot of flow-based synthesis of the mCherry protein. mCherry was detected in the column flow-through (far right), and compared to the mCherry standard, size standard, and a negative control (CFPS with all constituents except beads and ribosomes). Lanes marked with 'X' are not pertinent to this investigation.

This example supports a flow-based protein synthesis in a pressurized, bead-packed column.

mCherry was synthesized by flowing CFPS reagents (reagents similar to those described in Example 1) through a packed bed of 1 micron diameter streptavidin beads coated with biotinylated ribosomes. Polymer tubing with internal diameter of 0.75 mm was packed with the beads via syringe pump. A 0.5 micron frit at the end of the tubing ensured beads were retained in the column. The bead syringe was replaced with a second syringe that contained all necessary CFPS reagents, including mCherry plasmid, and infused at 0.2 µL per min for overnight duration. Tape heaters were used to ensure 30° C. column temperature. FIG. 47 shows Western analysis of the column flow through, showing proof of concept of flow-based synthesis of a protein in a bead-packed column.

Example 15

Figure 48:
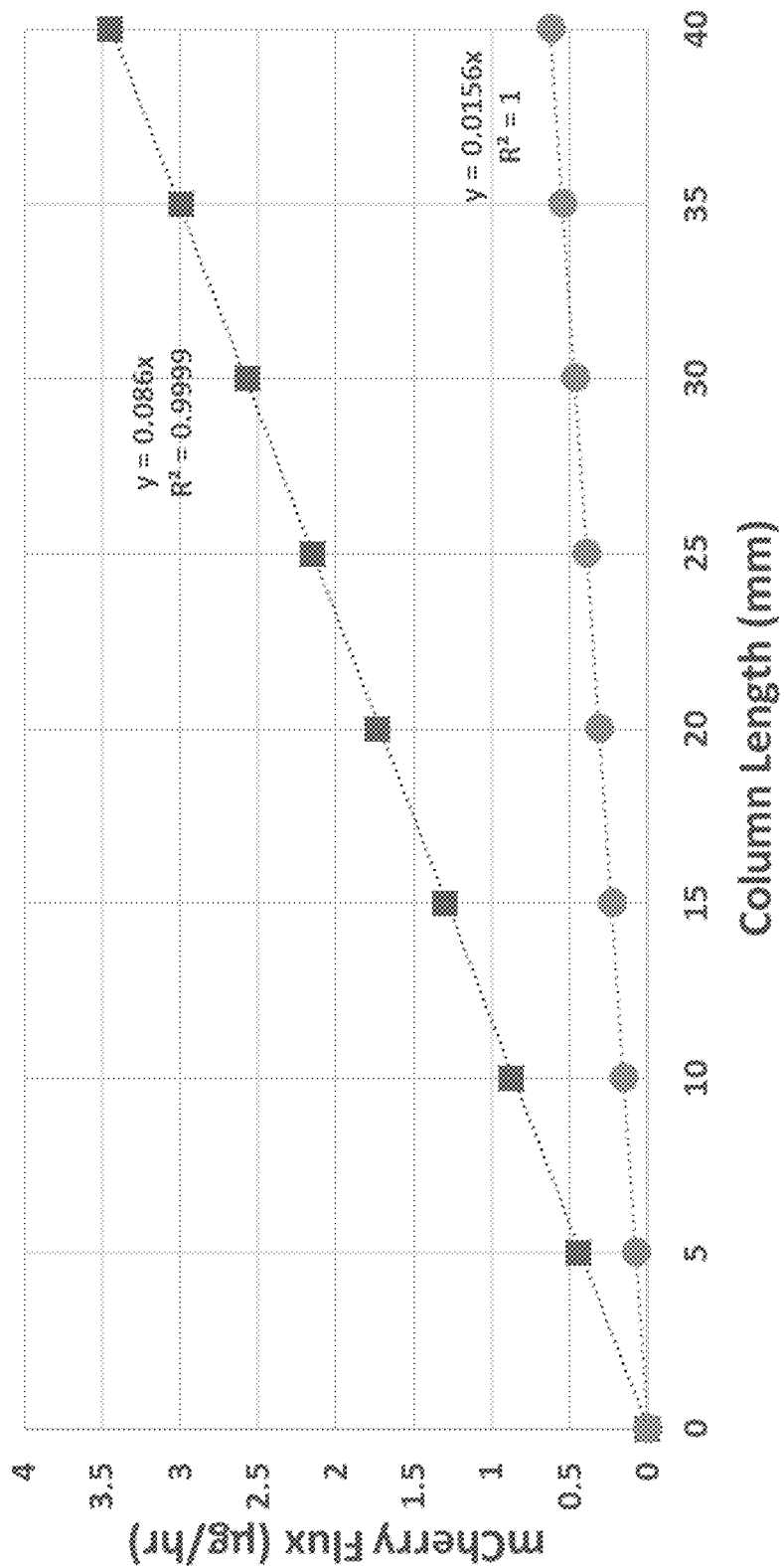
FIG. 48 is a graph of mCherry protein flux plotted as a function of the length of a pressurized column packed with ribosome-coated microbeads as determined via finite element analysis. Protein flux is shown along the length of the column, and is compared to the flux of a commercial batch reaction. The batch flux is based on the average production rate for a four-hour reaction of 25 μL volume, which is then scaled down proportionally to the interstitial volume at a particular column length.

Finite element analysis via COMSOL Multiphysics 5.4a was used to estimate the advantages of the flow-based, packed bed CFPS technology in Example 14 over standard batch CFPS technology. A 40 mm long, 750-micron diameter column geometry defined as a homogenous, porous medium to simulate a packed bed of 1 micron beads (face centered cubic packing was assumed). The porosity of the porous medium was defined by the ratio of the interstitial volume to the total column volume. The reaction rate per unit volume of the bed was determined by multiplying the average number of ribosomes per unit volume of packed beads (found experimentally) by the average rate of amino acids assembled by each ribosome during mCherry protein synthesis (found experimentally with New England Biolabs CFPS kit with free-floating ribosomes; see Example 1). Successful synthesis for a particular volume within the column depended on the presence of minimum concentration of mCherry mRNA molecules, which were infused at a velocity of ~17 micrometers per s. FIG. 48 compares the symthesized mCherry flux (µg per hour) of the pressurized packed column to that of a standard New England Biolabs batch reaction with free-floating ribosomes along different lengths of the column. The batch flux was calculated by scaling the flux of a full 25 µL reaction (3.4 µg per hour) down proportionally to the interstitial volume of the packed bed at a particular length (e.g., column interstitial volume at 20 mm length is 2.3 µL; batch will result in 0.31 µg per hour). The results show that the pressurized column method may provide over five times the mCherry flux than a standard batch reaction of the same volume. Protein fluxes of mg or even g per hour can be achieved by increasing the diameter of the column while keeping mRNA concentration and flow velocity through the column the same, creating a practical tool that can be used for portable point-of-contact medicine to rapid synthesis of drug candidates for patient trials for pharmaceutical companies.

Example 16

This example supports a flow-based synthesis using a slurry of ribosome-coated beads in a closed fluidic system.

Figure 49:
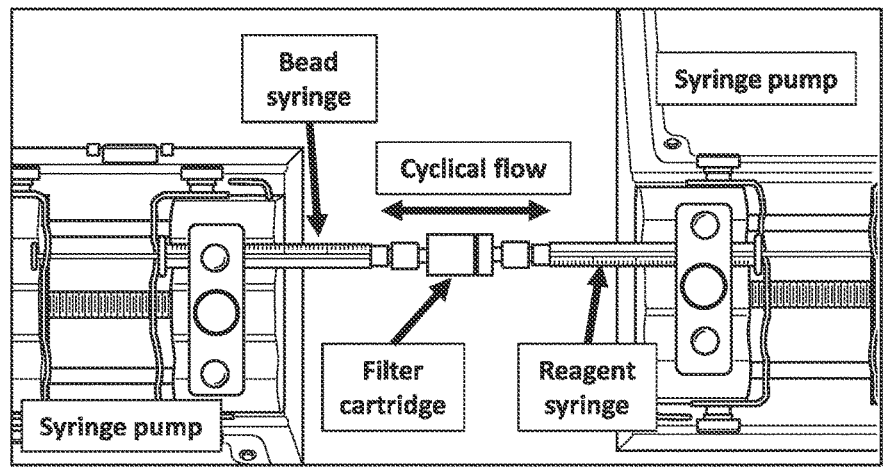
FIG. 49 is a top-view photograph of a flow-based protein synthesizer that uses ribosome-coated beads, CFPS synthesis reagent, syringes, syringe pumps, and a cartridge filter (heater tape not shown). Both syringe pumps are synchronized to infuse/withdraw to ensure flow direction is the same for both pumps. The CFPS reagent is constantly recirculated through the beads to get maximum protein yield.

A 20% (volume beads/total volume) slurry of ribosome-coated beads (as described in Example 12) is created by mixing them with all necessary CFPS ingredients (50 µL total volume) to synthesize mCherry. This slurry was then loaded into a 100 µL syringe ('bead syringe') that is then fluidically connected to a second 100 µL syringe ('reagent syringe') via a 0.5 µm frit cartridge. The second syringe contains 50 µL of all the necessary CFPS ingredients (minus ribosomes) to synthesize mCherry. Each syringe is placed into its respective syringe pump, and syringes are repeatedly infused/withdrawn at the same flow rate of 0.2 µL per min to create movement of beads within the first syringe and feed fresh CFPS ingredients from the second syringe. The filter frit ensures the beads will stay in the bead syringe, but allow new reagents to be recirculated through the bead syringe via various synchronized flow functions for both syringes (e.g., pulsed, constant flow, ramped flow, etc.). FIG. 49 illustrates this configuration with syringe pumps, syringes, and filter cartridge. Heating tape is used to ensure the syringes and frit are maintained at 37° C. during the synthesis procedure. At the end of synthesis, the bead syringe is infused and he reagent syringe is withdrawn simultaneously to harvest the mCherry product. The reagent syringe is emptied of the synthesized protein and then refreshed with new reagent to continue synthesis.

Figure 50:
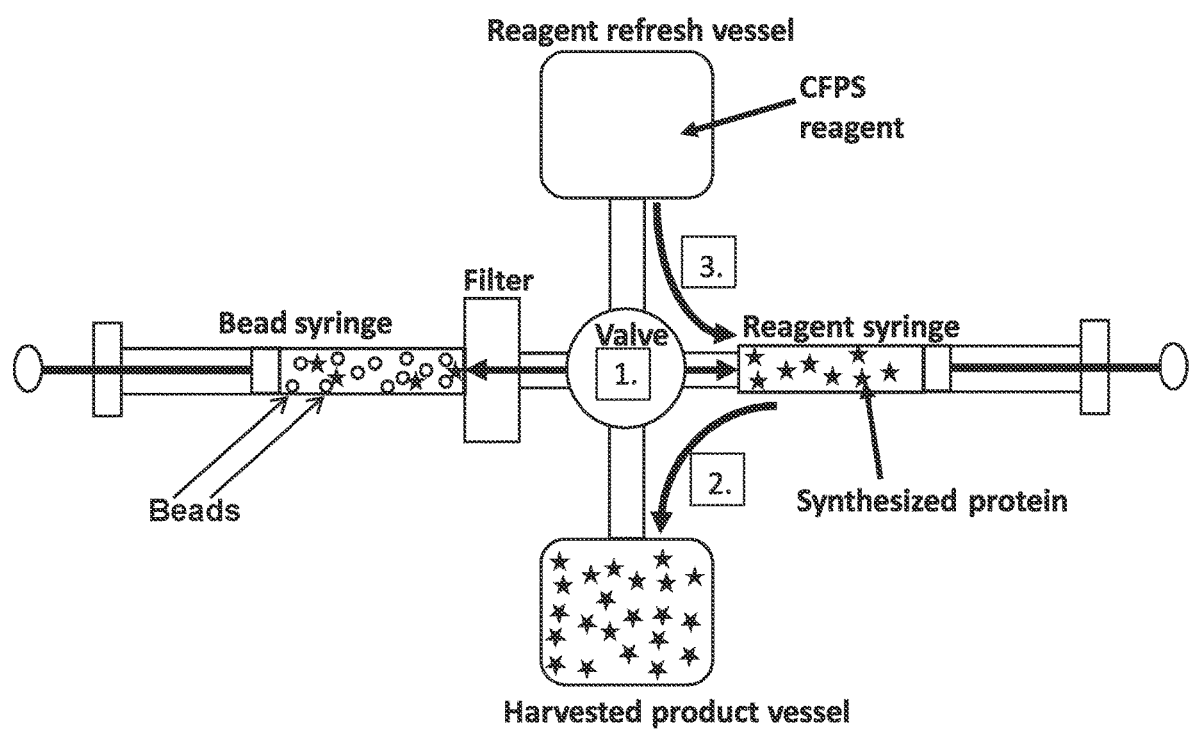
FIG. 50 is a diagram depicting an automated, flow-based protein synthesizer that uses ribosome-coated beads, CFPS synthesis reagent, syringes, syringe pumps (not shown), heater tape (not shown), and cartridge filter. Step 1: CFPS reagent is recirculated through the beads. Step 2: protein product is infused into and stored within a harvested product vessel. Step 3: fresh reagent is withdrawn into the reagent syringe before starting Step 1 again.

This basic setup is automated with additional valves, fluidic connections, actuators, electronics, and/or computer programs to automatically harvest the protein product after synthesis and refresh with new CFPS reagents. FIG. 50 illustrates this concept.

REFERENCES

The following references are cited throughout the above disclosure adhering to the following numbering scheme:

[1] A. S. Spirin, V. I. Baranov, L. A. Ryabova, S. Y. Ovodov, and Y. B. Alakhov, "A Continuous Cell-Free Translation System Capable of Producing Polypeptides in High Yield," *Synthesis (Stuttg).*, vol. 242, no. 4882, pp. 1162-1164, 1988.

[2] P. Siuti, S. T. Retterer, and M. J. Doktycz, "Continuous protein production in nanoporous, picolitre volume containers," *Lab Chip*, vol. 11, no. 20, pp. 3523-3529, 2011.

[3] P. W. K. Rothemund, A. Ekani-Nkodo, N. Papadakis, A. Kumar, D. K. Fygenson, and E. Winfree, "Design and characterization of programmable DNA nanotubes," *J. Am. Chem. Soc.*, vol. 126, no. 50, pp. 16344-16352, 2004.

[4] J. D. Puglisi, S. C. Blanchard, and R. L. Gonzalez, "Surface Based Translation System," U.S. Pat. No. 7,297, 532 B2, Nov. 20, 2007.

[5] P. Siuti, S. T. Retterer, C. K. Choi, and M. J. Doktycz, "Enzyme reactions in nanoporous, picoliter volume containers," *Anal. Chem.*, vol. 84, no. 2, pp. 1092-1097, 2012.

[6] A. C. Timm, P. G. Shankles, C. M. Foster, M. J. Doktycz, and S. T. Retterer, "Toward Microfluidic Reactors for Cell-Free Protein Synthesis at the Point-of-Care," *Small*, no. 6, p. n/a-n/a, 2015.

[7] F. Vanzi, S. Vladimirov, C. R. Knudsen, Y. E. Goldman, and B. S. Cooperman, "Protein synthesis by single ribosomes," *Rna*, vol. 9, no. 10, pp. 1174-1179, 2003.

[8] P. P. Dennis and H. Bremer, "Modulation of Chemical Composition and Other Parameters of the Cell by Growth Rate," in *Escherichia coli* and *Salmonella: Cellular and Molecular Biology*, 2nd ed., F. Neidhardt, Ed. Washington D.C.: ASM Press, 1996, pp. 1553-1569.

[9] A. Katranidis, D. Atta, R. Schlesinger, K. H. Nierhaus, T. Choli-Papadopoulou, I. Gregor, M. Gerrits, G. Büldt, and J. Fitter, "Fast biosynthesis of GFP molecules: A single-molecule fluorescence study," *Angew. Chemie-Int Ed.*, vol. 48, no. 10, pp. 1758-1761, 2009.

[10] C. D. Blanchette, J. M. Knipe, J. K. Stolaroff, J. R. Deotte, J. S. Oakdale, A. Maiti, J. M. Lenhardt, S. Sirajuddin, A. C. Rosenzweig, and S. E. Baker, "Printable enzyme-embedded materials for methane to methanol conversion," *Nat. Commun.*, vol. 7, no. May, pp. 1-9, 2016.

[11] J. P. Brody and P. Yager, "Diffusion-based extraction in a microfabricated device," *Sensors Actuators A Phys.*, vol. 58, no. 1, pp. 13-18, 1997.

[12] M. Washizu, S. Suzuki, O. Kurosawa, T. Nishizaka, and T. Shinohara, "Molecular dielectrophoresis of biopolymers," *IEEE Trans. Ind. Appl.*, vol. 30, no. 4, pp. 835-843, 1994.

[13] B. H. Lapizco-Encinas, S. Ozuna-Chac??n, and M. Rito-Palomares, "Protein manipulation with insulator-based dielectrophoresis and direct current electric fields," *J. Chromatogr. A, vol.* 1206, no. 1, pp. 45-51, 2008.

[14] O. Hofmann, D. Che, K. A. Cruickshank, and U. R. Muller, "Adaptation of capillary isoelectric focusing to microchannels on a glass chip," *Anal. Chem.*, vol. 71, no. 3, pp. 678-686, 1999.

[15] S. Song, A. K. Singh, T. J. Shepodd, and B. J. Kirby, "Microchip Dialysis of Proteins Using in Situ Photopatterned Nanoporous Polymer Membranes," *Anal. Chem.*, vol. 76, no. 8, pp. 2367-2373, 2004.

[16] D. Kohlheyer, J. C. T. Eijkel, S. Schlautmann, A. Van Den Berg, and R. B. M. Schasfoort, "Microfluidic high-resolution free-flow isoelectric focusing," *Anal. Chem.*, vol. 79, no. 21, pp. 8190-8198, 2007.

[17] J. Khandurina, S. C. Jacobson, L. C. Waters, R. S. Foote, and J. M. Ramsey, "Microfabricated porous membrane structure for sample concentration and electrophoretic analysis," *Anal. Chem.*, vol. 71, no. 9, pp. 1815-1819, 1999.

[18] R. Dhopeshwarkar, L. Sun, and R. M. Crooks, "Electrokinetic concentration enrichment within a microfluidic device using a hydrogel microplug.," *Lab Chip*, vol. 5, no. 10, pp. 1148-54, 2005.

[19] S. M. Kim, M. a Burns, and E. F. Hasselbrink, "Electrokinetic protein preconcentration using a simple glass/poly(dimethylsiloxane) microfluidic chip.," *Anal. Chem.*, vol. 78, no. 14, pp. 4779-4785, 2006.

[20] B. M. Venkatesan, B. Dorvel, S. Yemenicioglu, N. Watkins, I. Petrov, and R. Bashir, "Highly sensitive, mechanically stable nanopore sensors for DNA analysis," *Adv. Mater.*, vol. 21, no. 27, pp. 2771-2776, 2009.

[21] C. J. Lo, T. Aref, and A. Bezryadin, "Fabrication of symmetric sub-5 nm nanopores using focused ion and electron beams," *Nanotechnology*, vol. 17, no. 13, p. 3264, 2006.

[22] H. Kwok, K. Briggs, and V. Tabard-Cossa, "Nanopore fabrication by controlled dielectric breakdown," *PLoS One*, vol. 9, no. 3, 2014.

[23] S. Y. Chou, "Nanoimprint lithography," *J. Vac. Sci. Technol. B*, vol. 14, no. 6, pp. 4129-4133, 1996.

[24] C. Vieu, F. Carcenac, A. Pepin, Y. Chen, M. Mejias, A. Lebib, L. Manin-Ferlazzo, L. Couraud, and H. Launois, "Electron beam lithography: resolution limits and applications," *Appl. Surf. Sci.*, vol. 164, no. 1, pp. 111-117, 2000.

[25] R. M. McCormick, R. J. Nelson, M. G. Alonso-Amigo, D. J. Benvegnu, and H. H. Hooper, "Microchannel electrophoretic separations of DNA in injection-molded plastic substrates.," *Anal. Chem.*, vol. 69, no. 14, pp. 2626-30, 1997.

[26] H. Becker and U. Heim, "Hot embossing as a method for the fabrication of polymer high aspect ratio structures," *Sensors Actuators, A Phys.*, vol. 83, no. 1, pp. 130-135, 2000.

[27] M. A. Roberts, J. S. Rossier, P. Bercier, and H. Girault, "UV laser machined polymer substrates for the development of microdiagnostic systems," *Anal. Chem.*, vol. 69, no. 11, pp. 2035-2042, 1997.

[28] C. Wang, R. Oleschuk, F. Ouchen, J. Li, P. Thibault, and D. J. Harrison, "Integration of immobilized trypsin bead beds for protein digestion within a microfluidic chip incorporating capillary electrophoresis separations and an electrospray mass spectrometry interface," *Rapid Commun. Mass Spectrom.*, vol. 14, no. 15, pp. 1377-1383, 2000.

[29] D. J. Beebe, J. S. Moore, J. M. Bauer, Q. Yu, R. H. Liu, C. Devadoss, and B.-H. Jo, "Functional hydrogel structures for autonomous flow control inside microfluidic channels: Abstract: Nature," *Nature*, vol. 404, no. 6778, pp. 588-590, 2000.

[30] A. S. Hoffman, "Hydrogels for biomedical applications," *Adv. Drug Deliv. Rev.*, vol. 64, no. SUPPL., pp. 18-23, 2012.

[31] M. M. Ozmen and O. Okay, "Superfast responsive ionic hydrogels with controllable pore size," *Polymer (Guildf).*, vol. 46, no. 19 SPEC. ISS., pp. 8119-8127, 2005.

[32] N. N. Watkins, N. N. Watkins, U. Hassan, G. Damhorst, H. Ni, and A. Vaid, "Microfluidic CD4+ and CD8+ T Lymphocyte Counters for Point-of-Care HIV Diagnostics Using Whole Blood," *Sci. TransL Med.*, vol. 170, no. 214, p. 214ra170, 2013.

[33] P. G. Shankles, A. C. Timm, M. J. Doktycz, and S. T. Retterer, "Fabrication of nanoporous membranes for tuning microbial interactions and biochemical reactions," *J. Vac. Sci. Technol. B*, vol. 33, no. 2015, pp. 6-3, 2015.

[34] Z. Ren, Z. Huang, J. Xu, J. Wang, P. Bush, M. Siegal, and P. Provencio, "Synthesis of large arrays of well-aligned carbon nanotubes on glass," *Science*, vol. 282, no. 5391, pp. 1105-7, 1998.

[35] M. Stadermann, A. D. Mcbrady, B. Dick, R. Reid, A. Noy, R. E. Synovec, O. Bakajin, and V. R. Reid, "Ultrafast Gas Chromatography on Single-Wall Carbon Nanotube Stationary Phases in Microfabricated Channels Ultrafast Gas Chromatography on Single-Wall Carbon Nanotube Stationary Phases in Microfabricated Channels," *Mech. Eng.*, vol. 78, no. 16, pp. 5639-5644, 2006.

[36] Y.-J. Kim and D.-N. Kim, "Structural Basis for Elastic Mechanical Properties of the DNA Double Helix.," *PLoS One*, vol. 11, no. 4, p. e0153228, 2016.

[37] M. Yu, "Strength and Breaking Mechanism of Multi-walled Carbon Nanotubes Under Tensile Load," *Science (80-.).*, vol. 287, no. 5453, pp. 637-640, 2000.

[38] X. Wang, Q. Li, J. Xie, Z. Jin, J. Wang, Y. Li, K. Jiang, and S. Fan, "Fabrication of ultralong and electrically uniform single-walled carbon nanotubes on clean substrates," *Nano Lett.*, vol. 9, no. 9, pp. 3137-3141, 2009.

[39] Z. Liu, F. Galli, K. G. H. Janssen, L. Jiang, H. J. Van Der Linden, D. C. De Geus, P. Voskamp, M.

E. Kuil, R. C. L. Olsthoorn, T. H. Oosterkamp, T. Hankemeier, and J. P. Abrahams, "Stable single-walled carbon nanotube-streptavidin complex for biorecognition," *J. Phys. Chem. C*, vol. 114, no. 10, pp. 4345-4352, 2010.

[40] J. R. Wayment and J. M. Harris, "Controlling binding site densities on glass surfaces," *Anal. Chem.*, vol. 78, no. 22, pp. 7841-7849, 2006.

[41] L. H. Dubois and R. G. Nuzzo, "Organic Surfaces," vol. 43, pp. 437-463, 1992.

[42] I. A. Banerjee, L. Yu, and H. Matsui, "Location-specific biological functionalization on nanotubes: Attachment of proteins at the ends of nanotubes using Au nanocrystal masks," *Nano Lett.*, vol. 3, no. 3, pp. 283-287, 2003.

[43] J. Yu, J. G. Shapter, J. S. Quinton, M. R. Johnston, and D. a Beattie, "Direct attachment of well-aligned single-walled carbon nanotube architectures to silicon (100) surfaces: a simple approach for device assembly.," *Phys. Chem. Chem. Phys.*, vol. 9, no. 4, pp. 510-520, 2007.

[44] Z. Liu, Z. Shen, T. Zhu, S. Hou, and L. Ying, "Organizing Single-Walled Carbon Nanotubes on Gold Using a Wet Chemical Self-Assembling Technique," *Langmuir*, vol. 16, no. 8, pp. 3569-3573, 2000.

[45] M. S. Jung, Y. K. Ko, D. H. Jung, D. H. Choi, H. T. Jung, J. N. Heo, B. H. Sohn, Y. W. Jin, and J.

Kim, "Electrical and field-emission properties of chemically anchored single-walled carbon nanotube patterns," *Appl. Phys. Lett.*, vol. 87, no. 1, pp. 1-4, 2005.

[46] A. Star, Y. Liu, K. Grant, L. Ridvan, J. F. Stoddart, D. W. Steuerman, M. R. Diehl, A. Boukai, and J. R. Heath, "Noncovalent side-wall functionalization of single-walled carbon nanotubes," *Macromolecules*, vol. 36, no. 3, pp. 553-560, 2003.

[47] M. S. Strano, J.-H. Ahn, J.-H. Kim, P. W. Barone, and N. F. Reuel, "Nanotube array for optical detection of protein-protein interactions," U.S. Patent Application 20120178640A1, Jul. 12, 2012.

[48] Q. Zhou, A. Xing, and K. Zhao, "Simultaneous determination of nickel, cobalt and mercury ions in water samples by solid phase extraction using multiwalled carbon nanotubes as adsorbent after chelating with sodium diethyldithiocarbamate prior to high performance liquid chromatography," *J. Chromatogr. A*, vol. 1360, pp. 76-81, 2014.

[49] M. Shim, N. W. S. Kam, R. J. Chen, Y. Li, and H. Dai, "Functionalization of Carbon Nanotubes for Biocompatibility and Biomolecular Recognition," *Nano Lett.*, vol. 2, no. 4, pp. 285-288, 2002.

[50] D. Beckett, E. Kovaleva, and P. J. Schatz, "A minimal peptide substrate in biotin holoenzyme synthetase-catalyzed biotinylation," *Protein Sci.*, vol. 8, pp. 921-929, 1999.

[51] N. T. Ingolia, G. A. Brar, N. Stern-Ginossar, M. S. Harris, G. J. S. Talhouarne, S. E. Jackson, M. R. Wills, and J. S. Weissman, "Ribosome Profiling Reveals Pervasive Translation Outside of Annotated Protein-Coding Genes," *Cell Rep.*, vol. 8, no. 5, pp. 1365-1379, 2014.

[52] E. de Boer, P. Rodriguez, E. Bonte, J. Krijgsveld, E. Katsantoni, A. Heck, F. Grosveld, and J. Strouboulis, "Efficient biotinylation and single-step purification of tagged transcription factors in mammalian cells and transgenic mice," *Proc. Natl. Acad. Sci. U. S. A.*, vol. 100, no. 13, pp. 7480-5, 2003.

[53] A. L. Szymczak-Workman, K. M. Vignali, and D. A. A. Vignali, "Design and Construction of 2A Peptide-Linked Multicistronic Vectors," *Cold Spring Harb. Protoc.*, vol. 2012, no. 2, p. pdb.ip067876-pdb.ip067876, February 2012.

[54] A. Katranidis, W. Grange, R. Schlesinger, T. Choli-Papadopoulou, D. Bruggemann, M. Hegner, and G. Büldt, "Force measurements of the disruption of the nascent polypeptide chain from the ribosome by optical tweezers," *FEBS Lett.*, vol. 585, no. 12, pp. 1859-1863, 2011.

[55] C. Orelle, E. D. Carlson, T. Szal, T. Florin, M. C. Jewett, and A. S. Mankin, "Protein synthesis by ribosomes with tethered subunits," *Nature*, p. doi: 10.1038/nature14862, 2015.

[56] Y. Shimizu, a Inoue, Y. Tomari, T. Suzuki, T. Yokogawa, K. Nishikawa, and T. Ueda, "Cell-free translation reconstituted with purified components.," *Nat. Biotechnol.*, vol. 19, no. 8, pp. 751-5, 2001.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A reusable cell free protein synthesis (CFPS) system for continuously synthesizing protein at a rate of $1.4 \times 10^{-2}$ mg/hr/μL-2.5 mg/hr/μL, the system comprising a plurality of ribosomes attached to a structure, or a plurality of structures, housed, contained, or attached to a solid support,
   wherein the solid support comprises a chamber, at least one fluidic inlet, at least one fluidic outlet, and a solution for containing synthesized protein,
   wherein the plurality of ribosomes are positioned between the fluidic inlet and the fluidic outlet, and
   wherein the solution comprises one or more in vitro translation reagents and synthesized protein moving through the CFPS system and the synthesized protein is collected through the fluidic outlet.

2. The CFPS system of claim 1, wherein the solid support is attached to the structure or the plurality of structures.

3. The CFPS system of claim 1, wherein the structure is a bead, a lattice, an aerogel, foam, or a sponge.

4. The CFPS system of claim 1, wherein the structure is a bead.

5. The CFPS system of claim 4, wherein (a) each bead has an average surface area of 300 nm² to 4 mm² and/or (b) the beads are about the same size or the beads vary in diameter by 60% or more.

6. The CFPS system of claim 4, wherein the solid support is a vessel.

7. The CFPS system of claim 4, wherein the bead is encapsulated or suspended within a hydrogel, gelatin, or polymer contained or housed in the solid support.

8. The CFPS system of claim 1, wherein each structure is attached to the solid support under a controlled condition.

9. The CFPS system of claim 8, wherein each structure is attached only when a magnetic field is applied to the system.

10. The CFPS system of claim 1, wherein the ribosomes are eukaryotic ribosomes, or a variant thereof.

11. The CFPS system of claim 1, wherein the ribosomes are prokaryotic ribosomes, or a variant thereof.

12. The CFPS system of claim 1, wherein the solid support comprises a plurality of pores.

13. The CFPS system of claim 1, wherein the structures are attached to only one side of the solid support.

14. A kit comprising the CFPS system of claim 1 and one or more of: a transfer RNA (tRNA), an amino acid, an enzymatic cofactor, and an energy source.

15. The CFPS system of claim 3, wherein the lattice comprises a plurality of nanowires, nanostrings, or nanothreads.

16. The CFPS system of claim 1, wherein the ribosomes are present at a density of at least $10^5$ ribosomes per cm² of the structure.

17. The CFPS system of claim 1, wherein the ribosomes are present at a density of at least $10^8$ ribosomes per cm² of the structure.

18. The CFPS system of claim 4, wherein the average bead size is 10 nm to 1 mm.

19. The reusable CFPS system of claim 1, wherein the system is a microfluidic system.

20. The reusable CFPS system of claim 1, wherein the system further comprises a filter to retain the ribosomes in the solid support.

21. The reusable CFPS system of claim 1, wherein the solution is capable of being cycled back through the fluidic inlet after passing through the fluidic outlet.

* * * * *

SEQUENCE LISTING

<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1

```
Gly Gly Ser Ser Gly Ser Gly Ser Ser Gly Gly Ser Gly Ser Ser Gly
1               5                   10                  15

Ser Ser Gly Gly Ser
            20
```

<210> SEQ ID NO 2
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 2

```
Gly Leu Asn Asp Ile Phe Glu Ala Gln Lys Ile Glu Trp His Glu
1               5                   10                  15
```